(12) United States Patent
Kaplan

(10) Patent No.: US 9,383,358 B2
(45) Date of Patent: Jul. 5, 2016

(54) METHOD TO ASSESS PATTERNS OF MOLECULAR EXPRESSION

(71) Applicant: Verve, Ltd., Pepper Pike, OH (US)

(72) Inventor: David R. Kaplan, Shaker Heights, OH (US)

(73) Assignee: CellPrint IP Holding, LLC, Cleveland, OH (US)

( * ) Notice: Subject to any disclaimer, the term of this patent is extended or adjusted under 35 U.S.C. 154(b) by 596 days.

(21) Appl. No.: 13/829,557

(22) Filed: Mar. 14, 2013

(65) Prior Publication Data

US 2014/0005062 A1 Jan. 2, 2014

Related U.S. Application Data

(60) Provisional application No. 61/665,628, filed on Jun. 28, 2012, provisional application No. 61/671,240, filed on Jul. 13, 2012, provisional application No. 61/710,482, filed on Oct. 5, 2012, provisional application No. 61/756,626, filed on Jan. 25, 2013.

(51) Int. Cl.
*G01N 33/48* (2006.01)
*G01N 33/569* (2006.01)
*A61K 35/28* (2015.01)
*G06F 19/24* (2011.01)
*C12N 15/10* (2006.01)
*G01N 33/53* (2006.01)
*A61K 35/51* (2015.01)

(52) U.S. Cl.
CPC .......... *G01N 33/56972* (2013.01); *A61K 35/28* (2013.01); *A61K 35/51* (2013.01); *C12N 15/1072* (2013.01); *G01N 33/53* (2013.01); *G06F 19/24* (2013.01); *G01N 2333/70596* (2013.01)

(58) Field of Classification Search
CPC ........................................................ G06F 19/24
USPC ........................................................... 702/19
See application file for complete search history.

(56) References Cited

U.S. PATENT DOCUMENTS

2010/0323027 A1* 12/2010 Lim et al. ...................... 424/520
2012/0219632 A1* 8/2012 Lim ............................. 424/520

OTHER PUBLICATIONS

Kaplan, D., et al. Correlation Between ZAP-70, Phospho-ZAP-70, and Phospho-Syk Expression in Leukomic Cells from Patients with CLL; (2010); Cytometry Part B: Clinical Cytometry; vol. 78B; pp. 115-122.

* cited by examiner

*Primary Examiner* — Jerry Lin
(74) *Attorney, Agent, or Firm* — Tarolli, Sundheim, Covell & Tummino LLP

(57) ABSTRACT

The invention is directed to a method to establish a biologically significant association of gene expression levels among two or more genes, the method comprising assaying a sample for expression levels of two or more genes and identifying statistically-significant associations using a correlation coefficient in the range of about 0.6 to about 1.0, wherein a correlation coefficient in that range signifies a biologically significant correlation.

13 Claims, 42 Drawing Sheets

/translation="MAAATGDPGLSKLQFAPFSSALDVGFWHELTQKKLNEYRLDEAP
KDIKGYYYNGDSAGLPARLTLEFSAFDMSAPTPARCCPAIGTLYNTNTLESFKTADKK
LLLEQAANEIWESIKSGTALENPVLLNKFLLLTFADLKKYHFYYWFCYPALCLPESLP
LIQGPVGLDQRFSLKQIEALECAYDNLCQTEGVTALPYFLIKYDENMVLVSLLKHYSD
FFQGQRTKITIGVYDPCNLAQYPGWPLRNFLVLAAHRWSSSFQSVEVVCFRDRTMQGA
RDVAHSIIFEVKLPEMAFSPDCPKAVGWEKNQKGGMGPRMVNLSECMDPKRLAESSVD
LNLKLMCWRLVPTLDLDKVVSVKCLLLGAGTLGCNVARTLMGWGVRHITFVDNAKISY
SNPVRQPLYEFEDCLGGGKPKALAAADRLQKIFPGVNARGFNMSIPMPGHPVNFSSVT
LEQARRDVEQLEQLIESHDVVFLLMDTRESRWLPAVIAASKRKLVINAALGFDTFVVM
RHGLKKPKQQGAGDLCPNHPVASADLLGSSLFANIPGYKLGCYFCNDVVAPGDSTRDR
TLDQQCTVSRPGLAVIAGALAVELMVSVLQHPEGGYAIASSSDDRMNEPPTSLGLVPH
QIRGFLSRFDNVLPVSLAFDKCTACSSKVLDQYEREGFNFLAKVFNSSHSFLEDLTGL
TLLHQETQAAEIWDMSDDETI"

Human ATG7

Figure 8

```
ctttgcgcac gcgcgccgct tcccagtggc aagcgcgggc aggaccgcgt tgcgtcatcg    60
gggcgcgcgc ctcagagaga gctgtggttg ccggaagttg agcggcggca agaaataatg   120
gcggcagcta cggggggatcc tggactctct aaactgcagt ttgccccttt tagtagtgcc  180
ttggatgttg ggttttggca tgagttgacc cagaagaagc tgaacgagta tcggctggat   240
gaagctccca aggacattaa gggttattac tacaatggtg actctgctgg gctgccagct   300
cgcttaacat tggagttcag tgcttttgac atgagtgctc ccacccagc ccgttgctgc    360
ccagctattg aacactgta taacaccaac acactcgagt ctttcaagac tgcagataag    420
aagctccttt tggaacaagc agcaaatgag atatgggaat ccataaaatc aggcactgct   480
cttgaaaacc ctgtactcct caacaagttc ctcctcttga catttgcaga tctaaagaag   540
taccacttct actattggtt ttgctatcct gccctctgtc ttccagagag tttacctctc   600
attcaggggc cagtgggttt ggatcaaagg ttttcactaa aacagattga agcactagag   660
tgtgcatatg ataatctttg tcaaacagaa ggagtcacag ctcttcctta cttcttaatc   720
aagtatgatg agaacatggt gctggtttcc ttgctttaaac actacagtga tttcttccaa  780
ggtcaaagga cgaagataac aattggtgta tatgatccct gtaacttagc ccagtaccct   840
ggatggcctt tgaggaattt tttggtccta gcagcccaca gatggagtag cagtttccag   900
tctgttgaag ttgtttgctt ccgtgaccgt accatgcagg gggcgagaga cgttgcccac   960
agcatcatct tcgaagtgaa gcttccagaa atggcattta gcccagattg tcctaaagca  1020
gttggatggg aaaagaacca gaaaggaggc atgggaccaa ggatggtgaa cctcagtgaa  1080
tgtatggacc ctaaaaggtt agctgagtca tcagtggatc taaatctcaa actgatgtgt  1140
tggagattgg ttcctacttt agacttggac aaggttgtgt ctgtcaaatg tctgctgctt  1200
ggagccggca ccttgggttg caatgtagct aggacgttga tgggttgggg cgtgagacac  1260
atcacatttg tggacaatgc caagatctcc tactccaatc ctgtgaggca gcctctctat  1320
gagtttgaag attgcctagg gggtggtaag cccaaggctc tggcagcagc ggaccggctc  1380
cagaaaatat tccccggtgt gaatgccaga ggattcaaca tgagcatacc tatgcctggg  1440
catccagtga acttctccag tgtcactctg gagcaagccc gcagagatgt ggagcaactg  1500
gagcagctca tcgaaagcca tgatgtcgtc ttcctattga tggacaccag ggagagccgg  1560
tggcttcctg ccgtcattgc tgcaagcaag agaaagctgg tcatcaatgc tgctttggga  1620
tttgacacat ttgttgtcat gagacatggt ctgaagaaac caaagcagca aggagctggg  1680
gacttgtgtc caaaccaccc tgtggcatct gctgacctcc tgggctcatc gcttttttgcc 1740
aacatccctg gttacaagct tggctgctac ttctgcaatg atgtggtggc cccaggagat  1800
tcaaccagag accggacctt ggaccagcag tgcactgtga gtcgtccagg actggccgtg  1860
attgcaggag ccctggccgt ggaattgatg gtatctgttt tgcagcatcc agaaggggc   1920
tatgccattg ccagcagcag tgacgatcgg atgaatgagc tccaacctc tcttgggctt   1980
gtgcctcacc agatccgggg atttctttca cggtttgata atgtccttcc cgtcagcctg  2040
gcatttgaca aatgtacagc ttgttcttcc aaagttcttg atcaatatga acgagaagga  2100
tttaacttcc tagccaaggt gtttaattct tcacattcct tcttagaaga cttgactggt  2160
cttacattgc tgcatcaaga aacccaagct gctgagatct gggacatgag cgatgatgag  2220
accatctgag atggccccgc tgtggggctg acttctcccc ggccgcctgc tgaggagctc  2280
tccatcgcca gagcaggact gctgacccca ggcctggtga ttctgggccc ctcctccata  2340
ccccgaggtc tgggattccc ccctctgctg cccaggagtg gccagtgttc ggcgttgctc  2400
gggattcaag ataccaccag ttcagagcta aataataacc ttggccttgg ccttgctatt  2460
gacctgggac ttggtcctcc atgcagtttt tatttcttgt cacagtgact gatagccatc  2520
ccccaggatc ctttcccctt ggccctgagg gggtgaccca acacagacca aatggggaaa  2580
tgagcaacca gctcctgccc agagccactg cggaggtgg caccctcatc ccggaatgt    2640
gctgcccacc gcaccgcagg ctcctcctgt gggggccctg ggcatgggtg agggtgggac  2700
cccgtgagcg cactgcaccc tggccctggt ggagcgggag gaggaggaga gccgagctgg  2760
gtacgagact aaagggccca catgacccag tgacgccaga tttccaccaa ggactgagtg  2820
agctgctcag acatggcttt ctgcctccca gcctgtcctc cactgtgggc atagcatctg  2880
tgcctgcctg cctgcttgag ggagaggagt ttctgctgct gccttgagct gggggaaga   2940
gcccaggggc agatcctggc agctgcctgg atgggctcc tccctgccct tatgagcagg   3000
ccaggccag aaaggccgag cctgggctgc cttcctgccc cagccgaggg aggggtcaga  3060
cggctctacc atgggtaact caggcaagag ctggttttcc tctttattct gggtgtgtgc  3120
agctgtgagg cccaaccca ggaggggcca tggcctaggt acctgtgacc accctgcccc   3180
cgtgtagagg gcatcgtctt tcctgctatt ttattctttc agcttttgtc ttaggcccag  3240
aatcaaagtg aaaattgagt cgagctgacc cttacaacag taggatttag tagggtagat  3300
ttcaaatgag gcttcgcttc tcccaaagta gccagtccaa gttccagtgg ctgtcgttca  3360
gctcatggga gcttcatggg gacacagccg gcacaggtgc agggcccgag tccgcccacc  3420
cagcctggcg ctgaaactgc acacgtacac tatgtggttt aagagcactt tattattgtt  3480
cttaaggcta cttttaagta caaaaaaaga tggcctgcca aaccttttt tttcttcttc   3540
caggaaaac agggccacaga gaatggtata ttacagattt acacacatga agagaaggtc  3600
agagcgcact gcaggcagcg cggctctggg aagaacttca cggagcccct tcttagagca  3660
gggaggggc tttctcagtg aaatgtttgg ttttctgctg cctcctctgc cccaggcccc  3720
cctccagggt actgcctatc ccagataggt cagtgcacca gggacccggc cgccagcacc  3780
```

Human ATG7   Figure 9A

```
gccgacccct cccagagtga cgcccttgtt cactgacaaa gagacctgtc ccaggagtgt    3840
cctccaccga gccggtcagc tgtgggtggt tttcctgtta cgacgctcag tagcctgtag    3900
caataacaaa ctcgtggcta tgaatgcaga tgcagtgttc tcatagaata actgttcctg    3960
cacttttaca gacaaatcta cgacaaaaaa aaagatcaac tttttttttc cgaacaacaa    4020
aaaaaatgaa tgattacaat aggaaaggga aaaattaaat agctacatat cattaacaaa    4080
ttaatgttct tcaaaaaata cctacaaatt tctctgtaca ttctttacgc acagcgtaac    4140
gatggtctca aaatcaccca tatagaaaag tgttctcaac gattttcct acagaaaata     4200
tagggcctg aatgccaaag cttggaagcc cagtacagtg ggagtgaaat gtgtgcgggg     4260
caaggagaag ggctttttctt tcctccactt ttcaaaggcc tgcagccact ctgtgactac   4320
aagagccagt cctccgacct tttcacccag tgccaatttc caaaattcaa cagctaaaaa   4380
ctgtaaaacc gggggtcata cggtgtgcag agtccacaaa gccttgcagg tgaggtgacc   4440
acgcccacgt cacctggtca ggtgccatcg tcgtgagcct ctggtgggcc aggtgggaca   4500
cagcacaccc caggggagg ggatagaaac gctcattgac caaaaggag cagctgtgac    4560
ctccacagct gtgtctgtca tgcttgcttc atctaatttc tagttagtag ctattaatat   4620
agcaaataat aaatgcagta ataacagtat aaagtcagag gaatgtatac tgccttggcc   4680
ccagcgtacg aggaagcgta taaaacacca tatcacagat tgtctgtcag taatctgctg   4740
ttcagccaag agagttcaaa gggagcagtt tctgcatgta gggaagttgg aagacacaaa   4800
cccccacctcc cctgggagct tgtaacaaag cagacaggga tgcaaaaata aatgatgtca  4860
gcctgcagcc aaactccagc atcccacacc gcagctgacc cactgctcat cgcgagggcc  4920
tgccaggagc tggcctccg cactacttgt gagtaaagtg aatatcaaat accaatctta   4980
gagtacaact gtaccagcag taagtatatc taggactgta actgacaaaa ataaactaat  5040
tctgaaaaga aaaaaaaaa                                                5059
```

Human ATG7

Figure 9B amino acid sequence:
FASTA                   326                   36,949

```
          10         20         30         40         50         60
   MHRTTRIKIT ELNPHLMCVL CGGYFIDATT IIECLHSFCK TCIVRYLETS KYCPICDVQV 70         80         90        100        110        120
   HKTRPLLNIR SDKTLQDIVY KLVPGLFKNE MKRRRDFYAA HPSADAANGS NEDRGEVADE 130        140        150        160        170        180
   DKRIITDDEI ISLSIEFFDQ NRLDRKVNKD KEKSKEEVND KRYLRCPAAM TVMHLRKFLR 190        200        210        220        230        240
   SKMDIPNTFQ IDVMYEEEPL KDYYTLMDIA YIYTWRRNGP LPLKYRVRPT CKRMKISHQR 250        260        270        280        290        300
   DGLTNAGELE SDSGSDKANS PAGGIPSTSS CLPSPSTPVQ SPHPQFPHIS STMNGTSNSP 310        320
   SGNHQSSFAN RPRKSSVNGS SATSSG
```

Human Bmi-1

Figure 10

/translation="MDFFRVVENQQPPATMPLNVSFTNRNYDLDYDSVQPYFYCDEEE
NFYQQQQQSELQPPAPSEDIWKKFELLPTPPLSPSRRSGLCSPSYVAVTPFSLRGDND
GGGGSFSTADQLEMVTELLGGDMVNQSFICDPDDETFIKNIIIQDCMWSGFSAAAKLV
SEKLASYQAARKDSGSPNPARGHSVCSTSSLYLQDLSAAASECIDPSVVFPYPLNDSS
SPKSCASQDSSAFSPSSDSLLSSTESSPQGSPEPLVLHEETPPTTSSDSEEEQEDEEE
IDVVSVEKRQAPGKRSESGSPSAGGHSKPPHSPLVLKRCHVSTHQHNYAAPPSTRKDY
PAAKRVKLDSVRVLRQISNNRKCTSPRSSDTEENVKRRTHNVLERQRRNELKRSFFAL
RDQIPELENNEKAPKVVILKKATAYILSVQAEEQKLISEEDLLRKRREQLKHKLEQLR
NSCA"

```
gaccccgag   ctgtgctgct   cgcggccgcc   accgccgggc   cccggccgtc   cctggctccc    60
ctcctgcctc  gagaagggca   gggcttctca   gaggcttggc   gggaaaaaga   acggagggag   120
ggatcgcgct  gagtataaaa   gccggttttc   ggggctttat   ctaactcgct   gtagtaattc   180
cagcgagagg  cagagggagc   gagcgggcgg   ccggctaggg   tggaagagcc   gggcgagcag   240
agctgcgctg  cgggcgtcct   gggaagggag   atccggagcg   aataggggc    ttcgcctctg   300
gcccagccct  cccgctgatc   ccccagccag   cggtccgcaa   cccttgccgc   atccacgaaa   360
ctttgcccat  agcagcgggc   gggcactttg   cactggaact   tacaacaccc   gagcaaggac   420
gcgactctcc  cgacgcgggg   aggctattct   gcccatttgg   ggacacttcc   ccgccgctgc   480
caggacccgc  ttctctgaaa   ggctctcctt   gcagctgctt   agacgctgga   ttttttcgg    540
gtagtggaaa  accagcagcc   tcccgcgacg   atgccctca    acgttagctt   caccaacagg   600
aactatgacc  tcgactacga   ctcggtgcag   ccgtatttct   actgcgacga   ggaggagaac   660
ttctaccagc  agcagcagca   gagcgagctg   cagccccgg    cgcccagcga   ggatatctgg   720
aagaaattcg  agctgctgcc   caccccgccc   ctgtcccta    gccgccgctc   cgggctctgc   780
tcgccctcct  acgttgcggt   cacacccttc   tcccttcggg   agacaacga    cggcggtggc   840
gggagcttct  ccacggccga   ccagctggag   atggtgaccg   agctgctggg   aggagacatg   900
gtgaaccaga  gtttcatctg   cgacccggac   gacgagacct   tcatcaaaaa   catcatcatc   960
caggactgta  tgtggagcgg   cttctcggcc   gccgccaagc   tcgtctcaga   gaagctggcc  1020
tcctaccagg  ctgcgcgcaa   agacagcggc   agcccgaacc   ccgcccgcgg   ccacagcgtc  1080
tgctccacct  ccagcttgta   cctgcaggat   ctgagcgccg   ccgcctcaga   gtgcatcgac  1140
ccctcggtgg  tcttcccta    ccctctcaac   gacagcagct   cgcccaagtc   ctgcgcctcg  1200
caagactcca  gcgccttctc   tccgtcctcg   gattctctgc   tcctctcgac   ggagtcctcc  1260
ccgcagggca  gccccgagcc   cctggtgctc   catgaggaga   caccgcccac   caccagcagc  1320
gactctgagg  aggaacaaga   agatgaggaa   gaaatcgatg   ttgtttctgt   ggaaaagagg  1380
caggctcctg  gcaaaaggtc   agagtctgga   tcaccttctg   ctggaggcca   cagcaaacct  1440
cctcacagcc  cactggtcct   caagaggtgc   cacgtctcca   cacatcagca   caactacgca  1500
gcgcctccct  ccactcggaa   ggactatcct   gctgccaaga   gggtcaagtt   ggacagtgtc  1560
agagtcctga  cacagatcag   caacaaccga   aaatgcacca   gcccaggtc    ctcggacacc  1620
gaggagaatg  tcaagaggcg   aacacacaac   gtcttggagc   gccagaggag   gaacgagcta  1680
aaacggagct  ttttgccct    gcgtgaccag   atcccggagt   tggaaaacaa   tgaaaaggcc  1740
cccaaggtag  ttatccttaa   aaaagccaca   gcatacatcc   tgtccgtcca   agcagaggag  1800
caaaagctca  tttctgaaga   ggacttgttg   cggaaacgac   gagaacagtt   gaaacacaaa  1860
cttgaacagc  tacggaactc   ttgtgcgtaa   ggaaaagtaa   ggaaaacgat   tccttctaac  1920
agaaatgtcc  tgagcaatca   cctatgaact   tgtttcaaat   gcatgatcaa   atgcaacctc  1980
acaaccttgg  ctgagtcttg   agactgaaag   atttagccat   aatgtaaact   gcctcaaatt  2040
ggactttggg  cataaaagaa   cttttttatg   cttaccatct   tttttttttc   tttaacagat  2100
ttgtatttaa  gaattgtttt   taaaaaattt   taagatttac   acaatgtttc   tctgtaaata  2160
ttgccattaa  atgtaaataa   cttaataaa    acgtttatag   cagttacaca   gaatttcaat  2220
cctagtatat  agtacctagt   attataggta   ctataaaccc   taattttttt   tatttaagta  2280
catttttgctt tttaaagttg   attttttttct  attgttttta   gaaaaataa    aataactggc  2340
aaatatatca  ttgagccaaa   tcttaaaaaa   aaaaaaaa                              2379
```

Human C-Myc     Figure 11

/translation="MNQPQRMAPVGTDKELSDLLDFSMMFPLPVTNGKGRPASLAGAQ
FGGSGLEDRPSSGSWGSGDQSSSSFDPSRTFSEGTHFTESHSSLSSSTFLGPGLGGKS
GERGAYASFGRDAGVGGLTQAGFLSGELALNSPGPLSPSGMKGTSQYYPSYSGSSRRR
AADGSLDTQPKKVRKVPPGLPSSVYPPSSGEDYGRDATAYPSAKTPSSTYPAPFYVAD
GSLHPSAELWSPPGQAGFGPMLGGGSSPLPLPPGSGPVGSSGSSSTFGGLHQHERMGY
QLHGAEVNGGLPSASSFSSAPGATYGGVSSHTPPVSGADSLLGSRGTTAGSSGDALGK
ALASIYSPDHSSNNFSSSPSTPVGSPQGLAGTSQWPRAGAPGALSPSYDGGLHGLQSK
IEDHLDEAIHVLRSHAVGTAGDMHTLLPGHGALASGFTGPMSLGGRHAGLVGGSHPED
GLAGSTSLMHNHAALPSQPGTLPDLSRPPDSYSGLGRAGATAAASEIKREEKEDEENT
SAADHSEEEKKELKAPRARTSSTDEVLSLEEKDLRDRERRMANNARERVRVRDINEAF
RELGRMCQMHLKSDKAQTKLLILQQAVQVILGLEQQVRERNLNPKAACLKRREEEKVS
GVVGDPQMVLSAPHPGLSEAHNPAGHM"

Human E47

Figure 12

| | | | | | |
|---|---|---|---|---|---|
| ggtttccagg | cctgaggtgc | ccgccctggc | cccaggagaa | tgaaccagcc | gcagaggatg | 60 |
| gcgcctgtgg | gcacagacaa | ggagctcagt | gacctcctgg | acttcagcat | gatgttcccg | 120 |
| ctgcctgtca | ccaacgggaa | gggccggccc | gcctccctgg | ccggggcgca | gttcggaggt | 180 |
| tcaggtcttg | aggaccggcc | cagctcaggc | tcctggggca | gcggcgacca | gagcagctcc | 240 |
| tcctttgacc | ccagccggac | cttcagcgag | ggcacccact | tcactgagtc | gcacagcagc | 300 |
| ctctcttcat | ccacattcct | gggaccggga | ctcggaggca | agagcggtga | gcggggcgcc | 360 |
| tatgcctcct | tcgggagaga | cgcaggcgtg | ggcggcctga | ctcaggctgg | cttcctgtca | 420 |
| ggcgagctgg | ccctcaacag | ccccgggccc | ctgtcccctt | cgggcatgaa | ggggacctcc | 480 |
| cagtactacc | cctcctactc | cggcagctcc | cggcggagag | cggcagacgg | cagcctagac | 540 |
| acgcagccca | agaaggtccg | gaaggtcccg | ccgggtcttc | catcctcggt | gtacccaccc | 600 |
| agctcaggtg | aggactacgg | cagggatgcc | accgcctacc | cgtccgccaa | gaccccccagc | 660 |
| agcacctatc | ccgccccctt | ctacgtggca | gatggcagcc | tgcacccctc | agccgagctc | 720 |
| tggagtcccc | cgggccaggc | gggcttcggg | cccatgctgg | gtggggctc | atccccgctg | 780 |
| cccctcccgc | ccggtagcgg | cccggtgggc | agcagtggaa | gcagcagcac | gtttggtggc | 840 |
| ctgcaccagc | acgagcgtat | gggctaccag | ctgcatggag | cagaggtgaa | cggtgggctc | 900 |
| ccatctgcat | cctccttctc | ctcagccccc | ggagccacgt | acggcggcgt | ctccagccac | 960 |
| acgccgcctg | tcagcggggc | cgacagcctc | ctgggctccc | gagggaccac | agctggcagc | 1020 |
| tccggggatg | ccctcggcaa | agcactggcc | tcgatctact | ccccggatca | ctcaagcaat | 1080 |
| aacttctcgt | ccagcccttc | taccccgtg | ggctccccc | agggcctggc | aggaacgtca | 1140 |
| cagtggcctc | gagcaggagc | ccccggtgcc | ttatcgccca | gctacgacgg | gggtctccac | 1200 |
| ggcctgcaga | gtaagataga | agaccacctg | gacgaggcca | tccacgtgct | ccgcagccac | 1260 |
| gccgtgggca | cagccggcga | catgcacacg | ctgctgcctg | gccacggggc | gctggcctca | 1320 |
| ggtttcaccg | gccccatgtc | actgggcggg | cggcacgcag | gcctggttgg | aggcagccac | 1380 |
| cccgaggacg | gcctcgcagg | cagcaccagc | ctcatgcaca | accacgcggc | cctccccagc | 1440 |
| cagccaggca | ccctccctga | cctgtctcgg | cctccgact | cctacagtgg | gctagggcga | 1500 |
| gcaggtgcca | cggcggccgc | cagcgagatc | aagcgggagg | agaaggagga | cgaggagaac | 1560 |
| acgtcagcgg | ctgaccactc | ggaggaggag | aagaaggagc | tgaaggcccc | ccgggcccgg | 1620 |
| accagcagta | cggacgaggt | gctgtccctg | gaggagaaag | acctgaggga | ccgggagagg | 1680 |
| cgcatggcca | ataacgcgcg | ggagcgggtg | cgcgtgcggg | atattaacga | ggccttccgg | 1740 |
| gagctggggc | gcatgtgcca | gatgcacctc | aagtcggaca | agcgcagac | caagctgctc | 1800 |
| atcctgcagc | aggccgtgca | ggtcatcctg | gggctggagc | agcaggtgcg | agagcggaac | 1860 |
| ctgaatccca | aagcagcctg | tttgaaacgg | cgagaagagg | aaaaggtgtc | aggtgtggtt | 1920 |
| ggagaccccc | agatggtgct | ttcagctccc | cacccaggcc | tgagcgaagc | ccacaaccc | 1980 |
| gccgggcaca | tgtgaaagta | aacaaaacct | gaaagcaagc | aacaaaacat | acactttgtc | 2040 |
| agagaagaaa | aaaatgcctt | aactataaaa | agcggagaaa | tggaaacata | tcactcaagg | 2100 |
| gggatgctgt | ggaaacctgg | cttattcttc | taaagccacc | agcaaattgt | gcctaagcga | 2160 |
| aatatttttt | ttaaggaaaa | taaaaacatt | agttacaaga | tttttttttt | cttaatgtag | 2220 |
| atgaaaatta | gcaaggatgc | tgcctttggt | ctctggtttt | tttaagcttt | ttttgcatat | 2280 |
| gttttgtaag | caacaaattt | ttttgtataa | aagtccgtg | tctctcgcta | tttctgctgc | 2340 |
| tgttcctaga | ctgagcattg | catttcttga | tcaaccagat | gattaaacgt | tgtattaaaa | 2400 |
| agacccccgtg | taaacctgag | ccccccgtc | ccccccccc | ccggaagcc | actgcacaca | 2460 |
| gacagaacgg | ggacaggcgg | cgggtctttt | gttttttga | tgttgggggt | tctcttggtt | 2520 |
| ttgtcatgtg | gaaagtgatg | cgtgggcgtt | ccctgatgaa | ggcaccttgg | ggcttccctg | 2580 |
| ccgcatcctc | tcccctcagg | aaggggactg | acctgggctt | ggggaaggg | acgtcagcaa | 2640 |
| ggtggctctg | accctcccag | gtgactctgc | caagcagctg | tggcccccag | ggctacccta | 2700 |

Human E47        Figure 13A

```
cacaacgccc tccccaggcc cccctaagct gctctccctt ggaacctgca cagctctctg   2760
aaatggggca ttttgttggg accagtgacc cctggcatgg ggaccacacc ctggagcccg   2820
gtgctgggga cctcctggac accctgtcct tcactccttt gccccaggga cccaggctca   2880
tgctctgaac tctggctgag aggatgctgc tcaggagcca gcacaggaca ccccccaccc   2940
caccccacca tgtccccatt acaccagagg gccatcgtga cgtagacagg atgccagggg   3000
cctggccagc ctcccccaat gctggggagc atccctgggc ctggggccac acctgctgcc   3060
ctccctctgt gtggtccaag ggcaagagtg gctggagccg ggggactgtg ctggtctgag   3120
cccacgaag gccttgggct gtgcgtccga ccctgctgca gaaccagcag ggtgtcccct   3180
cgggcccatc tgtgtcccat gtcccagcac ccaggcctct ctccaggtct ccttttctgg   3240
tcttttgcca tgagggtaac cagctcttcc cagctggctg gggactgtct tgggtttaaa   3300
actgcaagtc tcctaccctg ggatcccatc cagttccaca cgaactaggg cagtggtcac   3360
tgtggcaccc aggtgtgggc ctggctagct gggggccttc atgtgccctt catgcccctc   3420
cctgcattga ggccttgtgg accctgggc tggctgtgtt catccccgct gcaggtcggg   3480
cgtctccccc cgtgccactc ctgagactcc caccgttacc cccaggagat cctggactgc   3540
ctgactcccc tccccagact ggcttgggag cctgggcccc atggtagatg caagggaaac   3600
ctcaaggcca gctcaatgcc tggtatctgc ccccagtcca ggccaggcgg aggggagggg   3660
ctgtccggct gcctctccct tctcggtggc ttccctacg ccctgggagt ttgatctctt   3720
aagggaactt gcctctccct cttgttttgc tcctggccct gcccctaggt ctgggtgggc   3780
agtggcccca tagcctctgg aactgtgcgt tctgcataga attcaaacga gattcaccca   3840
gcgcgaggag gaagaaacag cagttcctgg gaaccacaat tatgggggt gggggtgtg   3900
atctgagtgc ctcaagatgg ttttcaaaaa aattttttta aagaaaataa ttgtatacgt   3960
gtcaacacag ctggctggat gattgggact ttaaaacgac cctctttcag gtggattcag   4020
agacctgtcc tgtatataac agcactgtag caataaacgt gacattttat aacgatgc     4078
```

Human E47

Figure 13B

/translation="MEVAPEQPRWMAHPAVLNAQHPDSHHPGLAHNYMEPAQLLPPDE
VDVFFNHLDSQGNPYYANPAHARARVSYSPAHARLTGGQMCRPHLLHSPGLPWLDGGK
AALSAAAAHHHNPWTVSPFSKTPLHPSAAGGPGGPLSVYPGAGGGSGGGSGSSVASLT
PTAAHSGSHLFGFPPTPPKEVSPDPSTTGAASPASSSAGGSAARGEDKDGVKYQVSLT
ESMKMESGSPLRPGLATMGTQPATHHPIPTYPSYVPAAAHDYSSGLFHPGGFLGGPAS
SFTPKQRSKARSCSEGRECVNCGATATPLWRRDGTGHYLCNACGLYHKMNGQNRPLIK
PKRRLSAARRAGTCCANCQTTTTTLWRRNANGDPVCNACGLYYKLHNVNRPLTMKKEG
IQTRNRKMSNKSKKSKKGAECFEELSKCMQEKSSPFSAAALAGHMAPVGHLPPFSHSG
HILPTPTPIHPSSSLSFGHPHPSSMVTAMG"

Human GATA-2      Figure 14

```
          10         20         30         40         50         60
MAMSSFLINS NYVDPKFPPC EEYSQSDYLP SDHSPGYYAG GQRRESSFQP EAGFGRRAAC 70         80         90        100        110        120
TVQRYAACRD PGPPPPPPPP PPPPPPPGLS PRAPAPPPAG ALLPEPGQRC EAVSSSPPPP 130        140        150        160        170        180
PCAQNPLHPS PSHSACKEPV VYPWMRKVHV STVNPNYAGG EPKRSRTAYT RQQVLELEKE 190        200        210        220        230        240
FHYNRYLTRR RRVEIAHALC LSERQIKIWF QNRRMKWKKD HKLPNTKIRS GGAAGSAGGP

250
PGRPNGGPRA L
```

Human Hox B4

Figure 15

/translation="MFGLKRNAVIGLNLYCGGAGLGAGSGGATRPGGRLLATEKEASA
RREIGGGEAGAVIGGSAGASPPSTLTPDSRRVARPPPIGAEVPDVTATPARLLFFAPT
RRAAPLEEMEAPAADAIMSPEEELDGYEPEPLGKRPAVLPLLELVGESGNNTSTDGSL
PSTPPPAEEEEDELYRQSLEIISRYLREQATGAKDTKPMGRSGATSRKALETLRRVGD
GVQRNHETAFQGMLRKLDIKNEDDVKSLSRVMIHVFSDGVTNWGRIVTLISFGAFVAK
HLKTINQESCIEPLAESITDVLVRTKRDWLVKQRGWDGFVEFFHVEDLEGGIRNVLLA
FAGVAGVGAGLAYLIR"

```
tctttgagat ggagtcttcc tctatcaccc aggctggagt gcagtggcac aatctcagct       60
cactgcaacc tccgcctccc gagttcaagc aattctcctg ccacagcctc tgcagtagct      120
gggattacag cacccatca ccacgcccaa ctaattttg tatttttagt agagatgggg       180
tttcaccatg ttggccaggc tggtcttgaa ctcctgacct taggtgatcc acccacctcg      240
gcctcccaaa gttctgggat tacaggcgtg agctaccacg cctggccaaa ttatgatctt      300
atatgtgaaa atgattatgt aaaaatgatt gattatggtg ttgtgatggg agatgctgtg      360
ctgtcggcac agtagtaggg cataggctgg gcgcggtggc tcacgcctgt aatcccagca      420
ctttgggagg ccgaggtggg cggatcacga ggtcaggaga tcgagaccat cttggctaac      480
acggtgaaac cctgtctcta ctaaaaatac aaaaaattag ccaggcgcct gtagtcccag      540
ctactcggga ggctgaggca agaatggc gtgaacccgg gagacggagc ttgcagtgag      600
ccgagatagc gccatggcag tccggcctgg gtgaaagagc aagactctgt ctcaaaaaaa      660
aaaaaaaaat acaaaaatta gctgggtgta atggcacgcg cctgtagtcc cagctattca      720
ggaggctgag gccgaattgc ttgaacctgg gtggtggaag ttgcagtgag ccaagaccgc      780
gccattgcac tccaacctgg gcggcagagc aaggctccat ctcaaaaaaa aaaaaaaaa      840
aaaaaaaaaa aggccgggcg cagcggctca catttgtaat cccagcactt tgggaggctg      900
aggcaggtgg atcacaaggt caggagtttg agaccggcct ggctaacata gtgaaaccct      960
gtctctacta aaaatacaaa aattagccgg gcatggtggt gcgcacctgt agtcccagct     1020
```

Human Mc1-1

Figure 16A

```
acttgggagg ctgaggcagg agaaacggtt gaacccagga ggtggaggtt gtggtgagcc    1080
gagattgtgc cactccactc cagcctgggc aacagagcaa gactccgtct caaaaaaaaa    1140
ataagtaaaa taaaataaaa taaaatgtat ttgaaactgg gtgtggtggc tcatgcttat    1200
aatcccagct attcaagagg ctcaggtggg aggatccctt gaggacagga gttgtagacc    1260
atcctggata acatagcaag actttgttac tttctttctt ttttttttt tgagacagag     1320
tctcgttctg ttgcccaggc tggagtgcag tggcacgatc tcggctcact gaaagctctg    1380
cctcccggat tcatgccatt ctcctgcctc agcctcctga gtagctggga ctataggcac    1440
ccgccaccat gcccagctaa ttttttcgtat tttttttta gtagagacgg ggtttcaccg    1500
tgttggccag gatggtcttg atctcctgac ctcgtgatct gcccgcctca gcctcccaaa    1560
gtgctggat tacaggcgtg agccaccgtg cccgaccaag acttgtttcc taacaaacag     1620
ggccagttgc aatggctcat gcctataatc ctagcacttt gggaggccaa ggagggcaga    1680
tggcttgagg ccaggagttc gagattggcc tggacaacat ggtgaaaccc catctctaca    1740
aaaaaacaca aaaattagcc aggcatggtg gtgctggcct gttgtcccag ctacttggga    1800
agctgaggta ggagtatcac tttagctcag gaggtcaagg ttgcagtgag ccgagactgc    1860
accactgcac tccagcctga gcaacatggt gatacccgtc tcaaaaaata ataataacaa    1920
ataatgaata aatgcaattt attttaaagt gaaacttgca tttccttttt tagcctctgt    1980
acaaggaaaa atcattgctc ctcctatttc ctcaatctct ttccacttta ccacctgata    2040
aaatttact ttataaagca tgagagcaaa gctacctcct ccataacact ttcctctagc     2100
tctctcagcc caaagtgaat ttcccaacct cttaactcca aaatgaagtt gttaatgcct    2160
tgtgtagagc atacattcca tctcacatta tggttagttg ctgtacaaga ttagacattc    2220
cttaaataga gaaactattt cttattcact ataaccacaa aatgctctat ccttgccact    2280
catactataa accctatgg ttctaggtcc tgcccaaaac ataaatgggt ggtatggacg      2340
ccgtatcacc ttactaaact gtgacatttt ggggattagg aacttttggc caagagggag    2400
actcacgcct ataattccaa cactttattt atttatttat ttttgagatg gcgtttcgct    2460
cttgttgtcc aggctggagt gcaatggcgc actctcagct caccgcaacc tccgcctccc    2520
aggttcaagc gattctcccg cctcagcctt ccaagtagct gggattacag gcacgtgcca    2580
ccacggcccg gctaattttg tattttagt agagatggag tttctccatg ttggttgggc     2640
tggtctcaaa ctcctgacct cagatgattc gcccgccttg gcctcccaaa gtgctggat    2700
tgcaggtgtg agccactgcg ccaggcctca ttattattat tatttttttt gagaccaagt    2760
cttgctctgt tgcccaggct ggagtgcagt ggcactatct tggctcaccg caacctccgt    2820
ctcttgggtt caagcagttc tcctgtctca gcctccagag tagctggtat tacagatgcg    2880
caccaccaca cccatctaat ttttgtgttt ttagtagaga cagggtttcg ccatgtttcc    2940
caggctggtc tcaaactcct gggctcaagc gatccaccca cctcagcctc ccaaagtgct    3000
gggattattg gcatgaggca cagagcccgg tctgtaatcc caacactttg ggaggccaag    3060
gtaggaggat caccctgagtc caggagttca agaccggcct gggcaaaata gtgatacccc   3120
atctctacaa gaaataaaaa aattagccaa gtataggggc atgcacctgt gttcctcgct    3180
actcgcgagg ctgtggtggg aggatcactt cagcccagga ggttgaggca gcaatgagca    3240
ctgatggtgc cactgcactc cagcctgggt gacagggcaa gacctcatct caaaaaaata    3300
aataaaaagt gagcttgctc acctttccta tgtctctcag caccttgctt ttgaattta     3360
gctattattt ttacagatct tttaacaaaa aggctgcttt aattaacgtt aactaacata    3420
catggcatat aagaagatcc ttgttctcaa gggctttaca aacctctaga gtcaaatgtg    3480
ccttattatc agtacaaaaa taaatggtgt cagctgggtg cagtgactca cacctgtaat    3540
```

Human Mc1-1      Figure 16B

```
cccagcactt taagaggctg aggcaggtgg atcacctgag gccaggagtt tgagaccagc 3600
ctggccaaca tggtgaaacc acattgtcag gcctctgagc ccaagccaag ccatcgcatc 3660
ccctgtgact tgcacgtata catccagatg gcctgaagta actgaagatc cacaaaagaa 3720
gtaaaaatag ccttaactga tgacattcca ccattgtgat ttgtttctgc cccacccgaa 3780
ctgatcaatg tactttgtaa tctcccccac ccttaagaag gttctttgta attctcccca 3840
cccttgagaa tgtactttgt gagatccacc cctgcccaca aaacattgct ctcaacttca 3900
ccacctatcc caaaacctgt aagaactaat gataatccat caccctttgc tgactctctt 3960
ttcggactca gcccgcctgc acccaggtga aataaacagc catgttgctc acacaaagcc 4020
tgtttggtgg tgtcttcaca cagacgcgca tgaaacacat ctctactaaa aatacaataa 4080
tcagctgggc gaggtggctc acagctgtaa tctcagcact tgggaggcc gagacaggca 4140
ggtcacttga ggccatgagt tcgagaccag cctggccaac atcgtgaaaa ccccatctct 4200
accaaaaata caaaaactag ccagatgtgg tggcgcacgc ctgtaatccc agctactcgg 4260
gaggctgagg taccgaatcg tctgaacgtg ggaagtggag cttgtagtga gccgagatcg 4320
ccccactgca ctccagcctg ggcaacagag ctagactgtc tcaaaacaaa caaaaaatgg 4380
tgtcaagact ctcagacgag attctaatgg attaaggcct atatgtaaat agcaccaaag 4440
actatggaac agagatggga gaagcaagca gggaggcagg aatagtttag ctgtggcagt 4500
tttagcttag tccacttaca taaatggttc tttagggtag cacgtggagc atcctcattt 4560
ccaaacattg gactgagagt agagagctgt gcaaaataac cacaagtccc caactatgcc 4620
ctcttaatta tccctatcat ctaagactgt tgttcccatc catcactgaa cttccccgtc 4680
ctcttccttc aacccctgtg ttagtcaatg gttgaaattt tgatttggta aaaaacctct 4740
ggcgaaaacc agcaaaaagg gctcacaaat caggtctcag ggaagcacag aggtagccac 4800
gagaaggccc gaggtgctca tggaaagagc tcgagcccag gagctctggg aggaccccag 4860
gcgctcggag ccgccgttac gtaaccggca ctcagagcct ccgaagaccg gaaggccccg 4920
ctcaggcccc ggctcaggcc ccggccccgg ccccggcccc ggccccgccc cggccggcc 4980
gggcagctgg taggtgccgt gcgcaaccct ccggaagctg ccgccccttt cccttttat 5040
gggaatactt tttttaaaaa aaagagttc gctggcgcca cccgtagga ctggccgccc 5100
taaaaccgtg ataaaggagc tgctcgccac ttctcacttc cgcttccttc cagtaaggag 5160
tcggggtctt ccccagtttt ctcagccagg cggcggcggc gactggcaat gtttggcctc 5220
aaaagaaacg cggtaatcgg actcaacctc tactgtgggg gggccggctt ggggccggc 5280
agcggcggcg ccacccgccc ggggagggcga cttttggcta cggagaagga ggcctcggcc 5340
cggcgagaga tagggggagg ggaggccggc gcggtgattg gcggaagcgc cggcgcaagc 5400
cccccgtcca ccctcacgcc agactcccgg agggtcgcgc ggccgccgcc cattggcgcc 5460
gaggtccccg acgtcaccgc gaccccgcg aggctgcttt cttcgcgcc cacccgccgc 5520
gcggcgccgc ttgaggagat ggaagcccg gccgctgacg ccatcatgtc gcccgaagag 5580
gagctggacg ggtacgagcc ggagcctctc gggaagcggc cggctgtcct gccgctgctg 5640
gagttggtcg gggaatctgg taataacacc agtacggacg ggtcactacc ctcgacgccg 5700
ccgccagcag aggaggagga ggacgagttg taccggcagt cgctggagat tatctctcgg 5760
taccttcggg agcaggccac cggcgccaag gacacaaagc caatgggcag gtctggggcc 5820
accagcagga aggcgctgga gaccttacga cgggttgggg atggcgtgca gcgcaaccac 5880
```
Human Mc1-1

Figure 16C

```
gagacggcct tccaaggtaa gggggttcat taatcgccaa ggcctcactc ccttttttcc   5940
atctctcccc ggactcaccc gccaagggtg ggttggaaac cgaaacgagt cagtgttgaa   6000
acgtgtctca tcctattcct gaagccagaa tattctggcc atgagtcatt gtttccgccc   6060
atcttgattc ttttggaaat ggcagctctt gttcaaagac cggaagggt gggatgtcaa    6120
tttcaagtgg ggtcaacctg agttctgtaa atcccagtag cgattttccc gccgcgggtg   6180
ggcaggcgaa tcttgcgccg gtttagacaa aggaggccgt gaggacctgc atgcttttct   6240
ttctcaggca tgcttcggaa actggacatc aaaaacgaag acgatgtgaa atcgttgtct   6300
cgagtgatga tccatgtttt cagcgacggc gtaacaaact ggggcaggat tgtgactctc   6360
atttcttttg gtgcctttgt ggctaaacac ttgaagacca taaaccaaga aagctgcatc   6420
gaaccattag cagaaagtat cacagacgtt ctcgtaagga caaaacggga ctggctagtt   6480
aaacaaagag ctgggtaag tttgccttaa ggatgaaagg ggccttggag tggaagtaga    6540
atgaaggatt ttttttagag aggtgggat atctaaaggt ttttatgacg cacggctgtt    6600
tgcaggctct aactaaagga ccattgttta tttgatgttg atttaagtag tggatcctta   6660
gagatagtgg tatggcggtc ttgaattgta tcaaaaatct tggttttctc taggcaattt   6720
tttgttccaa ttcagttgaa tactcttcag tggattcaaa ccatgaaaaa ataagtcacc   6780
agggaggat agctgaaata attcctaagg cggtgcctgt tttaatggag aagatatggg    6840
gtggagcctg cgttttaaac aaacccagat ctgatgcagg atgtacttaa ctacgttgag   6900
aaaaactgat ctgcgcaatt gaggcgttac tgaaatatta ggtggtggag atttgagaat   6960
aagggttttc gtcttttacc tcatgggaac tctggaagtc cttttgttag gataaatcct   7020
aataagacca agatagtact gtaaaatgaa gtttaattat catgggtccc cgcttaagaa   7080
actgaagaac ttattttctt tttttgcccc ggggtgaata ataattggtt tactattgct   7140
ttagggggaa accttagata ttttaattta ccttctctct ggatagtagt gttgtaagag   7200
agcagaaacc catacttgaa aatgtgcttt tctttttgt tttctaggat gggtttgtgg    7260
agttcttcca tgtagaggac ctagaaggtg gcatcaggaa tgtgctgctg gcttttgcag   7320
gtgttgctgg agtaggagct ggtttggcat atctaataag atagccttac tgtaagtgca   7380
atagttgact tttaaccaac caccaccacc accaaaacca gtttatgcag ttggactcca   7440
agctgtaact tcctagagtt gcaccctagc aacctagcca gaaaagcaag tggcaagagg   7500
attatggcta acaagaataa atacatggga agagtgctcc ccattgattg aagagtcact   7560
gtctgaaaga agcaaagttc agtttcagca acaaacaaac tttgtttggg aagctatgga   7620
ggaggacttt tagatttagt gaagatggta gggtggaaag acttaatttc cttgttgaga   7680
acaggaaagt ggccagtagc caggcaagtc atagaattga ttacccgccg aattcattaa   7740
tttactgtag tgttaagaga agcactaaga atgccagtga cctgtgtaaa agttacaagt   7800
aatagaacta tgactgtaag cctcagtact gtacaaggga agcttttcct ctctctaatt   7860
agctttccca gtatacttct tagaaagtcc aagtgttcag gacttttata cctgttatac   7920
tttggcttgg tttccatgat tcttacttta ttagcctagt ttatcaccaa taatacttga   7980
cggaaggctc agtaattagt tatgaatatg gatatcctca attcttaaga cagcttgtaa   8040
atgtatttgt aaaaattgta tatatttta cagaaagtct atttctttga aacgaaggaa    8100
gtatcgaatt tacattagtt ttttcatac ccttttgaac tttgcaactt ccgtaattag    8160
gaacctgttt cttacagctt ttctatgcta aactttgttc tgttcagttc tagagtgtat   8220
acagaacgaa ttgatgtgta actgtatgca gactggttgt agtggaacaa atctgataac   8280
tatgcaggtt taaattttct tatctgattt tggtaagtat tccttagata ggttttcttt   8340
tgaaaacctg ggattgagag gttgatgaat ggaaattctt tcacttcatt atatgcaagt   8400
```

Human Mc1-1  Figure 16D

```
tttcaataat taggtctaag tggagtttta aggttactga tgacttacaa ataatgggct  8460
ctgattgggc aatactcatt tgagttcctt ccatttgacc taatttaact ggtgaaattt  8520
aaagtgaatt catgggctca tctttaaagc ttttactaaa agattttcag ctgaatggaa  8580
ctcattagct gtgtgcatat aaaaagatca catcaggtgg atggagagac atttgatccc  8640
ttgtttgctt aataaattat aaaatgatgg cttggaaaag caggctagtc taaccatggt  8700
gctattatta ggcttgcttg ttacacacac aggtctaagc ctagtatgtc aataaagcaa  8760
atacttactg ttttgtttct attaatgatt cccaaacctt gttgcaagtt tttgcattgg  8820
catctttgga tttcagtctt gatgtttgtt ctatcagact taaccttta tttcctgtcc  8880
ttccttgaaa ttgctgattg ttctgctccc ctacagata tttatatcaa ttcctacagc  8940
tttcccctgc catccctgaa ctctttctag ccctttaga ttttggcact gtgaaacccc  9000
tgctggaaac ctgagtgacc ctccctcccc accaagagtc cacagacctt tcatctttca  9060
cgaacttgat cctgttagca ggtggtaata ccatgggtgc tgtgacacta acagtcattg  9120
agaggtggga ggaagtccct tttccttgga ctggtatctt ttcaactatt gttttatcct  9180
gtctttgggg gcaatgtgtc aaaagtcccc tcaggaattt tcagaggaaa gaacatttta  9240
tgaggctttc tctaaagttt cctttgtata ggagtatgct cacttaaatt tacagaaaga  9300
ggtgagctgt gttaaacctc agagtttaaa agctactgat aaactgaaga aagtgtctat  9360
attggaacta gggtcatttg aaagcttcag tctcggaaca tgacctttag tctgtggact  9420
ccatttaaaa ataggtatga ataagatgac taagaatgta atggggaaga actgccctgc  9480
ctgcccatct cagagccata aggtcatctt tgctagagct atttttacct atgtatttat  9540
cgttcttgat cataagccgc ttatttatat catgtatctc taaggaccta aaagcacttt  9600
atgtagtttt taattaatct taagatctgg ttacggtaac taaaaaagcc tgtctgccaa  9660
atccagtgga aacaagtgca tagatgtgaa ttggtttta ggggccccac ttcccaattc  9720
attaggtatg actgtggaaa tacagacaag gatcttagtt gatattttgg gcttggggca  9780
gtgagggctt aggacacccc aagtggtttg ggaaaggagg aggggagtgg tgggtttata  9840
gggggaggag gaggcaggtg gtctaagtgc tgactggcta cgtagttcgg gcaaatcctc  9900
caaaagggaa agggaggatt tgcttagaag gatggcgctc ccagtgacta cttttttgact  9960
tctgtttgtc ttacgcttct ctcagggaaa aacatgcagt cctctagtgt ttcatgtaca 10020
ttctgtgggg ggtgaacacc ttggttctgg ttaaacagct gtactttga tagctgtgcc 10080
aggaagggtt aggaccaact acaaattaat gttggttgtc aaatgtagtg tgtttcccta 10140
actttctgtt tttcctgaga aaaaaaaata aatcttttat tcaaatacag ggtgtgatat 10200
gggtcttttc tcatcgacgc ctcttttttcc ttccctctct taggcaaacc ttttagagaa 10260
gtcagctgag caaatatgta caggtgaatt caaagcaaaa gcctcacaaa gttgatttgc 10320
cttagagcaa aggacagttc ctttcttcaa ttctaattag aggtgttggg ttttttaatta 10380
aatatattac tgctgtactt agaggagttc ttaaacctcc aagtaaaatc aaaaacctct 10440
ttaaaatcaa aatttctgtc ttgatttatt tatttattat ttttttttg agatggagtt 10500
ttgctcttgt tgtccaggct ggagtgcaat ggcacgatct ccgctcaccg caacctccgc 10560
ctcccaggtt caaatgattc tcctgcctca gcctctgag tagctgggaa tacaggcatg 10620
cgccaccaca cccagataat tttgtatttt tagtagagat ggggtttctc cgtgttggtc 10680
aggctggtct tgaactcccg acctcaggtg atctgcccac ctctgcctcc cagagtgcca 10740
```

Human Mc1-1

Figure 16E

```
ggattacagg cgtgagccat cgcacccagc ctctgtcttg atttttttga atcaccaggt  10800
gttggtatgt tttgttttgt tttgttttga ggcacagtct cactcttttg cccaggctag  10860
agtgcagtgg ggcaatctcg gctcactgca acctcagcct cccgagtagc tgggattaca  10920
ggtgcccgcc accatgcccg gctaattttt ctattttttgg tagagacggg gttttgccgt  10980
gttggtcagg ctggtcttga agtcctgacc tcagtgatcc actcgcctca gccgaagtgc  11040
tgcgattaca gacctgagcc actgcgccca gccttgatct tgaggtaaga gggtactgta  11100
cagcagttac tctatcataa cacctaaata atacctaaag ttaaagagtt ttgatgaagt  11160
tcttggcagc agtgcttttc cccttctgct ttccaaaagg aggtaaaaag aagccagtca  11220
atttcaaaaa cccctatcct gcttttattt tcagctacct tgaaagtgag ctgaatcacc  11280
atggaaatgt gcaaatgtga ggtttgcata cttggtttta agccctgagc accatatgct  11340
aatcaggcaa tcaggattct gtgcctccct gcagtcagtt gcatttctat ttaaaagtgc  11400
attttggttt ggaagcccct ttctggagcc taactaccaa aaggcagcaa cttttttgtat  11460
cattacaaag aaagctgtgt aagtgcactc ccaagcaaag gtgtggtagg agagtagcag  11520
ccacagagga cccaagccca agtcttggcc tgagttaagt tagtgctatt gctcccattg  11580
acgtgctatg atgtgaagcc gtttctggta cagtgttcct ttgctcagca ccttaaaagc  11640
ttggatttaa tagtaactgg gtaaccttaa tcagtagtca gaattatcaa cactttgctt  11700
tatttgacac aaccagactt tctcagttcc tgttctgtat ctagagcaac gtcttcatac  11760
tgtttttttca caaaattttt atttaaaaca gttgtgacag ccgaaggatt ttttttttt  11820
tttttacaaa attaaaatga aataacttgt acaactggtg cgtaccatgg ctccagccag  11880
atgcccaaag cactggctat taattcctgg agttcagatg gtcagttgag tctatcctag  11940
ttttttgctt cacttgttca atcatggaac tttctagaac gctgccactc ttcaaaggct  12000
tctcaatttc aaatttgaaa acttaattct ctccctctta gtttcaaagt tgttacagtg  12060
ttatctatgt gaagtatgtg gaaagttggg ggctggggat tttcctccag gcagattaag  12120
aaacagctct ccgggtcggg cgctgtggct caggcctgta atcccagcac tttgggaggc  12180
tgaggcagga ga                                                      12192
```

Human Mc1-1

Figure 16F

/translation="MEANGSQGTSGSANDSQHDPGKMFIGGLSWQTSPDSLRDYFSKF
GEIRECMVMRDPTTKRSRGFGFVTFADPASVDKVLGQPHHELDSKTIDPKVAFPRRAQ
PKMVTRTKKIFVGGLSANTVVEDVKQYFEQFGKVEDAMLMFDKTTNRHRGFGFVTFEN
EDVVEKVCEIHFHEINNKMVECKKAQPKEVMFPPGTRGRARGLPYTMDAFMLGMGMLG
YPNFVATYGRGYPGFAPSYGYQFPGFPAAAYGPVAAAAVAAARGSGSNPARPGGFPGA
NSPGPVADLYGPASQDSGVGNYISAASPQPGSGFGHGIAGPLIATAFTNGYH"

| | | | | | |
|---|---|---|---|---|---|
| ctcgccgctg | ccccggctcc | gccgctcgca | gagagattcg | gaggagcccg | ggcggggggg | 60 |
| aggaggaggg | ggaggaggga | gcggagatct | cggggctcgg | agccggccgc | cgctccgctc | 120 |
| cgatcgctgt | ggggcttggt | tttttggggg | tgggggggcg | gggggctca | gatatggagg | 180 |
| caaatgggag | ccaaggcacc | tcgggcagcg | ccaacgactc | cagcacgac | cccggtaaaa | 240 |
| tgtttatcgg | tggactgagc | tggcagacct | caccagatag | ccttagagac | tatttagca | 300 |
| aatttggaga | aattagagaa | tgtatggtca | tgagagatcc | cactacgaaa | cgctccagag | 360 |
| gcttcggttt | cgtcacgttc | gcagacccag | caagtgtaga | taaagtatta | ggtcagcccc | 420 |
| accatgagtt | agattccaag | acgattgacc | ccaaagttgc | atttcctcgt | cgagcgcaac | 480 |
| ccaagatggt | cacaagaaca | aagaaaatat | ttgtaggcgg | gttatctgcg | aacacagtag | 540 |
| tggaagatgt | aaagcaatat | ttcgagcagt | ttggcaaggt | ggaagatgca | atgctgatgt | 600 |
| ttgataaaac | taccaacagg | cacagagggt | ttggctttgt | cacttttgag | aatgaagatg | 660 |
| ttgtggagaa | agtctgtgag | attcatttcc | atgaaatcaa | taataaaatg | gtagaatgta | 720 |
| agaaagctca | gccgaaagaa | gtcatgttcc | cacctgggac | aagaggccgg | gcccggggac | 780 |
| tgccttacac | catggacgcg | ttcatgcttg | gcatggggat | gctggatat | ccaacttcg | 840 |
| tggcgaccta | tggccgtggc | taccccggat | ttgctccaag | ctatggctat | cagttcccag | 900 |
| gcttcccagc | agcggcttat | ggaccagtgg | cagcagcggc | ggtggcggca | gcaagaggat | 960 |
| caggctccaa | cccggcgcgg | cccggaggct | tcccgggggc | caacagccca | ggacctgtcg | 1020 |
| ccgatctcta | cggccctgcc | agccaggact | ccggagtggg | gaattacata | agtgcggcca | 1080 |
| gcccacagcc | gggctcgggc | ttcggccacg | gcatagctgg | acctttgatt | gcaacggcct | 1140 |
| ttacaaatgg | ataccattga | gcaggtgctt | tcgttgccat | ctcactctga | gcatacct | 1200 |
| ggatgtccag | gcaagactgg | gcgaagtttc | tgagtggccc | tttgtttagg | tgatgtcctc | 1260 |
| agacctggac | ccccaccagc | ctcactcccc | atcccaacca | gagatggctc | acttcggatc | 1320 |
| gagggttgac | tacatctcat | catctcacga | atctgctgta | atataagaca | acagctttta | 1380 |
| aatgtgtata | taaccatga | tttcggtttt | gttttgtttt | gttttcttg | atggtttccc | 1440 |
| tctccctccc | tctcttccca | ttctccttt | aaatctcttt | gaatcacatt | tggtagtgat | 1500 |
| tttgacttag | tccagtagtc | acatagcttt | aatatctagt | tcaaagctaa | ccatagtata | 1560 |
| attgttatat | taaggagtta | t | | | | 1581 |

Human Musashi 2     Figure 17

/translation="MSDVAIVKEGWLHKRGEYIKTWRPRYFLLKNDGTFIGYKERPQD
VDQREAPLNNFSVAQCQLMKTERPRPNTFIIRCLQWTTVIERTFHVETPEEREEWTTA
IQTVADGLKKQEEEEMDFRSGSPSDNSGAEEMEVSLAKPKHRVTMNEFEYLKLLGKGT
FGKVILVKEKATGRYYAMKILKKEVIVAKDEVAHTLTENRVLQNSRHPFLTALKYSFQ
THDRLCFVMEYANGGELFFHLSRERVFSEDRARFYGAEIVSALDYLHSEKNVVYRDLK
LENLMLDKDGHIKITDFGLCKEGIKDGATMKTFCGTPEYLAPEVLEDNDYGRAVDWWG
LGVVMYEMMCGRLPFYNQDHEKLFELILMEEIRFPRTLGPEAKSLLSGLLKKDPKQRL
GGGSEDAKEIMQHRFFAGIVWQHVYEKKLSPPFKPQVTSETDTRYFDEEFTAQMITIT
PPDQDDSMECVDSERRPHFPQFSYSASGTA"

Human AKT1

Figure 18

```
taattatggg tctgtaacca ccctggactg ggtgctcctc actgacggac ttgtctgaac    60
ctctctttgt ctccagcgcc cagcactggg cctggcaaaa cctgagacgc ccggtacatg   120
ttggccaaat gaatgaacca gattcagacc ggcaggggcg ctgtggttta ggaggggcct   180
ggggtttctc ccaggaggtt tttgggcttg cgctggaggg ctctggactc ccgtttgcgc   240
cagtggcctg catcctggtc ctgtcttcct catgtttgaa tttctttgct ttcctagtct   300
ggggagcagg gaggagccct gtgccctgtc ccaggatcca tgggtaggaa caccatggac   360
agggagagca acggggcca tctgtcacca ggggcttagg gaaggccgag ccagcctggg    420
tcaaagaagt caaaggggct gcctggagga ggcagcctgt cagctggtgc atcagaggct   480
gtggccaggc cagctgggct cggggagcgc cagcctgaga ggagcgcgtg agcgtcgcgg   540
gagcctcggg caccatgagc gacgtggcta ttgtgaagga gggttggctg cacaaacgag   600
gggagtacat caagacctgg cggccacgct acttcctcct caagaatgat ggcaccttca   660
ttggctacaa ggagcggccg caggatgtgg accaacgtga ggctcccctc aacaacttct   720
ctgtggcgca gtgccagctg atgaagacgg agcggccccg gcccaacacc ttcatcatcc   780
gctgcctgca gtggaccact gtcatcgaac gccttcca tgtggagact cctgaggagc    840
gggaggagtg gacaaccgcc atccagactg tggctgacgg cctcaagaag caggaggagg   900
aggagatgga cttccggtcg ggctcaccca gtgacaactc aggggctgaa gagatggagg   960
tgtccctggc caagcccaag caccgcgtga ccatgaacga gtttgagtac ctgaagctgc  1020
tgggcaaggg cactttcggc aaggtgatcc tggtgaagga gaaggccaca ggccgctact  1080
acgccatgaa gatcctcaag aaggaagtca tcgtggccaa ggacgaggtg gcccacacac  1140
tcaccgagaa ccgcgtcctg cagaactcca ggcacccctt cctcacagcc ctgaagtact  1200
ctttccagac ccacgaccgc ctctgctttg tcatggagta cgccaacggg ggcgagctgt  1260
tcttccacct gtcccgggag cgtgtgttct ccgaggaccg ggcccgcttc tatggcgctg  1320
agattgtgtc agccctggac tacctgcact cggagaagaa cgtggtgtac cgggacctca  1380
agctggagaa cctcatgctg gacaaggacg gcacattaa gatcacagac ttcgggctgt   1440
gcaaggaggg gatcaaggac ggtgccacca tgaagacctt ttgcggcaca cctgagtacc  1500
tggcccccga ggtgctggag acaatgact acggccgtgc agtggactgg tggggctgg    1560
gcgtggtcat gtacgagatg atgtgcggtc gcctgccctt ctacaaccag gaccatgaga  1620
agctttttga gctcatcctc atggaggaga tccgcttccc gcgcacgctt ggtcccgagg  1680
ccaagtcctt gctttcaggg ctgctcaaga aggaccccaa gcagaggctt ggcggggct   1740
ccgaggacgc caaggagatc atgcagcatc gcttctttgc cggtatcgtg tggcagcacg  1800
tgtacgagaa gaagctcagc ccaccttca gccccaggt cacgtcggag actgacacca    1860
ggtattttga tgaggagttc acggcccaga tgatcaccat cacaccacct gaccaagatg  1920
acagcatgga gtgtgtggac agcgagcgca gggccccactt ccccccagttc tcctactcgg 1980
ccagcggcac ggcctgaggc ggcggtggac tgcgctggac gatagcttgg agggatggag  2040
aggcggcctc gtgccatgat ctgtatttaa tggttttat ttctcgggtg catttgagag    2100
aagccacgct gtcctctcga gcccagatgg aaagacgttt ttgtgctgtg ggcagcaccc  2160
tccccgcag cggggtaggg aagaaaacta tcctgcgggt tttaattat ttcatccagt    2220
ttgttctccg ggtgtggcct cagccctcag aacaatccga ttcacgtagg gaaatgttaa  2280
ggacttctgc agctatgcgc aatgtggcat tggggggccg ggcaggtcct gcccatgtgt  2340
ccctcactc tgtcagccag ccgccctggg ctgtctgtca ccagctatct gtcatctctc    2400
tggggccctg ggcctcagtt caacctggtg caccagatg caacctcact atggtatgct    2460
ggccagcacc ctctcctggg ggtggcaggc acacagcagc cccccagcac taaggccgtg  2520
tctctgagga cgtcatcgga ggctgggccc ctgggatggg accagggatg gggatgggc   2580
cagggtttac ccagtgggac agaggagcaa ggtttaaatt tgttattgtg tattatgttg  2640
ttcaaatgca ttttgggggt ttttaatctt tgtgacagga agccctccc ccttcccctt    2700
ctgtgtcaca gttcttggtg actgtcccac cgggagcctc cccctcagat gatctctcca  2760
cggtagcact tgaccttttc gacgcttaac cttccgctg tcgcccagg ccctccctga    2820
ctccctgtgg gggtggccat ccctgggccc ctccacgcct cctggccaga cgctgccgct  2880
gccgctgcac cacggcgttt ttttacaaca ttcaacttta gtatttttac tattataata  2940
taatatggaa ccttccctcc aaattcttca ataaagttg cttttcaaaa aaaaaaaaa    3000
aaaaaaaa                                                            3008
```

Human AKT1             Figure 19

/translation="MKTERPRPNTFVIRCLQWTTVIERTFHVDSPDEREEWMRAIQMV
ANSLKQRAPGEDPMDYKCGSPSDSSTTEEMEVAVSKARAKVTMNDFDYLKLLGKGTFG
KVILVREKATGRYYAMKILRKEVIIAKDEVAHTVTESRVLQNTRHPFLTALKYAFQTH
DRLCFVMEYANGGELFFHLSRERVFTEERARFYGAEIVSALEYLHSRDVVYRDIKLEN
LMLDKDGHIKITDFGLCKEGISDGATMKTFCGTPEYLAPEVLEDNDYGRAVDWWGLGV
VMYEMMCGRLPFYNQDHERLFELILMEEIRFPRTLSPEAKSLLAGLLKKDPKQRLGGG
PSDAKEVMEHRFFLSINWQDVVQKKLLPPFKPQVTSEVDTRYFDDEFTAQSITITPPD
RYDSLGLLELDQRTHFPQFSYSASIRE"

Human AKT2

Figure 20

```
tgggaggggg cggtaagcgg gggctggggg gaggggggcgg gggggggccgc gccgtgctag   60
ccgtgggcc  tgcctcggag gaggcgtcgc cgccgccgct gccgctgccg gcgccgttgc   120
cgctgccggg  aaacacaagg aaagggaacc agcgcagcgt ggcgatgggc gggggtagag  180
ccccgccgga  gaggctgggc ggctgccggt gacagactgt gccctgtcca cggtgcctcc  240
tgcatgtcct  gctgccctga gctgtcccga gctaggtgac agcgtaccac gctgccacca  300
tgaatgaggt  gaatacatca agacctggag gccacggtac ttcctgctga agagcgacgg  360
ctccttcatt  gggtacaagg agaggcccga ggccctgat  cagactctac ccccttaaa   420
caacttctcc  gtagcagaat gccagctgat gaagaccgag aggccgcgac ccaacacctt  480
tgtcatacgc  tgcctgcagt ggaccacagt catcgagagg accttccacg tggattctcc  540
agacgagagg  gaggagtgga tgcgggccat ccagatggtc gccaacagcc tcaagcagcg  600
ggccccaggc  gaggacccca tggactacaa gtgtggctcc cccagtgact cctccacgac  660
tgaggagatg  gaagtggcgg tcagcaaggc acgggctaaa gtgaccatga atgacttcga  720
ctatctcaaa  ctccttggca agggaacctt tggcaaagtc atcctggtgc gggagaaggc  780
cactggccgc  tactacgcca tgaagatcct gcggaaggaa gtcatcattg ccaaggatga  840
agtcgctcac  acagtcaccg agagccgggt cctccagaac accaggcacc cgttcctcac  900
tgcgctgaag  tatgccttcc agacccacga ccgcctgtgc tttgtgatgg agtatgccaa  960
cgggggtgag  ctgttcttcc acctgtcccg ggagcgtgtc ttcacagagg agcgggcccg 1020
gttttatggt  gcagagattg tctcggctct tgagtacttg cactcgcggg acgtggtata 1080
ccgcgacatc  aagctggaaa acctcatgct ggacaaagat ggccacatca agatcactga 1140
ctttggcctc  tgcaaagagg gcatcagtga cggggccacc atgaaaacct tctgtgggac 1200
cccggagtac  ctggcgcctg aggtgctgga ggacaatgac tatggccggg ccgtggactg 1260
gtgggggctg  ggtgtggtca tgtacgagat gatgtgcggc cgcctgccct tctacaacca 1320
ggaccacgag  cgcctcttcg agctcatcct catggaagag atccgcttcc cgcgcacgct 1380
cagccccgag  gccaagtccc tgcttctggg gctgcttaag aaggacccca agcagaggct 1440
tggtgggggg  cccagcgatg ccaaggaggt catggagcac aggttcttcc tcagcatcaa 1500
ctggcaggac  gtggtccaga agaagctcct gccacccttc aaacctcagg tcacgtccga 1560
ggtcgacaca  aggtacttcg atgatgaatt taccgcccag tccatcacaa tcacacccc  1620
tgaccgctat  gacagcctgg gcttactgga gctggaccag cggacccact tccccagtt  1680
ctcctactcg  gccagcatcc gcgagtgagc agtctgccca gcagaggac  gcacgctcgc 1740
tgccatcacc  gctgggtggt ttttccccc  taacttttta cttagccttt ttggtttgtg 1800
tccccacccc  cacctcctca ccccctttcc agttcttctt caggcccctc ccagacgcac 1860
cccagcggcc  cctgcagccc ctgcctccag cctccagcct cacctttgtg cccagactcg 1920
catttggaag  actccacctc ccgcccaggc ctgggctgtt gggcggttgg agattcaggt 1980
tttaatccac  acaagcccca gtgaggggtg aagcatggcg cctggggcct gcctgagttt 2040
ctggcctggg  tgtcgtgctg gtgtctgcct ccgcgctgct gcatctggac gaaggctgcc 2100
ttctggtggg  acgcgacacc cggcagacag tggtgctgcc ttccaggccc cgtggcctag 2160
gctcggagtg  gccaggcacg gggcggtcca atcccccacc cgctgtcccc ctatgggggc 2220
agaaaagcaa  taatgtccag gggcaggcag gggcccttgg gagctgcagg gctggggtt  2280
agggctgctc  cctggtgaat ggagtcagat cctaggatct gtaccatggg gaaccaggag 2340
tggccgggct  gggtgccgcc tcctggtccg gcctcctccc caccaaactg tcctcaccct 2400
atggatgagg  caggaggaac atttggggcc aaacctgcct gcctccagc  ccgtgccttt 2460
actagggctt  ccttccagct ggccttacct cccgctggac cctgggcctg gcctggcccc 2520
actggggct   atgggctggg ctcaccctct cctctgcggg ggtggagggc caccagcctt 2580
ggctgttaca  atcttacacc ggacagtatt gggccccatg gacttggtca ggaggggtg  2640
ggggtgggca  tctctggtac ctattgggt  ggggggcctc tgaaaaggga ggctcctagg 2700
ccccccctcac  ccctccctct cccagggcc  ccacgttctg cagccttaag gttgaacatg 2760
agtgcacgtc  catgtcagtg ctgtgggact cctgtgcgtg cctcggactg cgtgtgtcgg 2820
cgggacgcag  gcacacgtgg gtgtgtgtgc atgtgtgttt gtgtgagggc agcgtgtcct 2880
```

Human AKT2    Figure 21A

```
ccagtgtgca tggtgtgtgg gcttgggccc catccctggc ccgagcattt catcctgtgg   2940
gggaggggtg ctgacctagt gggaggagcc ccactgtgat ccatgagctg ccctgcccac   3000
gcctcccctc cctgtagcaa cacctctggg tgtttggagt ttagcttttg tgggtttgct   3060
ctccctatcc catctcctgt actacacagt tcatggcagg gtggggaggg gtggggttgg   3120
ttcgggtggg tgagggtctt tttcctctgt gtgcgatgtt gttatctgac agttctccgt   3180
ccctactggc ctttctcctc gtcttcatat ttgtacggta caagcaataa agacactcat   3240
ttcagaccag ggcccagcct gcactcacgc cagcccaacc actctgggct ttgccttggt   3300
gatggagtca gaccctgggc cccagctcc tcctgtacta gccgttccct tcagcaagga   3360
gggcactgag ctcagggtga gggcagctgg ggtgtgtgca ggagctcagg ctggagaggg   3420
tgggtggagc tggtgctgtg gggctgaggg gtatgggaag ctccccgca tgtgggggtg   3480
gggtggacag agaccactcc aggccctcag tgctgcttag gctaagagag gtggggtgga   3540
gggacagggc tggaagatct gggtagccca gaatgaggag ggtgcctgtg ctgtcactga   3600
atgagaggga gtggttcatt ccacccggct gccgagcctc agagggggc attcctatcc   3660
tgccccacct ccctgtttat gctgccacct ggaagccttg aggcccccaa attccagtac   3720
agacccagtg gtgtgttcat ggtggcgtgg ttgctgtcac ctgggagctc ctgagcgttt   3780
ggttagaacc ctgttcagct tggggtcagc cctcccctag tcactgccct ttagcctgga   3840
tgtgtctggg ccctgcact tcccgtgctt gagtcacgtg gctgcatggc cgggcgctgg   3900
ccggatggaa cacctccccc agcaagggac cagggaccag agccctggcc tgccctgctg   3960
agccctgctg tgcagagggc ctggcacaga tgaatttgag attttgccgc aaggtgttag   4020
cacttcacac ccattgagtc tttgagattt taagtgaatg taagcagaaa aagtcagatc   4080
caatttacag aaatcagagt tagctacagc taggactcgt ttggttgggg tttttttagtt   4140
tgtctttcta aagtcatgtg gaccttaatt taattacaaa agtctaccct ggtggtcata   4200
aaataggcag gcctatgaag aaaggccttt tactcttcca tctcatccca gccccgagtt   4260
gacccacgtt gctgctcctc acaccatggt gatgcaggtc tcgtagtgtg ggcacaggcc   4320
tggctacctc atctttttag tgcctctctc ctcttccaca ggatgggggtc ccacagctgc   4380
agcagctggc ccgtagttg agcatgtgtg gttatcctgt agagcttttc ccaagaaggg   4440
tgtttgaact tagagtctta ataaaatctt accaaataaa ttttgagtag aataatcgtc   4500
ttttgcaatg tacatttaa aaatttcaca cattcttttt tgtatataaa gaacagtgac   4560
tgggcacagt ggctcatgcc tgtaatccca gcatttggg aggccgaggc gggcgggtct   4620
cttgaggcca ggggttcgag accagcctgg gcatcatagg gagaccttca tctctacaaa   4680
aaatacaaaa attagctggg catggtggtg catgcctgca atcccagcta acttggaagg   4740
ctgaggtgag gtgggaagat cacttgagcc caggagtttg aggctgcagt gagctatgat   4800
tgcggcactg cactgcagcc tgggacaatg agactgtgtc tctaaaaata aaaaaaaaaa   4860
aaacatgata catgctatta aaaagacag caaagcagga gtataagaaa ggaaattcac   4920
ccgaggtcgc agggccttga gtactcattt tggtgctgat tacctctctg caaatggaca   4980
cggcatcata aattggtagt ttcctgctct ttttgtgtaa tcttttccag ttaatgtgaa   5040
gcctctgggg gctgccctcg tgcactgatg gttgtgtgga gtcggggggcg gcagtgcgat   5100
tcccttttag ctgctgcatg gggggaactc aggctttcca gctgcttcct ggggttccat   5160
ggggtagacc cctcaaccgc ttcagctgcc ccgttaacag gaattgactt ggtttcgttt   5220
ggtgctacca gcagtcctgt aataaactag ctatccatct gtaaaaaaaa aaaaaaaaa    5280
```

Human AKT2                Figure 21B

```
/translation="MSGRPRTTSFAESCKPVQQPSAFGSMKVSRDKDGSKVTTVVATP
GQGPDRPQEVSYTDTKVIGNGSFGVVYQAKLCDSGELVAIKKVLQDKRFKNRELQIMR
KLDHCNIVRLRYFFYSSGEKKDEVYLNLVLDYVPETVYRVARHYSRAKQTLPVIYVKL
YMYQLFRSLAYIHSFGICHRDIKPQNLLLDPDTAVLKLCDFGSAKQLVRGEPNVSYIC
SRYYRAPELIFGATDYTSSIDVWSAGCVLAELLLGQPIFPGDSGVDQLVEIIKVLGTP
TREQIREMNPNYTEFKFPQIKAHPWTKDSSGTGHFTSGVRVFRPRTPPEAIALCSRLL
EYTPTARLTPLEACAHSFFDELRDPNVKLPNGRDTPALFNFTTQELSSNPPLATILIP
PHARIQAAASTPTNATAASDANTGDRGQTNNAASASASNST"
```

Human GSK-3$\beta$

Figure 22

```
cgggcttgtg ccgccgccgc cgccgccgcc gcccgggcca agtgacaaag gaaggaagga    60
agcgaggagg agccggcccc gcagccgctg acagggctct gggctggggc aaagcgcgga   120
cacttcctga gcgggcaccg agcagagccg aggggcggga gggcggccga gctgttgccg   180
cggacggggg aggggccccc gagggacgga agcggttgcc gggttcccat gtccccggcg   240
aatggggaac agtcgaggag ccgctgcctg gggtctgaag ggagctgcct ccgccaccgc   300
catggccgct ggatccagcc gccgcctgca gctgctcctg gcgcaatgag gagaggagcc   360
gccgccaccg ccaccgcccg cctctgactg actcgcgact ccgccgccct ctagttcgcc   420
gggcccctgc cgtcagcccg ccggatcccg cggcttgccg gagctgcagc gtttcccgtc   480
gcatctccga gccaccccct ccctccctct ccctccctcc tacccatccc cctttctctt   540
caagcgtgag actcgtgatc cttccgccgc ttcccttctt cattgactcg gaaaaaaat   600
ccccgaggaa aatataatat tcgaagtact cattttcaat caagtatttg ccccgtttc   660
acgtgataca tatttttttta ggatttgccc tctctttct ctcctcccag gaagggagg   720
ggaaagaatt gtatttttc ccaagtccta aatcatctat atgttaaata tccgtgccga   780
tctgtcttga aggagaaata tatcgcttgt tttgtttttt atagtataca aaggagtga   840
aaagccaaga ggacgaagtc ttttcttt tcttctgtgg gagaacttaa tgctgcattt   900
atcgttaacc taacacccca acataaagac aaaaggaaga aaaggaggaa ggaaggaaaa   960
ggtgattcgc gaagagagtg atcatgtcag ggcggcccag aaccacctcc tttgcggaga  1020
gctgcaagcc ggtgcagcag ccttcagctt ttggcagcat gaaagttagc agagacaagg  1080
acggcagcaa ggtgacaaca gtggtggcaa ctcctgggca gggtccagac aggccacaag  1140
aagtcagcta tacagacact aaagtgattg gaaatggatc atttggtgtg gtatatcaag  1200
ccaaactttg tgattcagga gaactggtcg ccatcaagaa agtattgcag acaagagat  1260
ttaagaatcg agagctccag atcatgagaa agctagatca ctgtaacata gtccgattgc  1320
gttatttctt ctactccagt ggtgagaaga agatgaggt ctatcttaat ctggtgctgg  1380
actatgttcc ggaaacagta tacagagttg ccagacacta gtcgagcc aaacagacgc  1440
tccctgtgat ttatgtcaag ttgtatatgt atcagctgtt ccgaagttta gcctatatcc  1500
attcctttgg aatctgccat cgggatatta accgcagaa cctcttgttg gatcctgata  1560
ctgctgtatt aaaactctgt gactttggaa gtgcaaagca gctggtccga ggagaaccca  1620
atgtttcgta tatctgttct cggtactata gggcaccaga gttgatcttt ggagccactg  1680
attataccct tagtatagat gtatggtctg ctggctgtgt gttggctgag ctgttactag  1740
gacaaccaat atttccaggg gatagtggtg tggatcagtt ggtagaaata atcaaggtcc  1800
tgggaactcc aacaagggag caaatcagag aaatgaaccc aaactacaca gaatttaaat  1860
tccctcaaat taaggcacat ccttggacta aggattcgtc aggaacagga catttcacct  1920
caggagtgcg ggtcttccga ccccgaactc caccggaggc aattgcactg tgtagccgtc  1980
tgctggagta tacaccaact gcccgactaa caccactgga agcttgtgca cattcatttt  2040
ttgatgaatt acgggaccca aatgtcaaac taccaaatgg gcgagacaca cctgcactct  2100
tcaacttcac cactcaagaa ctgtcaagta atccacctct ggctaccatc cttattcctc  2160
ctcatgctcg gattcaagca gctgcttcaa cccccacaaa tgccacagca gcgtcagatg  2220
ctaatactgg agaccgtgga cagaccaata atgctgcttc tgcatcagct ccaactcca  2280
cctgaacagt cccgagcagc cagctgcaca ggaaaaacca ccagttactt gagtgtcact  2340
cagcaacact ggtcacgttt ggaaagaata ttaaaagag aaaaaatcc tgttcatttt  2400
agtgttcaat tttttatta ttattgttgt tcttatttaa ccttgtaaaa tatctataaa  2460
tacaaaccaa tttcattgta ttctcacttt gagggagatc caggggtgg gagggttgt  2520
ggggagggg aaagcggagc actagaacat acaatctctc tcccacgaca atctttttt  2580
attaaaagtc tgctgttgta tactttaaaa acaggactcc tgcctcatgc cccttccaca  2640
aaagaagaaa acctttttct gtgctgatgg gtttttttga actttgtttt cttttaaagt  2700
ctagtgtgag actttggtat agtgcacagc ttgaaattgg ttgggagctt agcaggtata  2760
actcaacggg gacttaaatg tcacttgtaa aattaatcca tatcttcggg tatttataga  2820
cttgcctttg gcatgttggt ggcaggtgtg gcagacaaag aaatgtgtat cattcgtaac  2880
ccagggaggt caataaagtt tggaactcta cagggaagat tcttagtaga tttgttaagg  2940
ttttgttttg ctctcagtta gtgctagtga tgtagaggct tgtacaggag gctgccagag  3000
gggaagcagc aagcaagact caggcacaca tgctctacag gtggctcttt gtttgcctga  3060
```

Human GSK-3β

Figure 23A

```
ccaaagttct ttgcaaatct tagcacagtt tcaaactagt gacctgggag gagatggaag    3120
gggtgttgag caggctgagc tagctgctga ggtcaaaggc tgatgagccc agaggaaggg    3180
gacaggtcag ggatacatct caccactgtg aataagtttg tccagatttt tttctaaagt    3240
tacttccctt ggaaagatac acttgagagg acattgtagt taaataatgt gaactgtaac    3300
agtcatctac tggtttatt ttcatatttt ttaattgaaa attgagcttg cagaaatagc    3360
cacattctac acatagttct aattttaaat ccaaatctag aatctgtatt taatttgttt    3420
tttaacctca tgcttttac atttatttat tgatgcatgt cagatggtag aaatattaaa    3480
aactacacat cagaatgata cagtcactta tacctgctga ctttatagga aagctgatga    3540
tataaatgtg tgtatatatg ttatatatac atatattcaa tactgccttt ttttttgtct    3600
acagtatcaa aattgactgg ttgaagcatg agaagaatgt ttcccccaca cccagttaag    3660
agtttttgtg tctgttttct ttgtgtatca gtgaacgatg ttaagaatca gtctctcttt    3720
ttgaagaaaa agcaatattc cttggaaagc aaggagaatt gaaggactat gtttgccgtg    3780
aggaaataga ttttcatgac tagtttgttt tatactttta aggttggcat ctatgtgggc    3840
cttatatact ctaaaatgaa ctttagtcac cttggtgctt atgggccatt acttgaccta    3900
tgaatcttta aggcacaatc agttgtactt tacatttaaa gatcacttga gtgatggccg    3960
cctttccctc ctacccgctc cttccccaca tgccttccaa ggttagctgg taactgtagg    4020
gctgcagagc tgagcccatg gttgtgtgta acttgccctc accctcctca ttgccacctt    4080
aggtcacttt atgggtctcg tcctccagag ggttcggaag tggagtctgt tggcagccct    4140
cctgcaggcc ctagcaccct gtcctgctcc ttaactgtgt gtgtgactct caagagagt    4200
tgtcctgcct gctgaagtga accagtaccc agaaagacaa ctgtgagcca tcttggtttt    4260
cactcgctgt ttagctgagg tcttgggcca caaaaggggt ttcacaaacc tctggatata    4320
tcagagttta tgagaaagga aacatgctca gtcaaaccaa atcaaacaaa ttgaatttta    4380
tgttttataa agtgcttctg aaagctaaga tttgaaagaa gtctgaaatc aaagtatttg    4440
gcagcataac tccttaaagg tagtggcgtt gatagaccat tttcagacag aatttataaa    4500
gaatctgaaa aggcaggtct gtgatagaga aatggacctg cattcagatc caactgccca    4560
gcaagcgttt ggatgcagac actgctctgg acgtggtata ctccccagag tccataaaaa    4620
tcagtgctta ttttaggaaa caggttgccc cccacaactg gggtaaaaga agagagaaaa    4680
gtcacgcttt tctctcattt cattgtgtgt gcatgtgtgc gtgtgtgtgt gtgtgtgtgt    4740
gtgctgagat gtgtgatttt tctttctcaa ggatcatggt gggatcacag aactctttta    4800
tacaagtgag atccaggtct ctgaatatct ttttgtatat aataataata aaaagctcct    4860
caccaaattc aagcttgtac attatatttt ctttctgtgt ttttaaattt aagttttatt    4920
gtttttgtatg taaatatgtg gacccaggaa ctgttattaa tgagcaaaaa gttactgttc    4980
agggcagtga ttctgtttaa taatcagaca aaatgtagac gagcttttta aagccatata    5040
gttttaactc tgtacagtag gtaccggcct gtattattgt aacaataact ctagcaatgt    5100
atagtgtatc tatatagttt ggagtgcctt cgcttccatg tgttttttt tttaatttgt    5160
tctttttaa attttaattg gtttccttta tccatgtctc cctgtccacc ccctttccct    5220
ttgaaataat aactcactca taacagtatc tttgcccctt ccacagttaa gtttcagtga    5280
taccatactc aggagtggga agaggaaatc atattcgtaa tttcatttcg ttgaagccct    5340
gcctttgttt tggttctgaa tgtctttcct cctcggtagc agtgagaccg gtttcatttc    5400
```

Human GSK-3β

Figure 23B

```
atacttagtc cattcaggga cttagtgtag caccagggag ccctagagct ggaggatatc   5460
gaatagatta aattttgctc gtctcttcca caagccctaa ccatgggtct taaaaacagc   5520
agattctggg agccttccat gctctctctc tctcctcttt tatctacttc cctcccaaat   5580
gagagagtga cagagaattg ttttttata aatcgaagtt tcttaatagt atcaggtttt   5640
gatacgtcag tggtctaaaa tgctatagtg caattactag cagttactgc acggagtgcc   5700
accgtgccaa tagaggactg ttgttttaac aagggaactc ttagcccatt tcctccctcc   5760
cgccatctct acccttgctc aatgaaatat cattttaatt tcttttaaaa aaaatcagtt   5820
taattcttac tgtgtgccca acacgaaggc cttttttgaa agaaaaatag aatgttttgc   5880
ctcaaagtag tccatataaa atgtcttgaa tagaagaaaa aactaccaaa ccaaaggtta   5940
ctattttga aacatcgtgt gttcattcca gcaaggcaga agactgcacc ttctttccag   6000
tgacatgctg tgtcattttt tttaagtcct cttaattttt agacacattt ttggtttatg   6060
ttttaacaat gtatgcctaa ccagtcatct tgtctgcacc aatgcaaagg tttctgagag   6120
gagtattctc tatccctgtg gatatgaaga cactggcatt tcatctattt ttccctttcc   6180
tttttaaagg atttaacttt ggaatcttcc aaaggaagtt tggccaatgc cagatcccca   6240
ggaatttggg gggttttctt tcttttcaac tgaaattgta tctgattcct actgttcatg   6300
ttagtgatca tctaatcaca gagccaaaca cttttctccc ctgtgtggaa aagtaggtat   6360
gctttacaat aaaatctgtc ttttctggta gaaacctgag ccactgaaaa taaaagagac   6420
aactagaagc acagtagagt cccagactga gatctacctt tgagaggctt tgaaagtaat   6480
ccctggggtt tggattattt tcacaagggt tatgccgttt tattcaagtt tgttgctccg   6540
ttttgcacct ctgcaataaa agcaaaatga caaccagtac ataaggggtt agcttgacaa   6600
agtagacttc cttgtgttaa ttttaagtt tttttttcct taactatatc tgtctacagg   6660
cagatacaga tagttgtatg aaaatctgct tgcctgtaaa atttgcattt ataaatgtgt   6720
tgccgatgga tcacttgggc ctgtacacat accaattagc gtgaccactt ccatcttaaa   6780
aacaaaccta aaaaacaaaa tttattatat atatatatat atatatataa aggactgtgg   6840
gttgtataca aactattgca aacacttgtg caaatctgtc ttgatataaa ggaaaagcaa   6900
aatctgtata acattattac tacttgaatg cctctgtgac tgattttttt ttcatttta   6960
atataaactt ttttgtgaaa agtatgctca atgttttttt tccctttccc cattccctg   7020
taaatacatt ttgttctatg tgacttggtt tggaaatagt taactggtac tgtaatttgc   7080
attaaataaa aagtaggtta gcctggaaat gaaattaaaa aaaaaaaaaa aaaa          7134
```

Human GSK-3β

Figure 23C

/translation="MTAIIKEIVSRNKRRYQEDGFDLDLTYIYPNIIAMGFPAERLEG
VYRNNIDDVVRFLDSKHKNHYKIYNLCAERHYDTAKFNCRVAQYPFEDHNPPQLELIK
PFCEDLDQWLSEDDNHVAAIHCKAGKGRTGVMICAYLLHRGKFLKAQEALDFYGEVRT
RDKKGVTIPSQRRYVYYYSYLLKNHLDYRPVALLFHKMMFETIPMFSGGTCNPQFVVC
QLKVKIYSSNSGPTRREDKFMYFEFPQPLPVCGDIKVEFFHKQNKMLKKDKMFHFWVN
TFFIPGPEETSEKVENGSLCDQEIDSICSIERADNDKEYLVLTLTKNDLDKANKDKAN
RYFSPNFKVKLYFTKTVEEPSNPEASSSTSVTPDVSDNEPDHYRYSDTTDSDPENEPF
DEDQHTQITKV"

Human PTEN

Figure 24

```
cctcccctcg  cccggcgcgg  tcccgtccgc  ctctcgctcg  cctcccgcct  cccctcggtc   60
ttccgaggcg  cccgggctcc  cggcgcggcg  gcggaggggg  cgggcaggcc  ggcgggcggt  120
gatgtggcgg  gactctttat  gcgctgcggc  aggatacgcg  ctcggcgctg  ggacgcgact  180
gcgctcagtt  ctctcctctc  ggaagctgca  gccatgatgg  aagtttgaga  gttgagccgc  240
tgtgaggcga  ggccgggctc  aggcgaggga  gatgagagac  ggcggcggcc  gcggcccgga  300
gccoctctca  gcgcctgtga  gcagccgcgg  gggcagcgcc  ctcggggagc  cggccggcct  360
gcggcggcgg  cagcggcggc  gtttctcgcc  tcctcttcgt  cttttctaac  cgtgcagcct  420
cttcctcggc  ttctcctgaa  agggaaggtg  gaagccgtgg  gctcgggcgg  gagccggctg  480
aggcgcggcg  gcggcggcgg  cacctcccgc  tcctggagcg  gggggagaa   gcggcggcgg  540
cggcggccgc  ggcggctgca  gctccaggga  ggggtctga   gtcgcctgtc  accatttcca  600
gggctgggaa  cgccggagag  ttggtctctc  cccttctact  gcctccaaca  cggcggcggc  660
ggcggcggca  catccaggga  cccgggccgg  ttttaaacct  cccgtccgcc  gccgccgcac  720
```

Human PTEN

Figure 25A

| | | | | | | |
|---|---|---|---|---|---|---|
|cccccgtggc|ccgggctccg|gaggccgccg|gcggaggcag|ccgttcggag|gattattcgt|780|
|cttctcccca|ttccgctgcc|gccgctgcca|ggcctctggc|tgctgaggag|aagcaggccc|840|
|agtcgctgca|accatccagc|agccgccgca|gcagccatta|cccggctgcg|gtccagagcc|900|
|aagcggcggc|agagcgaggg|gcatcagcta|ccgccaagtc|cagagccatt|tccatcctgc|960|
|agaagaagcc|ccgccaccag|cagcttctgc|catctctctc|ctccttttc|ttcagccaca|1020|
|ggctcccaga|catgacagcc|atcatcaaag|agatcgttag|cagaaacaaa|aggagatatc|1080|
|aagaggatgg|attcgactta|gacttgacct|atatttatcc|aaacattatt|gctatgggat|1140|
|ttcctgcaga|aagacttgaa|ggcgtataca|ggaacaatat|tgatgatgta|gtaaggtttt|1200|
|tggattcaaa|gcataaaaac|cattacaaga|tatacaatct|ttgtgctgaa|agacattatg|1260|
|acaccgccaa|atttaattgc|agagttgcac|aatatccttt|tgaagaccat|aacccaccac|1320|
|agctagaact|tatcaaaccc|ttttgtgaag|atcttgacca|atggctaagt|gaagatgaca|1380|
|atcatgttgc|agcaattcac|tgtaaagctg|gaaagggacg|aactggtgta|atgatatgtg|1440|
|catatttatt|acatcggggc|aaattttaa|aggcacaaga|ggccctagat|ttctatgggg|1500|
|aagtaaggac|cagagacaaa|aagggagtaa|ctattcccag|tcagaggcgc|tatgtgtatt|1560|
|attatagcta|cctgttaaag|aatcatctgg|attatagacc|agtggcactg|ttgtttcaca|1620|
|agatgatgtt|tgaaactatt|ccaatgttca|gtggcggaac|ttgcaatcct|cagtttgtgg|1680|
|tctgccagct|aaaggtgaag|atatattcct|ccaattcagg|acccacacga|cgggaagaca|1740|
|agttcatgta|ctttgagttc|cctcagccgt|tacctgtgtg|tggtgatatc|aaagtagagt|1800|
|tcttccacaa|acagaacaag|atgctaaaaa|aggacaaaat|gtttcacttt|tgggtaaata|1860|
|cattcttcat|accaggacca|gaggaaacct|cagaaaaagt|agaaaatgga|agtctatgtg|1920|
|atcaagaaat|cgatagcatt|tgcagtatag|agcgtgcaga|taatgacaag|gaatatctag|1980|
|tacttacttt|aacaaaaaat|gatcttgaca|aagcaaataa|agacaaagcc|aaccgatact|2040|
|tttctccaaa|ttttaaggtg|aagctgtact|tcacaaaaac|agtagaggag|ccgtcaaatc|2100|
|cagaggctag|cagttcaact|tctgtaacac|cagatgttag|tgacaatgaa|cctgatcatt|2160|
|atagatattc|tgacaccact|gactctgatc|cagagaatga|accttttgat|gaagatcagc|2220|
|atacacaaat|tacaaaagtc|tgaattttt|tttatcaaga|gggataaaac|accatgaaaa|2280|
|taaacttgaa|taaactgaaa|atggacctt|ttttttaa|tggcaatagg|acattgtgtc|2340|
|agattaccag|ttataggaac|aattctcttt|tcctgaccaa|tcttgtttta|ccctatacat|2400|
|ccacagggtt|ttgacacttg|ttgtccagtt|gaaaaaaggt|tgtgtagctg|tgtcatgtat|2460|
|ataccttttt|gtgtcaaaag|gacatttaaa|attcaattag|gattaataaa|gatggcactt|2520|
|tcccgtttta|ttccagtttt|ataaaaagtg|gagacagact|gatgtgtata|cgtaggaatt|2580|
|ttttccttt|gtgttctgtc|accaactgaa|gtggctaaag|agctttgtga|tatactggtt|2640|
|cacatcctac|ccctttgcac|ttgtggcaac|agataagttt|gcagttggct|aagagaggtt|2700|
|tccgaagggt|tttgctacat|tctaatgcat|gtattcgggt|taggggaatg|gagggaatgc|2760|

Human PTEN            Figure 25B

```
tcagaaagga aataatttta tgctggactc tggaccatat accatctcca gctatttaca 2820
cacaccttc  tttagcatgc tacagttatt aatctggaca ttcgaggaat tggccgctgt 2880
cactgcttgt tgtttgcgca ttttttttta aagcatattg gtgctagaaa aggcagctaa 2940
aggaagtgaa tctgtattgg ggtacaggaa tgaaccttct gcaacatctt aagatccaca 3000
aatgaaggga tataaaaata atgtcatagg taagaaacac agcaacaatg acttaaccat 3060
ataaatgtgg aggctatcaa caaagaatgg gcttgaaaca ttataaaaat tgacaatgat 3120
ttattaaata tgttttctca attgtaacga cttctccatc tcctgtgtaa tcaaggccag 3180
tgctaaaatt cagatgctgt tagtacctac atcagtcaac aacttacact tattttacta 3240
gttttcaatc ataatacctg ctgtggatgc ttcatgtgct gcctgcaagc ttctttttc  3300
tcattaaata taaaatattt tgtaatgctg cacagaaatt ttcaatttga gattctacag 3360
taagcgtttt ttttctttga agatttatga tgcacttatt caatagctgt cagccgttcc 3420
accctttga  ccttacacat tctattacaa tgaatttgc  agttttgcac attttttaaa 3480
tgtcattaac tgttagggaa ttttacttga atactgaata catataatgt ttatattaaa 3540
aaggacattt gtgttaaaaa ggaaattaga gttgcagtaa actttcaatg ctgcacacaa 3600
aaaaaagaca tttgattttt cagtagaaat tgtcctacat gtgctttatt gatttgctat 3660
tgaaagaata gggttttttt tttttttttt tttttttttt ttaaatgtgc agtgttgaat 3720
catttcttca tagtgctccc ccgagttggg actagggctt caatttcact tcttaaaaaa 3780
aatcatcata tatttgatat gcccagactg catacgattt taagcggagt acaactacta 3840
ttgtaaagct aatgtgaaga tattattaaa aaggttttt  tttccagaaa tttggtgtct 3900
tcaaattata ccttcacctt gacatttgaa tatccagcca ttttgtttct taatggtata 3960
aaattccatt ttcaataact tattggtgct gaaattgttc actagctgtg gtctgaccta 4020
gttaatttac aaatacagat tgaataggac ctactagagc agcatttata gagtttgatg 4080
gcaaatagat taggcagaac ttcatctaaa atattcttag taaataatgt tgacacgttt 4140
tccataccct gtcagtttca ttcaacaatt tttaaatttt taacaaagct cttaggattt 4200
acacatttat atttaaacat tgatatatag agtattgatt gattgctcat aagttaaatt 4260
ggtaaagtta gagacaacta ttctaacacc tcaccattga aatttatatg ccaccttgtc 4320
tttcataaaa gctgaaaatt gttacctaaa atgaaaatca acttcatgtt ttgaagatag 4380
ttataaatat tgttctttgt tacaatttcg ggcaccgcat attaaaacgt aactttattg 4440
ttccaatatg taacatggag ggccaggtca taaataatga cattataatg ggcttttgca 4500
ctgttattat ttttcctttg gaatgtgaag gtctgaatga gggttttgat tttgaatgtt 4560
tcaatgtttt tgagaagcct tgcttacatt ttatggtgta gtcattggaa atggaaaaat 4620
ggcattatat atattatata tataaatata tattatacat actctcctta ctttatttca 4680
gttaccatcc ccatagaatt tgacaagaat tgctatgact gaaaggtttt cgagtcctaa 4740
ttaaaacttt atttatggca gtattcataa ttagcctgaa atgcattctg taggtaatct 4800
ctgagttct  ggaatatttt cttagacttt ttggatgtgc agcagcttac atgtctgaag 4860
ttacttgaag gcatcacttt taagaaagct tacagttggg ccctgtacca tcccaagtcc 4920
tttgtagctc ctcttgaaca tgtttgccat acttttaaaa gggtagttga ataaatagca 4980
tcaccattct ttgctgtggc acaggttata aacttaagtg gagtttaccg gcagcatcaa 5040
atgtttcagc tttaaaaaat aaaagtaggg tacaagttta atgtttagtt ctagaaattt 5100
tgtgcaatat gttcataacg atggctgtgg ttgccacaaa gtgcctcgtt tacctttaaa 5160
tactgttaat gtgtcatgca tgcagatgga aggggtggaa ctgtgcacta aagtggggc  5220
tttaactgta gtatttggca gagttgcctt ctacctgcca gttcaaaagt tcaacctgtt 5280
ttcatataga atatatatac taaaaatttt cagtctgtta aacagcctta ctctgattca 5340
gcctcttcag atactcttgt gctgtgcagc agtggctctg tgtgtaaatg ctatgcactg 5400
aggatacaca aaaataccaa tatgatgtgt acaggataat gcctcatccc aatcagatgt 5460
ccatttgtta ttgtgtttgt taacaaccct ttatctctta gtgttataaa ctccacttaa 5520
aactgattaa agtctcattc ttgtcaaaaa aaaaaaaaaa aaaaaaaaaa aa          5572
```

Human PTEN  Figure 25C

/translation="MAGLPRRIIKETQRLLAEPVPGIKAEPDESNARYFHVVIAGPQD
SPFEGGTFKLELFLPEEYPMAAPKVRFMTKIYHPNVDKLGRICLDILKDKWSPALQIR
TVLLSIQALLSAPNPDDPLANDVAEQWKTNEAQAIETARAWTRLYAMNNI"

```
gtcccccgga agtggagccc gggacttcca ctcgtgcgtg aggcgagagg agccggagac      60
gagaccagag gccgaactcg ggttctgaca agatggccgg gctgccccgc aggatcatca     120
aggaaaccca gcgtttgctg gcagaaccag ttcctggcat caaagccgaa ccagatgaga     180
gcaacgcccg ttatttcat gtggtcattg ctggccctca ggattccccc tttgagggag      240
ggacttttaa acttgaacta ttccttccag aagaataccc aatggcagcc cctaaagtac     300
gtttcatgac caaaatttat catcctaatg tagacaagtt gggaagaata tgtttagata     360
ttttgaaaga taagtggtcc ccagcactgc agatccgcac agttctgcta tcgatccagg     420
ccttgttaag tgctcccaat ccagatgatc cattagcaaa tgatgtagcg gagcagtgga     480
agaccaacga agcccaagcc atagaaacag ctagagcatg gactaggcta tatgccatga     540
ataatattta aattgatacg atcatcaagt gtgcatcact ctcctgttc tgccaagact       600
tcctcctctt tgtttgcatt taatggacac agtcttagaa acattacaga ataaaaaagc     660
ccagacatct tcagtccttt ggtgattaaa tgcacattag caaatctatg tcttgtcctg     720
attcactgtc ataaagcatg agcagaggct agaagtatca tctggattgt tgtgaaacgt     780
ttaaaagcag tggcccctcc ctgctttat tcatttcccc catcctggtt taagtataaa      840
gcactgtgaa tgaaggtagt tgtcaggtta gctgcagggg tgtgggtgtt tttatttat     900
tttatttat tttatttttg aggggggagg tagtttaatt ttatgggctc ctttcccct     960
tttttggtga tctaattgca ttggttaaaa gcagctaacc aggtctttag aatatgctct    1020
agccaagtct aactttattt agacgctgta gatggacaag cttgattgtt ggaaccaaaa    1080
tgggaacatt aaacaaacat cacagccctc actaataaca ttgctgtcaa gtgtagattc    1140
cccccttcaa aaaaagcttg tgaccatttt gtatggcttg tctggaaact tctgtaaatc    1200
ttatgttta gtaaatatt ttttgttatt ctaaaaaaaa aaaaaaaaaa                  1250
```

Human UBC 13

Figure 26

SEQUENCE LISTING

```
<160> NUMBER OF SEQ ID NOS: 23

<210> SEQ ID NO 1
<211> LENGTH: 703
<212> TYPE: PRT
<213> ORGANISM: Homo sapiens

<400> SEQUENCE: 1

Met Ala Ala Ala Thr Gly Asp Pro Gly Leu Ser Lys Leu Gln Phe Ala
1               5                   10                  15

Pro Phe Ser Ser Ala Leu Asp Val Gly Phe Trp His Glu Leu Thr Gln
            20                  25                  30

Lys Lys Leu Asn Glu Tyr Arg Leu Asp Glu Ala Pro Lys Asp Ile Lys
```

```
                35                  40                  45
Gly Tyr Tyr Tyr Asn Gly Asp Ser Ala Gly Leu Pro Ala Arg Leu Thr
 50                  55                  60

Leu Glu Phe Ser Ala Phe Asp Met Ser Ala Pro Thr Pro Ala Arg Cys
 65                  70                  75                  80

Cys Pro Ala Ile Gly Thr Leu Tyr Asn Thr Asn Leu Glu Ser Phe
                 85                  90                  95

Lys Thr Ala Asp Lys Lys Leu Leu Glu Gln Ala Ala Asn Glu Ile
                100                 105                 110

Trp Glu Ser Ile Lys Ser Gly Thr Ala Leu Glu Asn Pro Val Leu Leu
                115                 120                 125

Asn Lys Phe Leu Leu Leu Thr Phe Ala Asp Leu Lys Lys Tyr His Phe
130                 135                 140

Tyr Tyr Trp Phe Cys Tyr Pro Ala Leu Cys Leu Pro Glu Ser Leu Pro
145                 150                 155                 160

Leu Ile Gln Gly Pro Val Gly Leu Asp Gln Arg Phe Ser Leu Lys Gln
                165                 170                 175

Ile Glu Ala Leu Glu Cys Ala Tyr Asp Asn Leu Cys Gln Thr Glu Gly
                180                 185                 190

Val Thr Ala Leu Pro Tyr Phe Leu Ile Lys Tyr Asp Glu Asn Met Val
                195                 200                 205

Leu Val Ser Leu Leu Lys His Tyr Ser Asp Phe Phe Gln Gly Gln Arg
210                 215                 220

Thr Lys Ile Thr Ile Gly Val Tyr Asp Pro Cys Asn Leu Ala Gln Tyr
225                 230                 235                 240

Pro Gly Trp Pro Leu Arg Asn Phe Leu Val Leu Ala Ala His Arg Trp
                245                 250                 255

Ser Ser Ser Phe Gln Ser Val Glu Val Val Cys Phe Arg Asp Arg Thr
                260                 265                 270

Met Gln Gly Ala Arg Asp Val Ala His Ser Ile Ile Phe Glu Val Lys
                275                 280                 285

Leu Pro Glu Met Ala Phe Ser Pro Asp Cys Pro Lys Ala Val Gly Trp
290                 295                 300

Glu Lys Asn Gln Lys Gly Gly Met Gly Pro Arg Met Val Asn Leu Ser
305                 310                 315                 320

Glu Cys Met Asp Pro Lys Arg Leu Ala Glu Ser Ser Val Asp Leu Asn
                325                 330                 335

Leu Lys Leu Met Cys Trp Arg Leu Val Pro Thr Leu Asp Leu Asp Lys
                340                 345                 350

Val Val Ser Val Lys Cys Leu Leu Leu Gly Ala Gly Thr Leu Gly Cys
                355                 360                 365

Asn Val Ala Arg Thr Leu Met Gly Trp Gly Val Arg His Ile Thr Phe
370                 375                 380

Val Asp Asn Ala Lys Ile Ser Tyr Ser Asn Pro Val Arg Gln Pro Leu
385                 390                 395                 400

Tyr Glu Phe Glu Asp Cys Leu Gly Gly Gly Lys Pro Lys Ala Leu Ala
                405                 410                 415

Ala Ala Asp Arg Leu Gln Lys Ile Phe Pro Gly Val Asn Ala Arg Gly
                420                 425                 430

Phe Asn Met Ser Ile Pro Met Pro Gly His Pro Val Asn Phe Ser Ser
                435                 440                 445

Val Thr Leu Glu Gln Ala Arg Arg Asp Val Glu Gln Leu Glu Gln Leu
                450                 455                 460
```

| | | | | | | | | | | | | |
|---|---|---|---|---|---|---|---|---|---|---|---|---|
|Ile|Glu|Ser|His|Asp|Val|Val|Phe|Leu|Leu|Met|Asp|Thr|Arg|Glu|Ser|
|465| | | | |470| | | |475| | | | |480|

Ile Glu Ser His Asp Val Val Phe Leu Leu Met Asp Thr Arg Glu Ser
465                 470             475                 480

Arg Trp Leu Pro Ala Val Ile Ala Ala Ser Lys Arg Lys Leu Val Ile
            485                 490                 495

Asn Ala Ala Leu Gly Phe Asp Thr Phe Val Val Met Arg His Gly Leu
                500                 505             510

Lys Lys Pro Lys Gln Gln Gly Ala Gly Asp Leu Cys Pro Asn His Pro
            515                 520             525

Val Ala Ser Ala Asp Leu Leu Gly Ser Ser Leu Phe Ala Asn Ile Pro
530                 535             540

Gly Tyr Lys Leu Gly Cys Tyr Phe Cys Asn Asp Val Val Ala Pro Gly
545                 550             555                 560

Asp Ser Thr Arg Asp Arg Thr Leu Asp Gln Gln Cys Thr Val Ser Arg
                565             570             575

Pro Gly Leu Ala Val Ile Ala Gly Ala Leu Ala Val Glu Leu Met Val
            580             585             590

Ser Val Leu Gln His Pro Glu Gly Gly Tyr Ala Ile Ala Ser Ser Ser
            595             600             605

Asp Asp Arg Met Asn Glu Pro Pro Thr Ser Leu Gly Leu Val Pro His
610                 615             620

Gln Ile Arg Gly Phe Leu Ser Arg Phe Asp Asn Val Leu Pro Val Ser
625                 630             635                 640

Leu Ala Phe Asp Lys Cys Thr Ala Cys Ser Ser Lys Val Leu Asp Gln
                645             650             655

Tyr Glu Arg Glu Gly Phe Asn Phe Leu Ala Lys Val Phe Asn Ser Ser
                660             665             670

His Ser Phe Leu Glu Asp Leu Thr Gly Leu Thr Leu Leu His Gln Glu
                675             680             685

Thr Gln Ala Ala Glu Ile Trp Asp Met Ser Asp Asp Glu Thr Ile
            690             695             700

<210> SEQ ID NO 2
<211> LENGTH: 5059
<212> TYPE: DNA
<213> ORGANISM: Homo sapiens

<400> SEQUENCE: 2

| | |
|---|---|
|ctttgcgcac gcgcgccgct tcccagtggc aagcgcgggc aggaccgcgt tgcgtcatcg|60|
|gggcgcgcgc ctcagagaga gctgtggttg ccggaagttg agcggcggca agaaataatg|120|
|gcggcagcta cggggatcc tggactctct aaactgcagt ttgccccttt tagtagtgcc|180|
|ttggatgttg ggttttggca tgagttgacc cagaagaagc tgaacgagta tcggctggat|240|
|gaagctccca aggacattaa gggttattac tacaatggtg actctgctgg gctgccagct|300|
|cgcttaacat tggagttcag tgcttttgac atgagtgctc ccaccccagc ccgttgctgc|360|
|ccagctattg aacactgta taacaccaac acactcgagt ctttcaagac tgcagataag|420|
|aagctccttt tggaacaagc agcaaatgag atatgggaat ccataaaatc aggcactgct|480|
|cttgaaaacc ctgtactcct caacaagttc ctcctcttga catttgcaga tctaaagaag|540|
|taccacttct actattggtt tgctatcct gccctctgtc ttccagagag tttacctctc|600|
|attcaggggc cagtgggttt ggatcaaagg ttttcactaa aacagattga agcactagag|660|
|tgtgcatatg ataatctttg tcaaacagaa ggagtcacag ctcttcctta cttcttaatc|720|
|aagtatgatg agaacatggt gctggtttcc ttgcttaaac actacagtga tttcttccaa|780|

```
ggtcaaagga cgaagataac aattggtgta tatgatccct gtaacttagc ccagtaccct    840
ggatggcctt tgaggaattt tttggtccta gcagcccaca gatggagtag cagtttccag    900
tctgttgaag ttgtttgctt ccgtgaccgt accatgcagg gggcgagaga cgttgcccac    960
agcatcatct tcgaagtgaa gcttccagaa atggcattta gcccagattg tcctaaagca   1020
gttggatggg aaaagaacca gaaaggaggc atgggaccaa ggatggtgaa cctcagtgaa   1080
tgtatggacc ctaaaaggtt agctgagtca tcagtggatc taaatctcaa actgatgtgt   1140
tggagattgg ttcctacttt agacttggac aaggttgtgt ctgtcaaatg tctgctgctt   1200
ggagccggca ccttgggttg caatgtagct aggacgttga tgggttgggg cgtgagacac   1260
atcacatttg tggacaatgc caagatctcc tactccaatc ctgtgaggca gcctctctat   1320
gagtttgaag attgcctagg gggtggtaag cccaaggctc tggcagcagc ggaccggctc   1380
cagaaaatat tccccggtgt gaatgccaga ggattcaaca tgagcatacc tatgcctggg   1440
catccagtga acttctccag tgtcactctg gagcaagccc gcagagatgt ggagcaactg   1500
gagcagctca tcgaaagcca tgatgtcgtc ttcctattga tggacaccag ggagagccgg   1560
tggcttcctg ccgtcattgc tgcaagcaag agaaagctgg tcatcaatgc tgctttggga   1620
tttgacacat tgttgtcat gagacatggt ctgaagaaac caaagcagca aggagctggg   1680
gacttgtgtc caaaccaccc tgtggcatct gctgacctcc tgggctcatc gcttttgcc    1740 aacatccctg gttacaagct tggctgctac ttctgcaatg atgtggtggc cccaggagat   1800
tcaaccagag accggacctt ggaccagcag tgcactgtga gtcgtccagg actggccgtg   1860
attgcaggag ccctggccgt ggaattgatg gtatctgttt tgcagcatcc agaaggggc    1920 tatgccattg ccagcagcag tgacgatcgg atgaatgagc ctccaacctc tcttgggctt   1980
gtgcctcacc agatccgggg atttctttca cggtttgata atgtccttcc cgtcagcctg   2040
gcatttgaca aatgtacagc ttgttcttcc aaagttcttg atcaatatga acgaaagga    2100 tttaacttcc tagccaaggt gtttaattct tcacattcct tcttagaaga cttgactggt   2160
cttacattgc tgcatcaaga aacccaagct gctgagatct gggacatgag cgatgatgag   2220
accatctgag atggccccgc tgtggggctg acttctcccc ggccgcctgc tgaggagctc   2280
tccatcgcca gagcaggact gctgacccca ggcctggtga ttctgggccc ctcctccata   2340 cccccgaggtc tgggattccc ccctctgctg cccaggagtg gccagtgttc ggcgttgctc   2400
gggattcaag ataccaccag ttcagagcta aataataacc ttggccttgg ccttgctatt   2460
gacctgggac ttggtcctcc atgcagtttt tatttcttgt cacagtgact gatagccatc   2520
ccccaggatc ctttcccctt ggccctgagg ggtgaccca acacagacca aatggggaaa     2580
tgagcaacca gctcctgccc agagccactg cgggaggtgg caccctcatc cccggaatgt   2640
gctgcccacc gcaccgcagg ctcctcctgt gggggccctg gcatgggtg agggtgggac     2700 cccgtgagcg cactgcaccc tggccctggt ggagcgggag gaggaggaga gccgagctgg   2760
gtacgagact aaagggccca catgacccag tgacgccaga tttccaccaa ggactgagtg   2820
agctgctcag acatggcttt ctgcctccca gcctgtcctc cactgtgggc atagcatctg   2880
tgcctgcctg cctgcttgag ggagaggagt ttctgctgct gccttgagct gggggaaga    2940 gcccaggggc agatcctggc agctgcctgg atggggctcc tccctgccct tatgagcagg   3000
ccaggcccag aaaggccgag cctggctgc cttcctgccc cagccgaggg aggggtcaga    3060
cggctctacc atgggtaact caggcaagag ctggttttcc tctttattct gggtgtgtgc   3120
```

```
agctgtgagg ccccaaccca ggagaggcca tggcctaggt acctgtgacc accctgcccc    3180
cgtgtagagg gcatcgtctt tcctgctatt ttattctttc agcttttgtc ttaggcccag    3240
aatcaaagtg aaaattgagt cgagctgacc cttacaacag taggatttag tagggtagat    3300
ttcaaatgag gcttcgcttc tcccaaagta gccagtccaa gttccagtgg ctgtcgttca    3360
gctcatggga gcttcatggg gacacagccg gcacaggtgc agggcccgag tccgcccacc    3420
cagcctggcg ctgaaactgc acacgtacac tatgtggttt aagagcactt tattattgtt    3480
cttaaggcta cttttaagta caaaaaaaga tggcctgcca aaccttttt tttcttcttc     3540
caggaaaaac aggccacaga gaatggtata ttacagattt acacacatga agagaaggtc    3600
agagcgcact gcaggcagcg cggctctggg aagaacttca cggagcccct tcttagagca    3660
gggaggggc tttctcagtg aaatgtttgg ttttctgctg cctcctctgc cccaggcccc     3720
cctccagggt actgcctatc ccagataggt cagtgcacca gggacccggc cgccagcacc    3780
gccgacccct cccagagtga cgcccttgtt cactgacaaa gagacctgtc ccaggagtgt    3840
cctccaccga gccggtcagc tgtgggtggt tttcctgtta cgacgctcag tagcctgtag    3900
caataacaaa ctcgtggcta tgaatgcaga tgcagtgttc tcatagaata actgttcctg    3960
cacttttaca gacaaatcta cgacaaaaaa aaagatcaac tttttttttc cgaacaacaa    4020
aaaaaatgaa tgattacaat aggaaaggga aaaattaaat agctacatat cattaacaaa    4080
ttaatgttct tcaaaaaata cctacaaatt tctctgtaca ttctttacgc acagcgtaac    4140
gatggtctca aaatcaccca tatagaaaag tgttctcaac gattttttcct acagaaaata   4200
tagggggcctg aatgccaaag cttggaagcc cagtacagtg ggagtgaaat gtgtgcgggg   4260
caaggagaag ggcttttctt tcctccactt ttcaaaggcc tgcagccact ctgtgactac    4320
aagagccagt cctccgacct tttcacccag tgccaatttc caaaattcaa cagctaaaaa    4380
ctgtaaaacc gggggtcata cggtgtgcag agtccacaaa gccttgcagg tgaggtgacc    4440
acgcccacgt cacctggtca ggtgccatcg tcgtgagcct ctggtgggcc aggtgggaca    4500
cagcacaccc cagggggagg ggatagaaac gctcattgac caaaaggag cagctgtgac     4560
ctccacagct gtgtctgtca tgcttgcttc atctaatttc tagttagtag ctattaatat    4620
agcaaataat aaatgcagta ataacagtat aaagtcagag gaatgtatac tgccttggcc    4680
ccagcgtacg aggaagcgta taaaacacca tatcacagat tgtctgtcag taatctgctg    4740
ttcagccaag agagttcaaa gggagcagtt tctgcatgta gggaagttgg aagacacaaa    4800
cccccacctcc cctgggagct tgtaacaaag cagacaggga tgcaaaaata aatgatgtca   4860
gcctgcagcc aaactccagc atcccacacc gcagctgacc cactgctcat cgcgagggcc    4920
tgccaggagc tggcctcccg cactacttgt gagtaaagtg aatatcaaat accaatctta    4980
gagtacaact gtaccagcag taagtatatc taggactgta actgacaaaa ataaactaat    5040
tctgaaaaga aaaaaaaaa                                                 5059
```

<210> SEQ ID NO 3
<211> LENGTH: 326
<212> TYPE: PRT
<213> ORGANISM: Homo sapiens

<400> SEQUENCE: 3

Met His Arg Thr Thr Arg Ile Lys Ile Thr Glu Leu Asn Pro His Leu
1               5                   10                  15

Met Cys Val Leu Cys Gly Gly Tyr Phe Ile Asp Ala Thr Thr Ile Ile
            20                  25                  30

```
Glu Cys Leu His Ser Phe Cys Lys Thr Cys Ile Val Arg Tyr Leu Glu
             35                  40                  45

Thr Ser Lys Tyr Cys Pro Ile Cys Asp Val Gln Val His Lys Thr Arg
         50                  55                  60

Pro Leu Leu Asn Ile Arg Ser Asp Lys Thr Leu Gln Asp Ile Val Tyr
 65                  70                  75                  80

Lys Leu Val Pro Gly Leu Phe Lys Asn Glu Met Lys Arg Arg Arg Asp
                 85                  90                  95

Phe Tyr Ala Ala His Pro Ser Ala Asp Ala Ala Asn Gly Ser Asn Glu
            100                 105                 110

Asp Arg Gly Glu Val Ala Asp Glu Asp Lys Arg Ile Ile Thr Asp Asp
            115                 120                 125

Glu Ile Ile Ser Leu Ser Ile Glu Phe Phe Asp Gln Asn Arg Leu Asp
            130                 135                 140

Arg Lys Val Asn Lys Asp Lys Glu Lys Ser Lys Glu Val Asn Asp
145                 150                 155                 160

Lys Arg Tyr Leu Arg Cys Pro Ala Ala Met Thr Val Met His Leu Arg
                165                 170                 175

Lys Phe Leu Arg Ser Lys Met Asp Ile Pro Asn Thr Phe Gln Ile Asp
            180                 185                 190

Val Met Tyr Glu Glu Pro Leu Lys Asp Tyr Tyr Thr Leu Met Asp
            195                 200                 205

Ile Ala Tyr Ile Tyr Thr Trp Arg Arg Asn Gly Pro Leu Pro Leu Lys
            210                 215                 220

Tyr Arg Val Arg Pro Thr Cys Lys Arg Met Lys Ile Ser His Gln Arg
225                 230                 235                 240

Asp Gly Leu Thr Asn Ala Gly Glu Leu Glu Ser Asp Ser Gly Ser Asp
                245                 250                 255

Lys Ala Asn Ser Pro Ala Gly Gly Ile Pro Ser Thr Ser Ser Cys Leu
            260                 265                 270

Pro Ser Pro Ser Thr Pro Val Gln Ser Pro His Pro Gln Phe Pro His
            275                 280                 285

Ile Ser Ser Thr Met Asn Gly Thr Ser Asn Ser Pro Ser Gly Asn His
            290                 295                 300

Gln Ser Ser Phe Ala Asn Arg Pro Arg Lys Ser Ser Val Asn Gly Ser
305                 310                 315                 320

Ser Ala Thr Ser Ser Gly
                325

<210> SEQ ID NO 4
<211> LENGTH: 454
<212> TYPE: PRT
<213> ORGANISM: Homo sapiens

<400> SEQUENCE: 4

Met Asp Phe Phe Arg Val Val Glu Asn Gln Gln Pro Pro Ala Thr Met
 1               5                  10                  15

Pro Leu Asn Val Ser Phe Thr Asn Arg Asn Tyr Asp Leu Asp Tyr Asp
                 20                  25                  30

Ser Val Gln Pro Tyr Phe Tyr Cys Asp Glu Glu Asn Phe Tyr Gln
             35                  40                  45

Gln Gln Gln Gln Ser Glu Leu Gln Pro Pro Ala Pro Ser Glu Asp Ile
         50                  55                  60

Trp Lys Lys Phe Glu Leu Leu Pro Thr Pro Pro Leu Ser Pro Ser Arg
```

```
                65                  70                  75                  80
        Arg Ser Gly Leu Cys Ser Pro Ser Tyr Val Ala Val Thr Pro Phe Ser
                            85                  90                  95

Leu Arg Gly Asp Asn Asp Gly Gly Gly Ser Phe Ser Thr Ala Asp
                    100                 105                 110

Gln Leu Glu Met Val Thr Glu Leu Gly Gly Asp Met Val Asn Gln
                    115                 120                 125

Ser Phe Ile Cys Asp Pro Asp Asp Glu Thr Phe Ile Lys Asn Ile Ile
            130                 135                 140

Ile Gln Asp Cys Met Trp Ser Gly Phe Ser Ala Ala Lys Leu Val
        145                 150                 155                 160

Ser Glu Lys Leu Ala Ser Tyr Gln Ala Ala Arg Lys Asp Ser Gly Ser
                        165                 170                 175

Pro Asn Pro Ala Arg Gly His Ser Val Cys Ser Thr Ser Ser Leu Tyr
                    180                 185                 190

Leu Gln Asp Leu Ser Ala Ala Ser Glu Cys Ile Asp Pro Ser Val
                195                 200                 205

Val Phe Pro Tyr Pro Leu Asn Asp Ser Ser Pro Lys Ser Cys Ala
            210                 215                 220

Ser Gln Asp Ser Ser Ala Phe Ser Pro Ser Ser Asp Ser Leu Leu Ser
        225                 230                 235                 240

Ser Thr Glu Ser Ser Pro Gln Gly Ser Pro Glu Pro Leu Val Leu His
                        245                 250                 255

Glu Glu Thr Pro Pro Thr Thr Ser Ser Asp Ser Glu Glu Glu Gln Glu
                    260                 265                 270

Asp Glu Glu Glu Ile Asp Val Val Ser Val Glu Lys Arg Gln Ala Pro
                    275                 280                 285

Gly Lys Arg Ser Glu Ser Gly Ser Pro Ser Ala Gly Gly His Ser Lys
                290                 295                 300

Pro Pro His Ser Pro Leu Val Leu Lys Arg Cys His Val Ser Thr His
        305                 310                 315                 320

Gln His Asn Tyr Ala Ala Pro Pro Ser Thr Arg Lys Asp Tyr Pro Ala
                        325                 330                 335

Ala Lys Arg Val Lys Leu Asp Ser Val Arg Val Leu Arg Gln Ile Ser
                    340                 345                 350

Asn Asn Arg Lys Cys Thr Ser Pro Arg Ser Ser Asp Thr Glu Glu Asn
                    355                 360                 365

Val Lys Arg Arg Thr His Asn Val Leu Glu Arg Gln Arg Arg Asn Glu
            370                 375                 380

Leu Lys Arg Ser Phe Phe Ala Leu Arg Asp Gln Ile Pro Glu Leu Glu
        385                 390                 395                 400

Asn Asn Glu Lys Ala Pro Lys Val Val Ile Leu Lys Lys Ala Thr Ala
                        405                 410                 415

Tyr Ile Leu Ser Val Gln Ala Glu Glu Gln Lys Leu Ile Ser Glu Glu
                    420                 425                 430

Asp Leu Leu Arg Lys Arg Arg Glu Gln Leu Lys His Lys Leu Glu Gln
                    435                 440                 445

Leu Arg Asn Ser Cys Ala
            450

<210> SEQ ID NO 5
<211> LENGTH: 2379
<212> TYPE: DNA
<213> ORGANISM: Homo sapiens
```

<400> SEQUENCE: 5

```
gaccccgag ctgtgctgct cgcggccgcc accgccgggc cccggccgtc cctggctccc       60
ctcctgcctc gagaagggca gggcttctca gaggcttggc gggaaaaaga acggagggag      120
ggatcgcgct gagtataaaa gccggttttc ggggctttat ctaactcgct gtagtaattc      180
cagcgagagg cagagggagc gagcgggcgg ccggctaggg tggaagagcc gggcgagcag      240
agctgcgctg cgggcgtcct gggaagggag atccggagcg aatagggggc ttcgcctctg      300
gcccagccct cccgctgatc ccccagccag cggtccgcaa cccttgccgc atccacgaaa      360
ctttgcccat agcagcgggc gggcactttg cactggaact acaacacccc gagcaaggac      420
gcgactctcc cgacgcgggg aggctattct gcccatttgg ggacacttcc ccgccgctgc      480
caggacccgc ttctctgaaa ggctctcctt gcagctgctt agacgctgga ttttttcgg      540
gtagtggaaa accagcagcc tcccgcgacg atgcccctca cgttagcttt caccaacagg      600
aactatgacc tcgactacga ctcggtgcag ccgtatttct actgcgacga ggaggagaac      660
ttctaccagc agcagcagca gagcgagctg cagcccccgg cgcccagcga ggatatctgg      720
aagaaattcg agctgctgcc caccccgccc ctgtccccta gccgccgctc cgggctctgc      780
tcgccctcct acgttgcggt cacacccttc tcccttcggg gagacaacga cggcggtggc      840
gggagcttct ccacgccgga ccagctggag atggtgaccg agctgctggg aggagacatg      900
gtgaaccaga gtttcatctg cgacccggac gacgagacct tcatcaaaaa catcatcatc      960
caggactgta tgtggagcgg cttctcggcc gccgccaagc tcgtctcaga gaagctggcc     1020
tcctaccagg ctgcgcgcaa agacagcggc agcccgaacc ccgccgcgg ccacagcgtc      1080
tgctccacct ccagcttgta cctgcaggat ctgagcgccg ccgcctcaga gtgcatcgac     1140
ccctcggtgg tcttccccta ccctctcaac gacagcagct cgcccaagtc ctgcgcctcg     1200
caagactcca gcgccttctc tccgtcctcg gattctctgc tctcctcgac ggagtcctcc     1260
ccgcagggca gccccgagcc cctggtgctc catgaggaga caccgcccac caccagcagc     1320
gactctgagg aggaacaaga agatgaggaa gaaatcgatg ttgtttctgt ggaaaagagg     1380
caggctcctg gcaaaaggtc agagtctgga tcaccttctg ctggaggcca cagcaaacct     1440
cctcacagcc cactggtcct caagaggtgc acgtctcca cacatcagca caactacgca      1500
gcgcctccct ccactcggaa ggactatcct gctgccaaga gggtcaagtt ggacagtgtc     1560
agagtcctga cacagatcag caacaaccga aaatgcacca gccccaggtc ctcggacacc     1620
gaggagaatg tcaagaggcg aacacacaac gtcttggagc gccagaggag gaacgagcta     1680
aaacggagct ttttgccct gcgtgaccag atcccggagt tggaaaacaa tgaaaaggcc     1740
cccaaggtag ttatccttaa aaaagccaca gcatacatcc tgtccgtcca agcagaggag     1800
caaaagctca tttctgaaga ggacttgttg cggaaacgac gagaacagtt gaaacacaaa     1860
cttgaacagc tacggaactc ttgtgcgtaa ggaaaagtaa ggaaaacgat tccttctaac     1920
agaaatgtcc tgagcaatca cctatgaact tgtttcaaat gcatgatcaa atgcaacctc     1980
acaaccttgg ctgagtcttg agactgaaag atttagccat aatgtaaact gcctcaaatt     2040
ggactttggg cataaaagaa cttttttatg cttaccatct ttttttttc tttaacagat      2100
ttgtatttaa gaattgtttt taaaaaattt taagatttac acaatgtttc tctgtaaata     2160
ttgccattaa atgtaaataa ctttaataaa acgtttatag cagttacaca gaatttcaat     2220
cctagtatat agtacctagt attataggta ctataaaccc taattttttt tatttaagta     2280
```

```
cattttgctt tttaaagttg attttttct attgtttta gaaaaaataa aataactggc      2340
aaatatatca ttgagccaaa tcttaaaaaa aaaaaaaaa                            2379

<210> SEQ ID NO 6
<211> LENGTH: 651
<212> TYPE: PRT
<213> ORGANISM: Homo sapiens

<400> SEQUENCE: 6

Met Asn Gln Pro Gln Arg Met Ala Pro Val Gly Thr Asp Lys Glu Leu
1               5                   10                  15

Ser Asp Leu Leu Asp Phe Ser Met Met Phe Pro Leu Pro Val Thr Asn
            20                  25                  30

Gly Lys Gly Arg Pro Ala Ser Leu Ala Gly Ala Gln Phe Gly Gly Ser
        35                  40                  45

Gly Leu Glu Asp Arg Pro Ser Ser Gly Ser Trp Gly Ser Gly Asp Gln
    50                  55                  60

Ser Ser Ser Ser Phe Asp Pro Ser Arg Thr Phe Ser Glu Gly Thr His
65                  70                  75                  80

Phe Thr Glu Ser His Ser Ser Leu Ser Ser Thr Phe Leu Gly Pro
                85                  90                  95

Gly Leu Gly Gly Lys Ser Gly Glu Arg Gly Ala Tyr Ala Ser Phe Gly
            100                 105                 110

Arg Asp Ala Gly Val Gly Gly Leu Thr Gln Ala Gly Phe Leu Ser Gly
        115                 120                 125

Glu Leu Ala Leu Asn Ser Pro Gly Pro Leu Ser Pro Ser Gly Met Lys
    130                 135                 140

Gly Thr Ser Gln Tyr Tyr Pro Ser Tyr Ser Gly Ser Ser Arg Arg Arg
145                 150                 155                 160

Ala Ala Asp Gly Ser Leu Asp Thr Gln Pro Lys Lys Val Arg Lys Val
                165                 170                 175

Pro Pro Gly Leu Pro Ser Ser Val Tyr Pro Pro Ser Ser Gly Glu Asp
            180                 185                 190

Tyr Gly Arg Asp Ala Thr Ala Tyr Pro Ser Ala Lys Thr Pro Ser Ser
        195                 200                 205

Thr Tyr Pro Ala Pro Phe Tyr Val Ala Asp Gly Ser Leu His Pro Ser
    210                 215                 220

Ala Glu Leu Trp Ser Pro Gly Gln Ala Gly Phe Gly Pro Met Leu
225                 230                 235                 240

Gly Gly Gly Ser Ser Pro Leu Pro Leu Pro Pro Gly Ser Gly Pro Val
                245                 250                 255

Gly Ser Ser Gly Ser Ser Thr Phe Gly Gly Leu His Gln His Glu
            260                 265                 270

Arg Met Gly Tyr Gln Leu His Gly Ala Glu Val Asn Gly Gly Leu Pro
        275                 280                 285

Ser Ala Ser Ser Phe Ser Ala Pro Gly Ala Thr Tyr Gly Gly Val
    290                 295                 300

Ser Ser His Thr Pro Pro Val Ser Gly Ala Asp Ser Leu Leu Gly Ser
305                 310                 315                 320

Arg Gly Thr Thr Ala Gly Ser Ser Gly Asp Ala Leu Gly Lys Ala Leu
                325                 330                 335

Ala Ser Ile Tyr Ser Pro Asp His Ser Ser Asn Asn Phe Ser Ser Ser
            340                 345                 350

Pro Ser Thr Pro Val Gly Ser Pro Gln Gly Leu Ala Gly Thr Ser Gln
```

```
                355                 360                 365
Trp Pro Arg Ala Gly Ala Pro Gly Ala Leu Ser Pro Ser Tyr Asp Gly
370                 375                 380

Gly Leu His Gly Leu Gln Ser Lys Ile Glu Asp His Leu Asp Glu Ala
385                 390                 395                 400

Ile His Val Leu Arg Ser His Ala Val Gly Thr Ala Gly Asp Met His
                405                 410                 415

Thr Leu Leu Pro Gly His Gly Ala Leu Ala Ser Gly Phe Thr Gly Pro
                420                 425                 430

Met Ser Leu Gly Gly Arg His Ala Gly Leu Val Gly Gly Ser His Pro
                435                 440                 445

Glu Asp Gly Leu Ala Gly Ser Thr Ser Leu Met His Asn His Ala Ala
450                 455                 460

Leu Pro Ser Gln Pro Gly Thr Leu Pro Asp Leu Ser Arg Pro Pro Asp
465                 470                 475                 480

Ser Tyr Ser Gly Leu Gly Arg Ala Gly Ala Thr Ala Ala Ala Ser Glu
                485                 490                 495

Ile Lys Arg Glu Glu Lys Glu Asp Glu Glu Asn Thr Ser Ala Ala Asp
                500                 505                 510

His Ser Glu Glu Glu Lys Lys Glu Leu Lys Ala Pro Arg Ala Arg Thr
                515                 520                 525

Ser Ser Thr Asp Glu Val Leu Ser Leu Glu Glu Lys Asp Leu Arg Asp
530                 535                 540

Arg Glu Arg Arg Met Ala Asn Asn Ala Arg Glu Arg Val Arg Val Arg
545                 550                 555                 560

Asp Ile Asn Glu Ala Phe Arg Glu Leu Gly Arg Met Cys Gln Met His
                565                 570                 575

Leu Lys Ser Asp Lys Ala Gln Thr Lys Leu Leu Ile Leu Gln Gln Ala
                580                 585                 590

Val Gln Val Ile Leu Gly Leu Glu Gln Gln Val Arg Glu Arg Asn Leu
                595                 600                 605

Asn Pro Lys Ala Ala Cys Leu Lys Arg Arg Glu Glu Glu Lys Val Ser
610                 615                 620

Gly Val Val Gly Asp Pro Gln Met Val Leu Ser Ala Pro His Pro Gly
625                 630                 635                 640

Leu Ser Glu Ala His Asn Pro Ala Gly His Met
                645                 650

<210> SEQ ID NO 7
<211> LENGTH: 4078
<212> TYPE: DNA
<213> ORGANISM: Homo sapiens

<400> SEQUENCE: 7
ggtttccagg cctgaggtgc ccgccctggc cccaggagaa tgaaccagcc gcagaggatg      60
gcgcctgtgg gcacagacaa ggagctcagt gacctcctgg acttcagcat gatgttcccg     120
ctgcctgtca ccaacgggaa gggccggccc gcctccctgg ccggggcgca gttcggaggt     180
tcaggtcttg aggaccggcc cagctcaggc tcctggggca gcggcgacca gagcagctcc     240
tcctttgacc ccagccggac cttcagcgag gcacccact tcactgagtc gcacagcagc     300
ctctcttcat ccacattcct ggaccgggac tcggaggca agagcggtga gcggggcgcc     360
tatgcctcct tcgggagaga cgcaggcgtg gcggcctga tcaggctgg cttcctgtca     420 ggcgagctgg ccctcaacag ccccgggccc ctgtcccctt cgggcatgaa ggggacctcc     480
```

```
cagtactacc cctcctactc cggcagctcc cggcggagag cggcagacgg cagcctagac    540
acgcagccca agaaggtccg gaaggtcccg ccgggtcttc catcctcggt gtacccaccc    600
agctcaggtg aggactacgg cagggatgcc accgcctacc cgtccgccaa gaccccagc    660 agcacctatc ccgcccctt ctacgtggca gatggcagcc tgcaccctc agccgagctc    720 tggagtcccc cgggccaggc gggcttcggg cccatgctgg gtgggggctc atccccgctg    780
cccctcccgc ccggtagcgg cccggtgggc agcagtggaa gcagcagcac gtttggtggc    840
ctgcaccagc acgagcgtat gggctaccag ctgcatggag cagaggtgaa cggtgggctc    900
ccatctgcat cctccttctc ctcagccccc ggagccacgt acggcggcgt ctccagccac    960
acgccgcctg tcagcggggc cgacagcctc ctgggctccc gagggaccac agctggcagc   1020
tccggggatg ccctcggcaa agcactggcc tcgatctact ccccggatca ctcaagcaat   1080
aacttctcgt ccagcccttc tacccccgtg gctcccccc agggcctggc aggaacgtca   1140
cagtggcctc gagcaggagc ccccggtgcc ttatcgccca gctacgacgg gggtctccac   1200
ggcctgcaga gtaagataga agaccacctg gacgaggcca tccacgtgct ccgcagccac   1260
gccgtgggca cagccggcga catgcacacg ctgctgcctg ccacggggc gctggcctca   1320 ggtttcaccg gccccatgtc actgggcggg cggcacgcag gcctggttgg aggcagccac   1380
cccgaggacg gcctcgcagg cagcaccagc ctcatgcaca accacgcggc cctccccagc   1440
cagccaggca ccctccctga cctgtctcgg cctcccgact cctacagtgg gctagggcga   1500
gcaggtgcca cggcggccgc cagcgagatc aagcggagg agaaggagga cgaggagaac   1560
acgtcagcgg ctgaccactc ggaggaggag aagaaggagc tgaaggcccc ccgggcccgg   1620
accagcagta cggacgaggt gctgtccctg gaggagaaag acctgaggga ccgggagagg   1680
cgcatggcca ataacgcgcg ggagcgggtg cgcgtgcggg atattaacga ggccttccgg   1740
gagctggggc gcatgtgcca gatgcacctc aagtcggaca agcgcagac caagctgctc   1800 atcctgcagc aggccgtgca ggtcatcctg gggctggagc agcaggtgcg agagcggaac   1860
ctgaatccca aagcagcctg tttgaaacgg cgagaagagg aaaaggtgtc aggtgtggtt   1920
ggagaccccc agatggtgct ttcagctccc cacccaggcc tgagcgaagc ccacaacccc   1980
gccgggcaca tgtgaaagta aacaaaacct gaaagcaagc aacaaaacat acactttgtc   2040
agagaagaaa aaaatgcctt aactataaaa agcggagaaa tggaaacata tcactcaagg   2100
gggatgctgt ggaaacctgg cttattcttc taaagccacc agcaaattgt gcctaagcga   2160
aatatttttt ttaaggaaaa taaaaacatt agttacaaga tttttttttt cttaatgtag   2220
atgaaaatta gcaaggatgc tgcctttggt ctctggtttt tttaagcttt ttttgcatat   2280
gttttgtaag caacaaattt ttttgtataa aagtcccgtg tctctcgcta tttctgctgc   2340
tgttcctaga ctgagcattg catttcttga tcaaccagat gattaaacgt tgtattaaaa   2400
agaccccgtg taaacctgag cccccccgtc cccccccc ccggaagcc actgcacaca   2460 gacagaacgg ggacaggcgg cgggtctttt gttttttga tgttgggggt tctcttggtt   2520
ttgtcatgtg gaaagtgatg cgtgggcgtt ccctgatgaa ggcacttggg gcttccctg    2580 ccgcatcctc tccctcagg aaggggactg acctgggctt gggggaaggg acgtcagcaa   2640
ggtggctctg accctcccag gtgactctgc caagcagctg tggccccag ggctacccta   2700 cacaacgccc tccccaggcc cccctaagct gctctccctt ggaacctgca cagctctctg   2760
aaatggggca ttttgttggg accagtgacc cctggcatgg ggaccacacc ctggagcccg   2820
```

```
gtgctgggga cctcctggac accctgtcct tcactccttt gccccaggga cccaggctca    2880
tgctctgaac tctggctgag aggatgctgc tcaggagcca gcacaggaca ccccccaccc    2940
caccccacca tgtccccatt acaccagagg gccatcgtga cgtagacagg atgccagggg    3000
cctggccagc ctcccccaat gctggggagc atccctgggc ctggggccac acctgctgcc    3060
ctccctctgt gtggtccaag ggcaagagtg gctggagccg ggggactgtg ctggtctgag    3120
ccccacgaag gccttgggct gtgcgtccga ccctgctgca gaaccagcag ggtgcccct     3180 cgggcccatc tgtgtcccat gtcccagcac ccaggcctct ctccaggtct ccttttctgg    3240
tcttttgcca tgagggtaac cagctcttcc cagctggctg gggactgtct tgggtttaaa    3300
actgcaagtc tcctaccctg ggatcccatc cagttccaca cgaactaggg cagtggtcac    3360
tgtggcaccc aggtgtgggc ctggctagct gggggccttc atgtgcccct catgcccctc    3420
cctgcattga ggccttgtgg accctgggc tggctgtgtt catccccgct gcaggtcggg     3480
cgtctccccc cgtgccactc ctgagactcc accgttaccc ccaggagat cctggactgc     3540 ctgactcccc tccccagact ggcttgggag cctgggcccc atggtagatg caagggaaac    3600
ctcaaggcca gctcaatgcc tggtatctgc ccccagtcca ggccaggcgg agggagggg    3660 ctgtccggct gcctctccct tctcggtggc ttccctacg ccctgggagt ttgatctctt     3720
aagggaactt gcctctccct cttgttttgc tcctggccct gccctaggt ctgggtgggc     3780 agtggcccca tagcctctgg aactgtgcgt tctgcataga attcaaacga gattcaccca    3840
gcgcgaggag gaagaaacag cagttcctgg gaaccacaat tatggggggt ggggggtgtg    3900
atctgagtgc ctcaagatgg ttttcaaaaa aatttttta aagaaaataa ttgtatacgt     3960
gtcaacacag ctggctggat gattgggact ttaaaacgac cctctttcag gtggattcag    4020
agacctgtcc tgtatataac agcactgtag caataaacgt gacattttat aacgatgc     4078
```

```
<210> SEQ ID NO 8
<211> LENGTH: 480
<212> TYPE: PRT
<213> ORGANISM: Homo sapiens

<400> SEQUENCE: 8

Met Glu Val Ala Pro Glu Gln Pro Arg Trp Met Ala His Pro Ala Val
1               5                   10                  15

Leu Asn Ala Gln His Pro Asp Ser His His Pro Gly Leu Ala His Asn
            20                  25                  30

Tyr Met Glu Pro Ala Gln Leu Leu Pro Pro Asp Glu Val Asp Val Phe
        35                  40                  45

Phe Asn His Leu Asp Ser Gln Gly Asn Pro Tyr Tyr Ala Asn Pro Ala
    50                  55                  60

His Ala Arg Ala Arg Val Ser Tyr Ser Pro Ala His Ala Arg Leu Thr
65                  70                  75                  80

Gly Gly Gln Met Cys Arg Pro His Leu Leu His Ser Pro Gly Leu Pro
                85                  90                  95

Trp Leu Asp Gly Gly Lys Ala Ala Leu Ser Ala Ala Ala His His
            100                 105                 110

His Asn Pro Trp Thr Val Ser Pro Phe Ser Lys Thr Pro Leu His Pro
        115                 120                 125

Ser Ala Ala Gly Gly Pro Gly Gly Pro Leu Ser Val Tyr Pro Gly Ala
    130                 135                 140

Gly Gly Gly Ser Gly Gly Gly Ser Gly Ser Ser Val Ala Ser Leu Thr
145                 150                 155                 160
```

```
Pro Thr Ala Ala His Ser Gly Ser His Leu Phe Gly Phe Pro Pro Thr
                165                 170                 175

Pro Pro Lys Glu Val Ser Pro Asp Pro Ser Thr Thr Gly Ala Ala Ser
            180                 185                 190

Pro Ala Ser Ser Ala Gly Gly Ser Ala Ala Arg Gly Glu Asp Lys
        195                 200                 205

Asp Gly Val Lys Tyr Gln Val Ser Leu Thr Glu Ser Met Lys Met Glu
    210                 215                 220

Ser Gly Ser Pro Leu Arg Pro Gly Leu Ala Thr Met Gly Thr Gln Pro
225                 230                 235                 240

Ala Thr His His Pro Ile Pro Thr Tyr Pro Ser Tyr Val Pro Ala Ala
                245                 250                 255

Ala His Asp Tyr Ser Ser Gly Leu Phe His Pro Gly Gly Phe Leu Gly
                260                 265                 270

Gly Pro Ala Ser Ser Phe Thr Pro Lys Gln Arg Ser Lys Ala Arg Ser
            275                 280                 285

Cys Ser Glu Gly Arg Glu Cys Val Asn Cys Gly Ala Thr Ala Thr Pro
        290                 295                 300

Leu Trp Arg Arg Asp Gly Thr Gly His Tyr Leu Cys Asn Ala Cys Gly
305                 310                 315                 320

Leu Tyr His Lys Met Asn Gly Gln Asn Arg Pro Leu Ile Lys Pro Lys
                325                 330                 335

Arg Arg Leu Ser Ala Ala Arg Arg Ala Gly Thr Cys Cys Ala Asn Cys
                340                 345                 350

Gln Thr Thr Thr Thr Thr Leu Trp Arg Arg Asn Ala Asn Gly Asp Pro
            355                 360                 365

Val Cys Asn Ala Cys Gly Leu Tyr Tyr Lys Leu His Asn Val Asn Arg
    370                 375                 380

Pro Leu Thr Met Lys Lys Glu Gly Ile Gln Thr Arg Asn Arg Lys Met
385                 390                 395                 400

Ser Asn Lys Ser Lys Lys Ser Lys Lys Gly Ala Glu Cys Phe Glu Glu
                405                 410                 415

Leu Ser Lys Cys Met Gln Glu Lys Ser Ser Pro Phe Ser Ala Ala Ala
                420                 425                 430

Leu Ala Gly His Met Ala Pro Val Gly His Leu Pro Pro Phe Ser His
            435                 440                 445

Ser Gly His Ile Leu Pro Thr Pro Thr Pro Ile His Pro Ser Ser Ser
450                 455                 460

Leu Ser Phe Gly His Pro His Pro Ser Ser Met Val Thr Ala Met Gly
465                 470                 475                 480

<210> SEQ ID NO 9
<211> LENGTH: 251
<212> TYPE: PRT
<213> ORGANISM: Homo sapiens

<400> SEQUENCE: 9

Met Ala Met Ser Ser Phe Leu Ile Asn Ser Asn Tyr Val Asp Pro Lys
1               5                   10                  15

Phe Pro Pro Cys Glu Glu Tyr Ser Gln Ser Asp Tyr Leu Pro Ser Asp
            20                  25                  30

His Ser Pro Gly Tyr Tyr Ala Gly Gly Gln Arg Arg Glu Ser Ser Phe
        35                  40                  45

Gln Pro Glu Ala Gly Phe Gly Arg Arg Ala Ala Cys Thr Val Gln Arg
```

```
              50                  55                  60
Tyr Ala Ala Cys Arg Asp Pro Gly Pro Pro Pro Pro Pro Pro Pro Pro
 65                  70                  75                  80

Pro Pro Pro Pro Pro Pro Gly Leu Ser Pro Arg Ala Pro Ala Pro
                 85                  90                  95

Pro Pro Ala Gly Ala Leu Leu Pro Glu Pro Gly Gln Arg Cys Glu Ala
                100                 105                 110

Val Ser Ser Ser Pro Pro Pro Pro Cys Ala Gln Asn Pro Leu His
                115                 120                 125

Pro Ser Pro Ser His Ser Ala Cys Lys Glu Pro Val Val Tyr Pro Trp
                130                 135                 140

Met Arg Lys Val His Val Ser Thr Val Asn Pro Asn Tyr Ala Gly Gly
145                 150                 155                 160

Glu Pro Lys Arg Ser Arg Thr Ala Tyr Thr Arg Gln Gln Val Leu Glu
                165                 170                 175

Leu Glu Lys Glu Phe His Tyr Asn Arg Tyr Leu Thr Arg Arg Arg Arg
                180                 185                 190

Val Glu Ile Ala His Ala Leu Cys Leu Ser Glu Arg Gln Ile Lys Ile
                195                 200                 205

Trp Phe Gln Asn Arg Arg Met Lys Trp Lys Lys Asp His Lys Leu Pro
210                 215                 220

Asn Thr Lys Ile Arg Ser Gly Gly Ala Ala Gly Ser Ala Gly Gly Pro
225                 230                 235                 240

Pro Gly Arg Pro Asn Gly Gly Pro Arg Ala Leu
                245                 250

<210> SEQ ID NO 10
<211> LENGTH: 350
<212> TYPE: PRT
<213> ORGANISM: Homo sapiens

<400> SEQUENCE: 10

Met Phe Gly Leu Lys Arg Asn Ala Val Ile Gly Leu Asn Leu Tyr Cys
  1               5                  10                  15

Gly Gly Ala Gly Leu Gly Ala Gly Ser Gly Gly Ala Thr Arg Pro Gly
                 20                  25                  30

Gly Arg Leu Leu Ala Thr Glu Lys Glu Ala Ser Ala Arg Arg Glu Ile
                 35                  40                  45

Gly Gly Gly Glu Ala Gly Ala Val Ile Gly Gly Ser Ala Gly Ala Ser
                 50                  55                  60

Pro Pro Ser Thr Leu Thr Pro Asp Ser Arg Arg Val Ala Arg Pro Pro
 65                  70                  75                  80

Pro Ile Gly Ala Glu Val Pro Asp Val Thr Ala Thr Pro Ala Arg Leu
                 85                  90                  95

Leu Phe Phe Ala Pro Thr Arg Arg Ala Ala Pro Leu Glu Glu Met Glu
                100                 105                 110

Ala Pro Ala Ala Asp Ala Ile Met Ser Pro Glu Glu Leu Asp Gly
                115                 120                 125

Tyr Glu Pro Glu Pro Leu Gly Lys Arg Pro Ala Val Leu Pro Leu Leu
                130                 135                 140

Glu Leu Val Gly Glu Ser Gly Asn Asn Thr Ser Thr Asp Gly Ser Leu
145                 150                 155                 160

Pro Ser Thr Pro Pro Ala Glu Glu Glu Asp Glu Leu Tyr Arg
                165                 170                 175
```

```
Gln Ser Leu Glu Ile Ile Ser Arg Tyr Leu Arg Glu Gln Ala Thr Gly
            180                 185                 190

Ala Lys Asp Thr Lys Pro Met Gly Arg Ser Gly Ala Thr Ser Arg Lys
        195                 200                 205

Ala Leu Glu Thr Leu Arg Arg Val Gly Asp Gly Val Gln Arg Asn His
    210                 215                 220

Glu Thr Ala Phe Gln Gly Met Leu Arg Lys Leu Asp Ile Lys Asn Glu
225                 230                 235                 240

Asp Asp Val Lys Ser Leu Ser Arg Val Met Ile His Val Phe Ser Asp
                245                 250                 255

Gly Val Thr Asn Trp Gly Arg Ile Val Thr Leu Ile Ser Phe Gly Ala
            260                 265                 270

Phe Val Ala Lys His Leu Lys Thr Ile Asn Gln Glu Ser Cys Ile Glu
        275                 280                 285

Pro Leu Ala Glu Ser Ile Thr Asp Val Leu Val Arg Thr Lys Arg Asp
    290                 295                 300

Trp Leu Val Lys Gln Arg Gly Trp Asp Gly Phe Val Glu Phe His
305                 310                 315                 320

Val Glu Asp Leu Glu Gly Gly Ile Arg Asn Val Leu Leu Ala Phe Ala
                325                 330                 335

Gly Val Ala Gly Val Gly Ala Gly Leu Ala Tyr Leu Ile Arg
            340                 345                 350

<210> SEQ ID NO 11
<211> LENGTH: 12192
<212> TYPE: DNA
<213> ORGANISM: Homo sapiens

<400> SEQUENCE: 11
tctttgagat ggagtcttcc tctatcaccc aggctggagt gcagtggcac aatctcagct      60
cactgcaacc tccgcctccc gagttcaagc aattctcctg ccacagcctc tgcagtagct     120
gggattacag gcacccatca ccacgcccaa ctaattttg tattttttagt agagatgggg     180
tttcaccatg ttggccaggc tggtcttgaa ctcctgacct taggtgatcc acccacctcg     240
gcctcccaaa gttctgggat tacaggcgtg agctaccacg cctggccaaa ttatgatctt     300
atatgtgaaa atgattatgt aaaaatgatt gattatggtg ttgtgatggg agatgctgtg     360
ctgtcggcac agtagtaggg cataggctgg gcgcggtggc tcacgcctgt aatcccagca     420
ctttgggagg ccgaggtggg cggatcacga ggtcaggaga tcgagaccat cttggctaac     480
acggtgaaac cctgtctcta ctaaaaatac aaaaaattag ccaggcgcct gtagtcccag     540
ctactcggga ggctgaggca agaatggc gtgaacccgg agacggagc ttgcagtgag      600
ccagatagc gccatggcag tccggcctgg gtgaaagagc aagactctgt ctcaaaaaaa      660
aaaaaaaaat acaaaaatta gctgggtgta atggcacgcg cctgtagtcc cagctattca      720
ggaggctgag gccgaattgc ttgaacctgg gtggtggaag ttgcagtgag ccaagaccgc      780
gccattgcac tccaacctgg gcggcagagc aaggctccat ctcaaaaaaa aaaaaaaaaa      840
aaaaaaaaaa aggccgggcg cagcggctca catttgtaat cccagcactt tgggaggctg      900
aggcaggtgg atcacaaggt caggagtttg agaccggcct ggctaacata gtgaaaccct      960
gtctctacta aaaatacaaa aattagccgg gcatggtggt gcgcacctgt agtcccagct     1020
acttgggagg ctgaggcagg agaaacggtt gaacccagga ggtggaggtt gtggtgagcc     1080
gagattgtgc cactccactc cagcctgggc aacagagcaa gactccgtct caaaaaaaaa     1140
```

```
ataagtaaaa taaaataaaa taaaatgtat ttgaaactgg gtgtggtggc tcatgcttat    1200
aatcccagct attcaagagg ctcaggtggg aggatccctt gaggacagga gttgtagacc    1260
atcctggata acatagcaag actttgttac tttctttctt tttttttttt tgagacagag    1320
tctcgttctg ttgcccaggc tggagtgcag tggcacgatc tcggctcact gaaagctctg    1380
cctcccggat tcatgccatt ctcctgcctc agcctcctga gtagctggga ctataggcac    1440
ccgccaccat gcccagctaa ttttttcgtat tttttttttta gtagagacgg ggtttcaccg    1500
tgttggccag gatggtcttg atctcctgac ctcgtgatct gcccgcctca gcctcccaaa    1560
gtgctgggat tacaggcgtg agccaccgtg cccgaccaag acttgtttcc taacaaacag    1620
ggccagttgc aatggctcat gcctataatc ctagcacttt gggaggccaa ggagggcaga    1680
tggcttgagg ccaggagttc gagattggcc tggacaacat ggtgaaaccc catctctaca    1740
aaaaaacaca aaaattagcc aggcatggtg gtgctggcct gttgtcccag ctacttggga    1800
agctgaggta ggagtatcac tttagctcag gaggtcaagg ttgcagtgag ccgagactgc    1860
accactgcac tccagcctga gcaacatggt gatacccgtc tcaaaaaata ataataacaa    1920
ataatgaata aatgcaattt attttaaagt gaaacttgca tttccttttt tagcctctgt    1980
acaaggaaaa atcattgctc ctcctatttc ctcaatctct ttccacttta ccacctgata    2040
aaattttact ttataaagca tgagagcaaa gctacctcct ccataacact ttcctctagc    2100
tctctcagcc caaagtgaat ttcccaacct cttaactcca aaatgaagtt gttaatgcct    2160
tgtgtagagc atacattcca tctcacatta tggttagttg ctgtacaaga ttagacattc    2220
cttaaataga gaaactattt cttattcact ataaccacaa aatgctctat ccttgccact    2280
catactataa accccctatgg ttctaggtcc tgcccaaaac ataaatgggt ggtatggacg    2340
ccgtatcacc ttactaaact gtgacatttt ggggattagg aacttttggc caagagggag    2400
actcacgcct ataattccaa cactttattt atttatttat ttttgagatg gcgtttcgct    2460
cttgttgtcc aggctggagt gcaatggcgc actctcagct caccgcaacc tccgcctccc    2520
aggttcaagc gattctcccg cctcagcctt ccaagtagct gggattacag gcacgtgcca    2580
ccacggcccg gctaatttttg tatttttagt agagatggag tttctccatg ttggttgggc    2640
tggtctcaaa ctcctgacct cagatgattc gcccgccttg gcctcccaaa gtgctgggat    2700
tgcaggtgtg agccactgcg ccaggcctca ttattattat tatttttttt gagaccaagt    2760
cttgctctgt tgcccaggct ggagtgcagt ggcactatct tggctcaccg caacctccgt    2820
ctcttgggtt caagcagttc tcctgtctca gcctccagag tagctggtat tacagatgcg    2880
caccaccaca cccatctaat ttttgtgttt ttagtagaga cagggtttcg ccatgtttcc    2940
caggctggtc tcaaactcct gggctcaagc gatccaccca cctcagcctc ccaaagtgct    3000
gggattattg gcatgaggca cagagcccgg tctgtaatcc caacactttg ggaggccaag    3060
gtaggaggat cacctgagtc caggagttca agaccggcct gggcaaaata gtgatacccc    3120
atctctacaa gaaataaaaa aattagccaa gtataggggc atgcacctgt gttcctcgct    3180
actcgcgagg ctgtggtggg aggatcactt cagcccagga ggttgaggca gcaatgagca    3240
ctgatggtgc cactgcactc cagcctgggt gacagggcaa gacctcatct caaaaaaata    3300
aataaaaagt gagcttgctc acctttccta tgtctctcag caccttgctt ttgaattttta    3360 gctattattt ttacagatct tttaacaaaa aggctgcttt aattaacgtt aactaacata    3420
catggcatat aagaagatcc ttgttctcaa gggctttaca aacctctaga gtcaaatgtg    3480
ccttattatc agtacaaaaa taaatggtgt cagctgggtg cagtgactca cacctgtaat    3540
```

```
cccagcactt taagaggctg aggcaggtgg atcacctgag gccaggagtt tgagaccagc    3600
ctggccaaca tggtgaaacc acattgtcag gcctctgagc ccaagccaag ccatcgcatc    3660
ccctgtgact tgcacgtata catccagatg gcctgaagta actgaagatc cacaaaagaa    3720
gtaaaaatag ccttaactga tgacattcca ccattgtgat tgtttctgc cccacccgaa     3780 ctgatcaatg tactttgtaa tctcccccac ccttaagaag gttctttgta attctcccca    3840
cccttgagaa tgtactttgt gagatccacc cctgcccaca aacattgct ctcaacttca     3900 ccacctatcc caaaacctgt aagaactaat gataatccat cacctttgc tgactctctt     3960 ttcggactca gcccgcctgc acccaggtga aataaacagc catgttgctc acacaaagcc    4020
tgtttggtgg tgtcttcaca cagacgcgca tgaaacacat ctctactaaa aatacaataa    4080
tcagctgggc gaggtggctc acagctgtaa tctcagcact tgggaggcc gagacaggca     4140 ggtcacttga ggccatgagt tcgagaccag cctggccaac atcgtgaaaa ccccatctct    4200
accaaaaata caaaaactag ccagatgtgg tggcgcacgc ctgtaatccc agctactcgg    4260
gaggctgagg taccgaatcg tctgaacgtg ggaagtggag cttgtagtga gccgagatcg    4320
ccccactgca ctccagcctg ggcaacagag ctagactgtc tcaaaacaaa caaaaaatgg    4380
tgtcaagact ctcagacgag attctaatgg attaaggcct atatgtaaat agcaccaaag    4440
actatggaac agagatggga gaagcaagca gggaggcagg aatagtttag ctgtggcagt    4500
tttagcttag tccacttaca taaatggttc tttagggtag cacgtggagc atcctcattt    4560
ccaaacattg gactgagagt agagagctgt gcaaaataac cacaagtccc caactatgcc    4620
ctcttaatta tccctatcat ctaagactgt tgttcccatc catcactgaa cttccccgtc    4680
ctcttccttc aacccctgtg ttagtcaatg gttgaaattt tgatttggta aaaaacctct    4740
ggcgaaaacc agcaaaaagg gctcacaaat caggtctcag ggaagcacag aggtagccac    4800
gagaaggccc gaggtgctca tggaaagagc tcgagcccag gagctctggg aggaccccag    4860
gcgctcggag ccgccgttac gtaaccggca ctcagagcct ccgaagaccg gaaggccccg    4920
ctcaggcccc ggctcaggcc ccggcccgg cccggccc ggcccgcc cggcccggcc         4980 gggcagctgg taggtgccgt gcgcaaccct ccggaagctg ccgccccttt cccttttat     5040 gggaatactt tttttaaaaa aaagagttc gctggcgcca ccccgtagga ctggccgccc     5100
taaaaccgtg ataaaggagc tgctcgccac ttctcacttc cgcttccttc cagtaaggag    5160
tcggggtctt ccccagtttt ctcagccagg cggcggcggc gactggcaat gtttggcctc    5220
aaaagaaacg cggtaatcgg actcaacctc tactgtgggg gggccggctt ggggccggc    5280 agcggcggcg ccacccgccc gggagggcga cttttggcta cggagaagga ggcctcggcc    5340
cggcgagaga taggggggagg ggaggccggc gcggtgattg gcggaagcgc cggcgcaagc   5400
cccccgtcca ccctcacgcc agactcccgg agggtcgcgc ggccgccgcc cattggcgcc    5460
gaggtccccg acgtcaccgc gaccccgcg aggctgcttt tcttcgcgcc cacccgccgc     5520
gcggcgccgc ttgaggagat ggaagccccg gccgctgacg ccatcatgtc gcccgaagag    5580
gagctggacg ggtacgagcc ggagcctctc gggaagcggc cggctgtcct gccgctgctg    5640
gagttggtcg gggaatctgg taataacacc agtacgacg ggtcactacc ctcgacgccg     5700
ccgccagcag aggaggagga ggacgagttg taccggcagt cgctggagat tatctctcgg    5760
taccttcggg agcaggccac cggcgccaag gacacaaagc caatgggcag gtctggggcc    5820
accagcagga aggcgctgga gaccttacga cgggttgggg atggcgtgca gcgcaaccac    5880
```

-continued

```
gagacggcct tccaaggtaa gggggttcat taatcgccaa ggcctcactc ccttttttcc    5940
atctctcccc ggactcaccc gccaagggtg ggttggaaac cgaaacgagt cagtgttgaa    6000
acgtgtctca tcctattcct gaagccagaa tattctggcc atgagtcatt gtttccgccc    6060
atcttgattc ttttggaaat ggcagctctt gttcaaagac cggaaagggt gggatgtcaa    6120
tttcaagtgg ggtcaacctg agttctgtaa atcccagtag cgattttccc gccgcgggtg    6180
ggcaggcgaa tcttgcgccg gtttagacaa aggaggccgt gaggacctgc atgcttttct    6240
ttctcaggca tgcttcggaa actggacatc aaaaacgaag acgatgtgaa atcgttgtct    6300
cgagtgatga tccatgtttt cagcgacggc gtaacaaact ggggcaggat tgtgactctc    6360
atttcttttg gtgcctttgt ggctaaacac ttgaagacca taaaccaaga aagctgcatc    6420
gaaccattag cagaaagtat cacagacgtt ctcgtaagga caaaacggga ctggctagtt    6480
aaacaaagag gctgggtaag tttgccttaa ggatgaaagg ggccttggag tggaagtaga    6540
atgaaggatt ttttttagag aggtggggat atctaaaggt ttttatgacg cacggctgtt    6600
tgcaggctct aactaaagga ccattgttta tttgatgttg atttaagtag tggatcctta    6660
gagatagtgg tatggcggtc ttgaattgta tcaaaaatct tggttttctc taggcaattt    6720
tttgttccaa ttcagttgaa tactcttcag tggattcaaa ccatgaaaaa ataagtcacc    6780
aggggaggat agctgaaata attcctaagg cggtgcctgt tttaatggag aagatatggg    6840
gtggagcctg cgttttaaac aaacccagat ctgatgcagg atgtacttaa ctacgttgag    6900
aaaaactgat ctgcgcaatt gaggcgttac tgaaatatta ggtggtggag atttgagaat    6960
aagggttttc gtcttttacc tcatgggaac tctggaagtc cttttgttag ataaatcct    7020 aataagacca agatagtact gtaaaatgaa gtttaattat catgggtccc cgcttaagaa    7080
actgaagaac ttatttttctt ttttttgcccc ggggtgaata ataattggtt tactattgct    7140
ttagggggaa accttagata ttttaattta ccttctctct ggatagtagt gttgtaagag    7200
agcagaaacc catacttgaa aatgtgcttt tcttttttgt tttctaggat ggggtttgtgg    7260 agttcttcca tgtagaggac ctagaaggtg gcatcaggaa tgtgctgctg gcttttgcag    7320
gtgttgctgg agtaggagct ggtttggcat atctaataag atagcctttac tgtaagtgca    7380 atagttgact tttaaccaac caccaccacc accaaaacca gtttatgcag ttggactcca    7440
agctgtaact tcctagagtt gcaccctagc aacctagcca gaaaagcaag tgcaagagg    7500 attatggcta acaagaataa atacatggga agagtgctcc ccattgattg aagagtcact    7560
gtctgaaaga agcaaagttc agtttcagca acaaacaaac tttgtttggg aagctatgga    7620
ggaggacttt tagatttagt gaagatggta gggtggaaag acttaatttc cttgttgaga    7680
acaggaaagt ggccagtagc caggcaagtc atagaattga ttacccgccg aattcattaa    7740
tttactgtag tgttaagaga agcactaaga atgccagtga cctgtgtaaa agttacaagt    7800
aatagaacta tgactgtaag cctcagtact gtacaaggga agcttttcct ctctctaatt    7860
agctttccca gtatacttct tagaaagtcc aagtgttcag gactttata cctgttatac    7920 tttggcttgg tttccatgat tcttacttta ttagcctagt ttatcaccaa taatacttga    7980
cggaaggctc agtaattagt tatgaatatg gatatcctca attcttaaga cagcttgtaa    8040
atgtatttgt aaaaattgta tatatttta cagaaagtct atttctttga aacgaaggaa    8100
gtatcgaatt tacattagtt ttttttcatac ccttttgaac tttgcaactt ccgtaattag    8160
gaacctgttt cttacagctt ttctatgcta aactttgttc tgttcagttc tagagtgtat    8220
acagaacgaa ttgatgtgta actgtatgca gactggttgt agtggaacaa atctgataac    8280
```

```
tatgcaggtt taaattttct tatctgattt tggtaagtat tccttagata ggttttttctt    8340 tgaaaacctg ggattgagag gttgatgaat ggaaattctt tcacttcatt atatgcaagt    8400
tttcaataat taggtctaag tggagtttta aggttactga tgacttacaa ataatgggct    8460
ctgattgggc aatactcatt tgagttcctt ccatttgacc taatttaact ggtgaaattt    8520
aaagtgaatt catgggctca tctttaaagc ttttactaaa agattttcag ctgaatggaa    8580
ctcattagct gtgtgcatat aaaaagatca catcaggtgg atggagagac atttgatccc    8640
ttgtttgctt aataaattat aaaatgatgg cttggaaaag caggctagtc taaccatggt    8700
gctattatta ggcttgcttg ttacacacac aggtctaagc ctagtatgtc aataaagcaa    8760
atacttactg ttttgtttct attaatgatt cccaaacctt gttgcaagtt tttgcattgg    8820
catctttgga tttcagtctt gatgtttgtt ctatcagact taacctttta tttcctgtcc    8880
ttccttgaaa ttgctgattg ttctgctccc tctacagata tttatatcaa ttcctacagc    8940
tttcccctgc catccctgaa ctctttctag ccctttaga ttttggcact gtgaaacccc      9000
tgctggaaac ctgagtgacc ctccctcccc accaagagtc cacagacctt tcatctttca    9060
cgaacttgat cctgttagca ggtggtaata ccatgggtgc tgtgacacta acagtcattg    9120
agaggtggga ggaagtccct ttccttgga ctggtatctt ttcaactatt gttttatcct      9180
gtctttgggg gcaatgtgtc aaaagtcccc tcaggaattt tcagaggaaa gaacatttta    9240
tgaggctttc tctaaagttt cctttgtata ggagtatgct cacttaaatt tacagaaaga    9300
ggtgagctgt gttaaacctc agagtttaaa agctactgat aaactgaaga agtgtctat      9360 attggaacta gggtcatttg aaagcttcag tctcggaaca tgacctttag tctgtggact    9420
ccatttaaaa ataggtatga ataagatgac taagaatgta atggggaaga actgccctgc    9480
ctgcccatct cagagccata aggtcatctt tgctagagct attttttacct atgtatttat   9540 cgttcttgat cataagccgc ttatttatat catgtatctc taaggaccta aaagcacttt    9600
atgtagtttt taattaatct taagatctgg ttacggtaac taaaaaagcc tgtctgccaa    9660
atccagtgga aacaagtgca tagatgtgaa ttggttttta ggggcccccac ttcccaattc   9720 attaggtatg actgtggaaa tacagacaag gatcttagtt gatattttgg gcttggggca    9780
gtgagggctt aggacacccc aagtggtttg ggaaaggagg aggggagtgg tgggtttata    9840
gggggaggag gaggcaggtg gtctaagtgc tgactggcta cgtagttcgg gcaaatcctc    9900
caaaagggaa agggaggatt tgcttagaag gatggcgctc ccagtgacta cttttttgact  9960 tctgtttgtc ttacgcttct ctcagggaaa aacatgcagt cctctagtgt tcatgtaca     10020 ttctgtgggg ggtgaacacc ttggttctgg ttaaacagct gtacttttga tagctgtgcc    10080
aggaagggtt aggaccaact acaaattaat gttggttgtc aaatgtagtg tgtttcccta    10140
actttctgtt tttcctgaga aaaaaaaata aatctttttat tcaaatacag ggtgtgatat   10200
gggtcttttc tcatcgacgc ctctttttcc ttccctctct taggcaaacc ttttagaaa      10260 gtcagctgag caaatatgta caggtgaatt caaagcaaaa gcctcacaaa gttgatttgc    10320
cttagagcaa aggacagttc ctttcttcaa ttctaattag aggtgttggg ttttaatta     10380 aatatattac tgctgtactt agaggagttc ttaaacctcc aagtaaaatc aaaaacctct    10440
ttaaaatcaa aatttctgtc ttgatttatt tatttattat tttttttttg agatggagtt    10500
ttgctcttgt tgtccaggct ggagtgcaat ggcacgatct ccgctcaccg caacctccgc    10560
ctcccaggtt caaatgattc tcctgcctca gcctcctgag tagctgggaa tacaggcatg    10620
```

-continued

```
cgccaccaca cccagataat tttgtatttt tagtagagat ggggtttctc cgtgttggtc    10680
aggctggtct tgaactcccg acctcaggtg atctgcccac ctctgcctcc cagagtgcca    10740
ggattacagg cgtgagccat cgcacccagc ctctgtcttg attttttga atcaccaggt     10800
gttggtatgt tttgttttgt tttgttttga ggcacagtct cactcttttg cccaggctag    10860
agtgcagtgg ggcaatctcg gctcactgca acctcagcct cccgagtagc tgggattaca    10920
ggtgcccgcc accatgcccg gctaattttt ctattttgg tagagacggg gttttgccgt     10980
gttggtcagg ctggtcttga agtcctgacc tcagtgatcc actcgcctca gccgaagtgc    11040
tgcgattaca gacctgagcc actgcgccca gccttgatct tgaggtaaga gggtactgta    11100
cagcagttac tctatcataa cacctaaata atacctaaag ttaaagagtt ttgatgaagt    11160
tcttggcagc agtgcttttc cccttctgct ttccaaaagg aggtaaaaag aagccagtca    11220
atttcaaaaa cccctatcct gcttttattt tcagctacct tgaaagtgag ctgaatcacc    11280
atggaaatgt gcaaatgtga ggtttgcata cttggtttta agccctgagc accatatgct    11340
aatcaggcaa tcaggattct gtgcctccct gcagtcagtt gcatttctat ttaaaagtgc    11400
attttggttt ggaagcccct ttctggagcc taactaccaa aaggcagcaa ctttttgtat    11460
cattacaaag aaagctgtgt aagtgcactc ccaagcaaag gtgtggtagg agagtagcag    11520
ccacagagga cccaagccca agtcttggcc tgagttaagt tagtgctatt gctcccattg    11580
acgtgctatg atgtgaagcc gtttctggta cagtgttcct ttgctcagca ccttaaaagc    11640
ttggatttaa tagtaactgg gtaaccttaa tcagtagtca gaattatcaa cactttgctt    11700
tatttgacac aaccagactt tctcagttcc tgttctgtat ctagagcaac gtcttcatac    11760
tgttttttca caaattttt atttaaaaca gttgtgacag ccgaaggatt ttttttttt      11820
tttttacaaa attaaaatga aataacttgt acaactggtg cgtaccatgg ctccagccag    11880
atgcccaaag cactggctat taattcctgg agttcagatg gtcagttgag tctatcctag    11940
ttttttgctt cacttgttca atcatggaac tttctagaac gctgccactc ttcaaaggct    12000
tctcaatttc aaatttgaaa acttaattct ctccctctta gtttcaaagt tgttacagtg    12060
ttatctatgt gaagtatgtg gaagttggg ggctggggat tttcctccag gcagattaag     12120
aaacagctct ccgggtcggg cgctgtggct caggcctgta atcccagcac tttgggaggc    12180
tgaggcagga ga                                                         12192
```

<210> SEQ ID NO 12
<211> LENGTH: 328
<212> TYPE: PRT
<213> ORGANISM: Homo sapiens

<400> SEQUENCE: 12

```
Met Glu Ala Asn Gly Ser Gln Gly Thr Ser Gly Ser Ala Asn Asp Ser
1               5                   10                  15

Gln His Asp Pro Gly Lys Met Phe Ile Gly Gly Leu Ser Trp Gln Thr
            20                  25                  30

Ser Pro Asp Ser Leu Arg Asp Tyr Phe Ser Lys Phe Gly Glu Ile Arg
        35                  40                  45

Glu Cys Met Val Met Arg Asp Pro Thr Thr Lys Arg Ser Arg Gly Phe
    50                  55                  60

Gly Phe Val Thr Phe Ala Asp Pro Ala Ser Val Asp Lys Val Leu Gly
65                  70                  75                  80

Gln Pro His His Glu Leu Asp Ser Lys Thr Ile Asp Pro Lys Val Ala
                85                  90                  95
```

```
Phe Pro Arg Arg Ala Gln Pro Lys Met Val Thr Arg Thr Lys Lys Ile
                100                 105                 110

Phe Val Gly Gly Leu Ser Ala Asn Thr Val Val Glu Asp Val Lys Gln
            115                 120                 125

Tyr Phe Glu Gln Phe Gly Lys Val Glu Asp Ala Met Leu Met Phe Asp
        130                 135                 140

Lys Thr Thr Asn Arg His Arg Gly Phe Gly Phe Val Thr Phe Glu Asn
145                 150                 155                 160

Glu Asp Val Val Glu Lys Val Cys Glu Ile His Phe His Glu Ile Asn
                165                 170                 175

Asn Lys Met Val Glu Cys Lys Lys Ala Gln Pro Lys Glu Val Met Phe
            180                 185                 190

Pro Pro Gly Thr Arg Gly Arg Ala Arg Gly Leu Pro Tyr Thr Met Asp
        195                 200                 205

Ala Phe Met Leu Gly Met Gly Met Leu Gly Tyr Pro Asn Phe Val Ala
210                 215                 220

Thr Tyr Gly Arg Gly Tyr Pro Gly Phe Ala Pro Ser Tyr Gly Tyr Gln
225                 230                 235                 240

Phe Pro Gly Phe Pro Ala Ala Ala Tyr Gly Pro Val Ala Ala Ala Ala
                245                 250                 255

Val Ala Ala Ala Arg Gly Ser Gly Ser Asn Pro Ala Arg Pro Gly Gly
            260                 265                 270

Phe Pro Gly Ala Asn Ser Pro Gly Pro Val Ala Asp Leu Tyr Gly Pro
        275                 280                 285

Ala Ser Gln Asp Ser Gly Val Gly Asn Tyr Ile Ser Ala Ala Ser Pro
290                 295                 300

Gln Pro Gly Ser Gly Phe Gly His Gly Ile Ala Gly Pro Leu Ile Ala
                305                 310                 315                 320

Thr Ala Phe Thr Asn Gly Tyr His
            325

<210> SEQ ID NO 13
<211> LENGTH: 1581
<212> TYPE: DNA
<213> ORGANISM: Homo sapiens

<400> SEQUENCE: 13
ctcgccgctg ccccggctcc gccgctcgca gagagattcg gaggagcccg gcgggggggg       60
aggaggaggg ggaggaggga gcggagatct cggggctcgg agccggccgc cgctccgctc      120
cgatcgctgt ggggcttggt tttttggggg tggggggcg ggggggctca gatatggagg       180
caaatgggag ccaaggcacc tcgggcagcg ccaacgactc ccagcacgac cccggtaaaa      240
tgtttatcgg tggactgagc tggcagacct caccagatag ccttagagac tattttagca      300
aatttggaga aattagagaa tgtatggtca tgagagatcc cactacgaaa cgctccagag      360
gcttcggttt cgtcacgttc gcagacccag caagtgtaga taaagtatta ggtcagcccc      420
accatgagtt agattccaag acgattgacc ccaaagttgc atttcctcgt cgagcgcaac      480 ccagatggt cacaagaaca aagaaaatat ttgtaggcgg ttatctgcg aacacagtag        540 tggaagatgt aaagcaatat ttcgagcagt ttggcaaggt ggaagatgca atgctgatgt      600
ttgataaaac taccaacagg cacagagggt ttggctttgt cactttttga aatgaagatg     660
ttgtggagaa agtctgtgag attcatttcc atgaaatcaa taataaaatg gtagaatgta     720
agaaagctca gccgaaagaa gtcatgttcc cacctgggac aagaggccgg gcccggggac     780
```

-continued

```
tgccttacac catggacgcg ttcatgcttg gcatggggat gctgggatat cccaacttcg      840
tggcgaccta tggccgtggc tacccggat ttgctccaag ctatggctat cagttcccag        900
gcttcccagc agcggcttat ggaccagtgg cagcagcggc ggtggcggca gcaagaggat      960
caggctccaa cccggcgcgg cccggaggct tcccgggggc caacagccca ggacctgtcg      1020
ccgatctcta cggccctgcc agccaggact ccggagtggg gaattacata agtgcggcca      1080
gcccacagcc gggctcgggc ttcggccacg gcatagctgg acctttgatt gcaacggcct      1140
ttacaaatgg ataccattga gcaggtgctt tcgttgccat ctcactctga gcatacct        1200 ggatgtccag gcaagactgg gcgaagtttc tgagtggccc tttgtttagg tgatgtcctc      1260
agacctggac ccccaccagc ctcactcccc atcccaacca gagatggctc acttcggatc      1320
gagggttgac tacatctcat catctcacga atctgctgta atataagaca acagcttta      1380 aatgtgtata taacccatga tttcggtttt gttttgtttt gttttcttg atggtttccc       1440 tctccctccc tctcttccca ttctccttttt aaatctcttt gaatcacatt tggtagtgat    1500
tttgacttag tccagtagtc acatagcttt aatatctagt tcaaagctaa ccatagtata    1560
attgttatat taaggagtta t                                                 1581
```

<210> SEQ ID NO 14
<211> LENGTH: 480
<212> TYPE: PRT
<213> ORGANISM: Homo sapiens

<400> SEQUENCE: 14

```
Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220
```

```
Phe Val Met Glu Tyr Ala Asn Gly Gly Glu Leu Phe His Leu Ser
225                 230                 235                 240

Arg Glu Arg Val Phe Ser Glu Asp Arg Ala Arg Phe Tyr Gly Ala Glu
            245                 250                 255

Ile Val Ser Ala Leu Asp Tyr Leu His Ser Glu Lys Asn Val Val Tyr
        260                 265                 270

Arg Asp Leu Lys Leu Glu Asn Leu Met Leu Asp Lys Asp Gly His Ile
    275                 280                 285

Lys Ile Thr Asp Phe Gly Leu Cys Lys Glu Gly Ile Lys Asp Gly Ala
290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
            325                 330                 335

Val Val Met Tyr Glu Met Met Cys Gly Arg Leu Pro Phe Tyr Asn Gln
        340                 345                 350

Asp His Glu Lys Leu Phe Glu Leu Ile Leu Met Glu Glu Ile Arg Phe
    355                 360                 365

Pro Arg Thr Leu Gly Pro Glu Ala Lys Ser Leu Leu Ser Gly Leu Leu
370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
            405                 410                 415

Tyr Glu Lys Lys Leu Ser Pro Pro Phe Lys Pro Gln Val Thr Ser Glu
        420                 425                 430

Thr Asp Thr Arg Tyr Phe Asp Glu Glu Phe Thr Ala Gln Met Ile Thr
    435                 440                 445

Ile Thr Pro Pro Asp Gln Asp Asp Ser Met Glu Cys Val Asp Ser Glu
450                 455                 460

Arg Arg Pro His Phe Pro Gln Phe Ser Tyr Ser Ala Ser Gly Thr Ala
465                 470                 475                 480

<210> SEQ ID NO 15
<211> LENGTH: 3008
<212> TYPE: DNA
<213> ORGANISM: Homo sapiens

<400> SEQUENCE: 15
taattatggg tctgtaacca ccctggactg ggtgctcctc actgacggac ttgtctgaac     60
ctctctttgt ctccagcgcc cagcactggg cctggcaaaa cctgagacgc ccggtacatg    120
ttggccaaat gaatgaacca gattcagacc ggcaggggcg ctgtggttta ggagggcct    180 ggggtttctc ccaggaggtt tttgggcttg cgctggaggg ctctggactc ccgtttgcgc    240
cagtggcctg catcctggtc ctgtcttcct catgtttgaa tttctttgct ttccctagtct    300 ggggagcagg gaggagccct gtgccctgtc ccaggatcca tgggtaggaa ccatggac      360 agggagagca acggggccat ctgtcacca ggggcttagg aaggccgag ccagcctggg      420 tcaaagaagt caaggggct gcctggagga ggcagcctgt cagctggtgc atcagaggct    480
gtggccaggc cagctgggct cggggagcgc cagcctgaga ggagcgcgtg agcgtcgcgg    540
gagcctcggg caccatgagc gacgtggcta ttgtgaagga gggttggctg cacaaacgag    600
gggagtacat caagacctgg cggccacgct acttcctcct caagaatgat ggcacccttca   660 ttggctacaa ggagcggccg caggatgtgg accaacgtga ggctcccctc aacaacttct   720
```

```
ctgtggcgca gtgccagctg atgaagacgg agcggccccg gcccaacacc ttcatcatcc    780
gctgcctgca gtggaccact gtcatcgaac gcaccttcca tgtggagact cctgaggagc    840
gggaggagtg gacaaccgcc atccagactg tggctgacgg cctcaagaag caggaggagg    900
aggagatgga cttccggtcg ggctcaccca gtgacaactc aggggctgaa gagatggagg    960
tgtccctggc caagcccaag caccgcgtga ccatgaacga gtttgagtac ctgaagctgc   1020
tgggcaaggg cactttcggc aaggtgatcc tggtgaagga aaggccaca ggccgctact   1080
acgccatgaa gatcctcaag aaggaagtca tcgtggccaa ggacgaggtg gcccacacac   1140
tcaccgagaa ccgcgtcctg cagaactcca ggcacccctt cctcacagcc ctgaagtact   1200
ctttccagac ccacgaccgc ctctgctttg tcatggagta cgccaacggg gcgagctgt   1260
tcttccacct gtcccgggag cgtgtgttct ccgaggaccg ggcccgcttc tatgcgctg   1320
agattgtgtc agccctggac tacctgcact cggagaagaa cgtggtgtac cgggacctca   1380
agctggagaa cctcatgctg gacaaggacg ggcacattaa gatcacagac ttcgggctgt   1440
gcaaggaggg gatcaaggac ggtgccacca tgaagacctt ttgcggcaca cctgagtacc   1500
tggcccccga ggtgctggag gacaatgact acggccgtgc agtggactgg tggggctgg   1560
gcgtggtcat gtacgagatg atgtgcggtc gcctgcccct ctacaaccag gaccatgaga   1620
agcttttgga gctcatcctc atggaggaga tccgcttccc gcgcacgctt ggtcccgagg   1680
ccaagtcctt gctttcaggg ctgctcaaga aggaccccaa gcagaggctt ggcggggct   1740
ccgaggacgc caaggagatc atgcagcatc gcttctttgc cggtatcgtg tggcagcacg   1800
tgtacgagaa gaagctcagc ccaccccttca agccccaggt cacgtcggag actgacacca   1860
ggtattttga tgaggagttc acggcccaga tgatcaccat cacaccaccct gaccaagatg   1920
acagcatgga gtgtgtggac agcgagcgca ggccccactt cccccagttc tcctactcgg   1980
ccagcggcac ggcctgaggc ggcggtggac tgcgctggac gatagcttgg agggatggag   2040
aggcggcctc gtgccatgat ctgtatttaa tggttttttat ttctcgggtg catttgagag   2100
aagccacgct gtcctctcga gcccagatgg aaagacgttt ttgtgctgtg gcagcaccc   2160
tcccccgcag cggggtaggg aagaaaacta tcctgcgggt tttaatttat ttcatccagt   2220
ttgttctccg ggtgtggcct cagccctcag aacaatccga ttcacgtagg gaaatgttaa   2280
ggacttctgc agctatgcgc aatgtggcat tgggggggccg ggcaggtcct gcccatgtgt   2340
cccctcactc tgtcagccag ccgccctggg ctgtctgtca ccagctatct gtcatctctc   2400
tggggcctg gcctcagtt caacctggtg gcaccagatg caacctcact atggtatgct   2460
ggccagcacc ctctcctggg ggtggcaggc acacagcagc ccccagcac taaggccgtg   2520
tctctgagga cgtcatcgga ggctgggccc tgggatggg accagggatg ggggatgggc   2580
cagggtttac ccagtgggac agaggagcaa ggtttaaatt tgttattgtg tattatgttg   2640
ttcaaatgca ttttggggt ttttaatctt tgtgacagga aagccctccc ccttcccctt   2700
ctgtgtcaca gttcttggtg actgtcccac cgggagcctc cccctcagat gatctctcca   2760
cggtagcact tgaccttttc gacgcttaac ctttccgctg tcgccccagg ccctcctga   2820
ctccctgtgg gggtggccat ccctgggccc ctccacgcct cctggccaga cgctgccgct   2880
gccgctgcac cacggcgttt ttttacaaca ttcaacttta gtattttttac tattataata   2940
taatatggaa ccttccctcc aaattcttca ataaagttg ctttttcaaaa aaaaaaaaaa   3000
aaaaaaaa                                                           3008
```

<210> SEQ ID NO 16
<211> LENGTH: 419
<212> TYPE: PRT
<213> ORGANISM: Homo sapiens

<400> SEQUENCE: 16

```
Met Lys Thr Glu Arg Pro Arg Pro Asn Thr Phe Val Ile Arg Cys Leu
1               5                   10                  15

Gln Trp Thr Thr Val Ile Glu Arg Thr Phe His Val Asp Ser Pro Asp
            20                  25                  30

Glu Arg Glu Glu Trp Met Arg Ala Ile Gln Met Val Ala Asn Ser Leu
        35                  40                  45

Lys Gln Arg Ala Pro Gly Glu Asp Pro Met Asp Tyr Lys Cys Gly Ser
    50                  55                  60

Pro Ser Asp Ser Ser Thr Thr Glu Glu Met Glu Val Ala Val Ser Lys
65                  70                  75                  80

Ala Arg Ala Lys Val Thr Met Asn Asp Phe Asp Tyr Leu Lys Leu Leu
                85                  90                  95

Gly Lys Gly Thr Phe Gly Lys Val Ile Leu Val Arg Glu Lys Ala Thr
            100                 105                 110

Gly Arg Tyr Tyr Ala Met Lys Ile Leu Arg Lys Glu Val Ile Ile Ala
        115                 120                 125

Lys Asp Glu Val Ala His Thr Val Thr Glu Ser Arg Val Leu Gln Asn
    130                 135                 140

Thr Arg His Pro Phe Leu Thr Ala Leu Lys Tyr Ala Phe Gln Thr His
145                 150                 155                 160

Asp Arg Leu Cys Phe Val Met Glu Tyr Ala Asn Gly Gly Glu Leu Phe
                165                 170                 175

Phe His Leu Ser Arg Glu Arg Val Phe Thr Glu Glu Arg Ala Arg Phe
            180                 185                 190

Tyr Gly Ala Glu Ile Val Ser Ala Leu Glu Tyr Leu His Ser Arg Asp
        195                 200                 205

Val Val Tyr Arg Asp Ile Lys Leu Glu Asn Leu Met Leu Asp Lys Asp
    210                 215                 220

Gly His Ile Lys Ile Thr Asp Phe Gly Leu Cys Lys Glu Gly Ile Ser
225                 230                 235                 240

Asp Gly Ala Thr Met Lys Thr Phe Cys Gly Thr Pro Glu Tyr Leu Ala
                245                 250                 255

Pro Glu Val Leu Glu Asp Asn Asp Tyr Gly Arg Ala Val Asp Trp Trp
            260                 265                 270

Gly Leu Gly Val Val Met Tyr Glu Met Met Cys Gly Arg Leu Pro Phe
        275                 280                 285

Tyr Asn Gln Asp His Glu Arg Leu Phe Glu Leu Ile Leu Met Glu Glu
    290                 295                 300

Ile Arg Phe Pro Arg Thr Leu Ser Pro Glu Ala Lys Ser Leu Leu Ala
305                 310                 315                 320

Gly Leu Leu Lys Lys Asp Pro Lys Gln Arg Leu Gly Gly Gly Pro Ser
                325                 330                 335

Asp Ala Lys Glu Val Met Glu His Arg Phe Phe Leu Ser Ile Asn Trp
            340                 345                 350

Gln Asp Val Val Gln Lys Lys Leu Leu Pro Pro Phe Lys Pro Gln Val
        355                 360                 365

Thr Ser Glu Val Asp Thr Arg Tyr Phe Asp Asp Glu Phe Thr Ala Gln
    370                 375                 380
```

```
Ser Ile Thr Ile Thr Pro Pro Asp Arg Tyr Asp Ser Leu Gly Leu Leu
385                 390                 395                 400

Glu Leu Asp Gln Arg Thr His Phe Pro Gln Phe Ser Tyr Ser Ala Ser
            405                 410                 415

Ile Arg Glu

<210> SEQ ID NO 17
<211> LENGTH: 5280
<212> TYPE: DNA
<213> ORGANISM: Homo sapiens

<400> SEQUENCE: 17
```

| | | | | | |
|---|---|---|---|---|---|
| tgggaggggg | cggtaagcgg | gggctggggg | gaggggcgg | gggggccgc | gccgtgctag | 60 |
| ccgttgggcc | tgcctcggag | gaggcgtcgc | cgccgccgct | gccgctgccg | gcgccgttgc | 120 |
| cgctgccggg | aaacacaagg | aaagggaacc | agcgcagcgt | ggcgatgggc | gggggtagag | 180 |
| ccccgccgga | gaggctgggc | ggctgccggt | gacagactgt | gccctgtcca | cggtgcctcc | 240 |
| tgcatgtcct | gctgccctga | gctgtcccga | gctaggtgac | agcgtaccac | gctgccacca | 300 |
| tgaatgaggt | gaatacatca | agacctggag | gccacggtac | ttcctgctga | gagcgacgg | 360 |
| ctccttcatt | gggtacaagg | agaggcccga | ggcccctgat | cagactctac | ccccttaaa | 420 |
| caacttctcc | gtagcagaat | gccagctgat | gaagaccgag | aggccgcgac | ccaacacctt | 480 |
| tgtcatacgc | tgcctgcagt | ggaccacagt | catcgagagg | accttccacg | tggattctcc | 540 |
| agacgagagg | gaggagtgga | tgcgggccat | ccagatggtc | gccaacagcc | tcaagcagcg | 600 |
| ggccccaggc | gaggaccca | tggactacaa | gtgtggctcc | cccagtgact | cctccacgac | 660 |
| tgaggagatg | gaagtggcgg | tcagcaaggc | acgggctaaa | gtgaccatga | atgacttcga | 720 |
| ctatctcaaa | ctccttggca | agggaacctt | tggcaaagtc | atcctggtgc | gggagaaggc | 780 |
| cactggccgc | tactacgcca | tgaagatcct | gcggaaggaa | gtcatcattg | ccaaggatga | 840 |
| agtcgctcac | acagtcaccg | agagccgggt | cctccagaac | accaggcacc | cgttcctcac | 900 |
| tgcgctgaag | tatgccttcc | agacccacga | ccgcctgtgc | tttgtgatgg | agtatgccaa | 960 |
| cgggggtgag | ctgttcttcc | acctgtcccg | ggagcgtgtc | ttcacagagg | agcgggcccg | 1020 |
| gttttatggt | gcagagattg | tctcggctct | tgagtacttg | cactcgcggg | acgtggtata | 1080 |
| ccgcgacatc | aagctggaaa | acctcatgct | ggacaaagat | ggccacatca | agatcactga | 1140 |
| ctttggcctc | tgcaaagagg | gcatcagtga | cggggccacc | atgaaaacct | tctgtgggac | 1200 |
| cccggagtac | ctggcgcctg | aggtgctgga | ggacaatgac | tatggccggg | ccgtggactg | 1260 |
| gtgggggctg | ggtgtggtca | tgtacgagat | gatgtgcggc | cgcctgccct | tctacaacca | 1320 |
| ggaccacgag | cgcctcttcg | agctcatcct | catggaagag | atccgcttcc | cgcgcacgct | 1380 |
| cagccccgag | gccaagtccc | tgcttgctgg | gctgcttaag | aaggacccca | agcagaggct | 1440 |
| tggtgggggg | cccagcgatg | ccaaggagg | catggagcac | aggttcttcc | tcagcatcaa | 1500 |
| ctggcaggac | gtggtccaga | agaagctcct | gccaccctc | aaacctcagg | tcacgtccga | 1560 |
| ggtcgacaca | aggtacttcg | atgatgaatt | taccgcccag | tccatcacaa | tcacaccccc | 1620 |
| tgaccgctat | gacagcctgg | gcttactgga | gctggaccag | cggaccccact | tccccagtt | 1680 |
| ctcctactcg | gccagcatcc | gcgagtgagc | agtctgccca | cgcagaggac | gcacgctcgc | 1740 |
| tgccatcacc | gctgggtggt | ttttccccc | taacttttta | cttagccttt | ttggtttgtg | 1800 |
| tccccacccc | cacctcctca | cccccttcc | agttcttctt | caggcccctc | ccagacgcac | 1860 |

```
cccagcggcc cctgcagccc ctgcctccag cctccagcct cacctttgtg cccagactcg    1920
catttggaag actccacctc ccgcccaggc ctgggctgtt gggcggttgg agattcaggt    1980
tttaatccac acaagcccca gtgaggggtg aagcatggcg cctggggcct gcctgagttt    2040
ctggcctggg tgtcgtgctg gtgtctgcct ccgcgctgct gcatctggac gaaggctgcc    2100
ttctggtggg acgcgacacc cggcagacag tggtgctgcc ttccaggccc cgtggcctag    2160
gctcggagtg gccaggcacg gggcggtcca atccccacc cgctgtcccc ctatgggggc     2220
agaaaagcaa taatgtccag gggcaggcag gggcccttgg gagctgcagg gctgggggtt    2280
agggctgctc cctggtgaat ggagtcagat cctaggatct gtaccatggg gaaccaggag    2340
tggccgggct gggtgccgcc tcctggtccg gcctcctccc caccaaactg tcctcaccct    2400
atggatgagg caggaggaac atttggggcc aaacctgcct gcctcccagc ccgtgccctt    2460
actagggctt ccttccagct ggccttacct cccgctggac cctgggcctg gctggcccc    2520 actgggggct atgggctggg ctcaccctct cctctgcggg ggtggagggc caccagcctt    2580
ggctgttaca atcttacacc ggacagtatt gggcccatg gacttggtca gggagggtg     2640 ggggtgggca tctctggtac ctattggggt gggggcctc tgaaaaggga ggctcctagg     2700
cccccctcac ccctccctct ccccaggcc ccacgttctg cagccttaag gttgaacatg     2760
agtgcacgtc catgtcagtg ctgtgggact cctgtgcgtg cctcggactg cgtgtgtcgg    2820
cgggacgcag gcacacgtgg gtgtgtgtgc atgtgtgttt gtgtgagggc agcgtgtcct    2880
ccagtgtgca tggtgtgtgg gcttgggccc catccctggc ccgagcattt catcctgtgg    2940
gggaggggtg ctgacctagt gggaggagcc ccactgtgat ccatgagctg ccctgcccac    3000
gcctcccctc cctgtagcaa cacctctggg tgtttggagt ttagcttttg tgggtttgct    3060
ctccctatcc catctcctgt actacacagt tcatggcagg gtggggaggg gtggggttgg    3120
ttcgggtggg tgagggtctt tttcctctgt gtgcgatgtt gttatctgac agttctccgt    3180
ccctactggc ctttctcctc gtcttcatat ttgtacggta caagcaataa agacactcat    3240
ttcagaccag ggcccagcct gcactcacgc cagcccaacc actctgggct ttgccttggt    3300
gatggagtca gacccctggg ccccagctcc tcctgtacta gccgttccct tcagcaagga    3360
gggcactgag ctcagggtga gggcagctgg ggtgtgtgca ggagctcagg ctggagaggg    3420
tgggtggagc tggtgctgtg gggctgaggg gtatgggaag gctccccgca tgtgggggtg    3480
gggtggacag agaccactcc aggccctcag tgctgcttag gctaagagag gtggggtgga    3540
gggacagggc tggaagatct gggtagccca gaatgaggag ggtgcctgtg ctgtcactga    3600
atgagaggga gtggttcatt ccacccggct gccgagcctc agagggggc attcctatcc     3660 tgccccacct ccctgtttat gctgccacct ggaagcttg aggcccccaa attccagtac     3720
agacccagtg gtgtgttcat ggtggcgtgg ttgctgtcac ctgggagctc ctgagcgttt    3780
ggttagaacc ctgttcagct tggggtcagc cctcccctag tcactgccct ttagcctgga    3840
tgtgtctggg cccctgcact tcccgtgctt gagtcacgtg gctgcatggc cgggcgctgg    3900
ccggatggaa cacctccccc agcaagggac cagggaccag agccctggcc tgccctgctg    3960
agccctgctg tgcagagggc ctggcacaga tgaatttgag attttgccgc aaggtgttag    4020
cacttcacac ccattgagtc tttgagattt taagtgaatg taagcagaaa aagtcagatc    4080
caatttacag aaatcagagt tagctacagc taggactcgt ttggttgggg ttttttagtt    4140
tgtctttcta aagtcatgtg gaccttaatt taattacaaa agtctaccct ggtggtcata    4200
aaataggcag gcctatgaag aaaggccttt tactcttcca tctcatccca gccccgagtt    4260
```

-continued

```
gacccacgtt gctgctcctc acaccatggt gatgcaggtc tcgtagtgtg ggcacaggcc    4320
tggctacctc atcttttag tgcctctctc ctcttccaca ggatgggtc ccacagctgc    4380
agcagctggc cccgtagttg agcatgtgtg gttatcctgt agagcttttc ccaagaaggg    4440
tgtttgaact tagagtctta ataaaatctt accaaataaa ttttgagtag aataatcgtc    4500
ttttgcaatg tacattttaa aaatttcaca cattctttt tgtatataaa gaacagtgac    4560
tgggcacagt ggctcatgcc tgtaatccca gcaatttggg aggccgaggc gggcgggtct    4620
cttgaggcca ggggttcgag accagcctgg gcatcatagg gagaccttca tctctacaaa    4680
aaatacaaaa attagctggg catggtggtg catgcctgca atcccagcta acttggaagg    4740
ctgaggtgag gtgggaagat cacttgagcc caggagtttg aggctgcagt gagctatgat    4800
tgcggcactg cactgcagcc tgggacaatg agactgtgtc tctaaaaata aaaaaaaaa    4860
aaacatgata catgctatta aaaagacag caaagcagga gtataagaaa ggaaattcac    4920
ccgaggtcgc agggccttga gtactcattt tggtgctgat tacctctctg caaatggaca    4980
cggcatcata aattggtagt ttcctgctct ttttgtgtaa tcttttccag ttaatgtgaa    5040
gcctctgggg gctgccctcg tgcactgatg gttgtgtgga gtcggggcg gcagtgcgat    5100
tccctttag ctgctgcatg gggggaactc aggctttcca gctgcttcct ggggttccat    5160
ggggtagacc cctcaaccgc ttcagctgcc ccgttaacag gaattgactt ggtttcgttt    5220
ggtgctacca gcagtcctgt aataaactag ctatccatct gtaaaaaaa aaaaaaaaaa    5280
```

```
<210> SEQ ID NO 18
<211> LENGTH: 433
<212> TYPE: PRT
<213> ORGANISM: Homo sapiens

<400> SEQUENCE: 18
```

```
Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190
```

```
Thr Ala Val Leu Lys Leu Cys Asp Phe Gly Ser Ala Lys Gln Leu Val
            195                 200                 205
Arg Gly Glu Pro Asn Val Ser Tyr Ile Cys Ser Arg Tyr Tyr Arg Ala
        210                 215                 220
Pro Glu Leu Ile Phe Gly Ala Thr Asp Tyr Thr Ser Ile Asp Val
225                 230                 235                 240
Trp Ser Ala Gly Cys Val Leu Ala Glu Leu Leu Gly Gln Pro Ile
                    245                 250                 255
Phe Pro Gly Asp Ser Gly Val Asp Gln Leu Val Glu Ile Lys Val
                260                 265                 270
Leu Gly Thr Pro Thr Arg Glu Gln Ile Arg Glu Met Asn Pro Asn Tyr
            275                 280                 285
Thr Glu Phe Lys Phe Pro Gln Ile Lys Ala His Pro Trp Thr Lys Asp
        290                 295                 300
Ser Ser Gly Thr Gly His Phe Thr Ser Gly Val Arg Val Phe Arg Pro
305                 310                 315                 320
Arg Thr Pro Pro Glu Ala Ile Ala Leu Cys Ser Arg Leu Leu Glu Tyr
                    325                 330                 335
Thr Pro Thr Ala Arg Leu Thr Pro Leu Glu Ala Cys Ala His Ser Phe
                340                 345                 350
Phe Asp Glu Leu Arg Asp Pro Asn Val Lys Leu Pro Asn Gly Arg Asp
            355                 360                 365
Thr Pro Ala Leu Phe Asn Phe Thr Gln Glu Leu Ser Ser Asn Pro
        370                 375                 380
Pro Leu Ala Thr Ile Leu Ile Pro Pro His Ala Arg Ile Gln Ala Ala
385                 390                 395                 400
Ala Ser Thr Pro Thr Asn Ala Thr Ala Ala Ser Asp Ala Asn Thr Gly
                    405                 410                 415
Asp Arg Gly Gln Thr Asn Asn Ala Ala Ser Ala Ser Ala Ser Asn Ser
                420                 425                 430
Thr

<210> SEQ ID NO 19
<211> LENGTH: 7134
<212> TYPE: DNA
<213> ORGANISM: Homo sapiens

<400> SEQUENCE: 19
cgggcttgtg ccgccgccgc cgccgccgcc gcccgggcca agtgacaaag gaaggaagga      60
agcgaggagg agccggcccc gcagccgctg acagggctct gggctggggc aaagcgcgga     120
cacttcctga gcgggcaccg agcagagccg aggggcggga gggcggccga gctgttgccg     180
cggacggggg aggggcccc gagggacgga agcggttgcc gggttcccat gtccccggcg     240
aatgggaac agtcgaggag ccgctgcctg gggtctgaag ggagctgcct ccgccaccgc     300
catggccgct ggatccagcc gccgcctgca gctgctcctg gcgcaatgag gagaggagcc     360
gccgccaccg ccaccgcccg cctctgactg actcgcgact ccgccgccct ctagttcgcc     420
gggcccctgc cgtcagcccg ccggatcccg cggcttgccg gagctgcagc gtttccgtc     480
gcatctccga gccacccct ccctccctct cctccctcc tacccatccc cctttctctt      540
caagcgtgag actcgtgatc cttccgccgc ttcccttctt cattgactcg gaaaaaaat      600
ccccgaggaa aatataatat tcgaagtact cattttcaat caagtatttg ccccgtttc     660
acgtgataca tattttttta ggatttgccc tctctttct ctcctcccag gaaagggagg     720
```

```
ggaaagaatt gtatttttc ccaagtccta aatcatctat atgttaaata tccgtgccga      780
tctgtcttga aggagaaata tatcgcttgt tttgtttttt atagtataca aaaggagtga      840
aaagccaaga ggacgaagtc ttttctttt tcttctgtgg gagaacttaa tgctgcattt       900
atcgttaacc taacacccca acataaagac aaaaggaaga aaaggaggaa ggaaggaaaa      960
ggtgattcgc gaagagagtg atcatgtcag ggcggcccag aaccacctcc tttgcggaga     1020
gctgcaagcc ggtgcagcag ccttcagctt ttggcagcat gaaagttagc agagacaagg     1080
acggcagcaa ggtgacaaca gtggtggcaa ctcctgggca gggtccagac aggccacaag     1140
aagtcagcta tacagacact aaagtgattg gaaatggatc atttggtgtg gtatatcaag     1200
ccaaactttg tgattcagga gaactggtcg ccatcaagaa agtattgcag gacaagagat     1260
ttaagaatcg agagctccag atcatgaaaa agctagatca ctgtaacata gtccgattgc     1320
gttatttctt ctactccagt ggtgagaaga aagatgaggt ctatcttaat ctggtgctgg     1380
actatgttcc ggaaacagta tacagagttg ccagacacta tagtcgagcc aaacagacgc     1440
tccctgtgat ttatgtcaag ttgtatatgt atcagctgtt ccgaagttta gcctatatcc     1500
attcctttgg aatctgccat cgggatatta aaccgcagaa cctcttgttg gatcctgata     1560
ctgctgtatt aaaactctgt gactttggaa gtgcaaagca gctggtccga ggagaaccca     1620
atgtttcgta tatctgttct cggtactata gggcaccaga gttgatcttt ggagccactg     1680
attatacctc tagtatagat gtatggtctg ctggctgtgt gttggctgag ctgttactag     1740
gacaaccaat atttccaggg gatagtggtg tggatcagtt ggtagaaata atcaaggtcc     1800
tgggaactcc aacaagggag caaatcagag aaatgaaccc aaactacaca gaatttaaat     1860
tccctcaaat taaggcacat ccttggacta aggattcgtc aggaacagga catttcacct     1920
caggagtgcg ggtcttccga ccccgaactc caccggaggc aattgcactg tgtagccgtc     1980
tgctggagta tacaccaact gcccgactaa caccactgga agcttgtgca cattcatttt     2040
ttgatgaatt acgggaccca aatgtcaaac taccaaatgg gcgagacaca cctgcactct     2100
tcaacttcac cactcaagaa ctgtcaagta atccacctct ggctaccatc cttattcctc     2160
ctcatgctcg gattcaagca gctgcttcaa cccccacaaa tgccacagca gcgtcagatg     2220
ctaatactgg agaccgtgga cagaccaata atgctgcttc tgcatcagct tccaactcca     2280
cctgaacagt cccgagcagc cagctgcaca ggaaaaacca ccagttactt gagtgtcact     2340
cagcaacact ggtcacgttt ggaaagaata ttaaaaagag aaaaaaatcc tgttcatttt     2400
agtgttcaat tttttatta ttattgttgt tcttatttaa ccttgtaaaa tatctataaa     2460
tacaaaccaa tttcattgta ttctcacttt gagggagatc caggggtgg gagggggttgt     2520 ggggaggggg aaagcggagc actagaacat acaatctctc tcccacgaca atcttttttt     2580
attaaaagtc tgctgttgta tactttaaaa acaggactcc tgcctcatgc ccttccaca      2640 aaagaagaaa acctttttct gtgctgatgg gttttttga actttgtttt cttttaaagt      2700
ctagtgtgag actttggtat agtgcacagc ttgaaattgg ttgggagctt agcaggtata     2760
actcaacggg gacttaaatg tcacttgtaa aattaatcca tatcttcggg tatttataga     2820
cttgcctttg gcatgttggt ggcaggtgtg gcagacaaag aaatgtgtat cattcgtaac     2880
ccagggaggt caataaagtt tggaactcta cagggaagat tcttagtaga tttgttaagg     2940
ttttgttttg ctctcagtta gtgctagtga tgtagaggct tgtacaggag gctgccagag     3000
gggaagcagc aagcaagact caggcacaca tgctctacag gtggctcttt gtttgcctga     3060
ccaaagttct ttgcaaatct tagcacagtt tcaaactagt gacctgggag gagatggaag     3120
```

```
gggtgttgag caggctgagc tagctgctga ggtcaaaggc tgatgagccc agaggaaggg   3180
gacaggtcag ggatacatct caccactgtg aataagtttg tccagatttt tttctaaagt   3240
tacttccctt ggaaagatac acttgagagg acattgtagt taaataatgt gaactgtaac   3300
agtcatctac tggtttattt ttcatatttt ttaattgaaa attgagcttg cagaaatagc   3360
cacattctac acatagttct aattttaaat ccaaatctag aatctgtatt taatttgttt   3420
tttaacctca tgcttttttac atttatttat tgatgcatgt cagatggtag aaatattaaa   3480
aactacacat cagaatgata cagtcactta tacctgctga ctttatagga aagctgatga   3540
tataaatgtg tgtatatatg ttatatatac atatattcaa tactgccttt ttttttgtct   3600
acagtatcaa aattgactgg ttgaagcatg agaagaatgt tcccccaca cccagttaag   3660 agttttttgtg tctgttttct ttgtgtatca gtgaacgatg ttaagaatca gtctctcttt   3720
ttgaagaaaa agcaatattc cttggaaagc aaggagaatt gaaggactat gtttgccgtg   3780
aggaaataga ttttcatgac tagtttgttt tatacttta aggttggcat ctatgtgggc   3840
cttatatact ctaaaatgaa ctttagtcac cttggtgctt atgggccatt acttgaccta   3900
tgaatcttta aggcacaatc agttgtactt tacatttaaa gatcacttga gtgatggccg   3960
cctttccctc ctacccgctc cttccccaca tgccttccaa ggttagctgg taactgtagg   4020
gctgcagagc tgagcccatg gttgtgtgta acttgccctc accctcctca ttgccacctt   4080
aggtcacttt atgggtctcg tcctccagag ggttcggaag tggagtctgt tggcagccct   4140
cctgcaggcc ctagcaccct gtcctgctcc ttaactgtgt gtgtgactct ccaagagagt   4200
tgtcctgcct gctgaagtga accagtaccc agaaagacaa ctgtgagcca tcttggtttt   4260
cactcgctgt ttagctgagg tcttgggcca caaaaggggt ttcacaaacc tctggatata   4320
tcagagttta tgagaaagga aacatgctca gtcaaaccaa atcaaacaaa ttgaattta   4380 tgttttataa agtgcttctg aaagctaaga tttgaaagaa gtctgaaatc aaagtatttg   4440
gcagcataac tccttaaagg tagtggcgtt gatagaccat tttcagacag aatttataaa   4500
gaatctgaaa aggcaggtct gtgatagaga aatggacctg cattcagatc caactgccca   4560
gcaagcgttt ggatgcagac actgctctgg acgtggtata ctccccagag tccataaaaa   4620
tcagtgctta ttttaggaaa caggttgccc cccacaactg gggtaaaaga agagagaaaa   4680
gtcacgcttt tctctcattt cattgtgtgt gcatgtgtgc gtgtgtgtgt gtgtgtgtgt   4740
gtgctgagat gtgtgatttt tctttctcaa ggatcatggt gggatcacag aactcttta   4800 tacaagtgag atccaggtct ctgaatatct ttttgtatat aataataata aaaagctcct   4860
caccaaattc aagcttgtac attatatttt cttctgtgt ttttaaattt aagttttatt   4920
gttttgtatg taaatatgtg gacccaggaa ctgttattaa tgagcaaaaa gttactgttc   4980
agggcagtga ttctgtttaa taatcagaca aaatgtagac gagcttttta aagccatata   5040
gttttaactc tgtacagtag gtaccggcct gtattattgt aacaataact ctagcaatgt   5100
atagtgtatc tatatagttt ggagtgcctt cgcttccatg tgttttttt tttaatttgt   5160 tcttttttaa attttaattg gtttcctta tccatgtctc cctgtccacc ccctttccct   5220
ttgaaataat aactcactca taacagtatc tttgccccctt ccacagttaa gtttcagtga   5280
taccatactc aggagtggga agaggaaatc atattcgtaa tttcatttcg ttgaagccct   5340
gcctttgttt tggttctgaa tgtctttcct cctcggtagc agtgagaccg gtttcatttc   5400
atacttagtc cattcaggga cttagtgtag caccaggag ccctagagct ggaggatatc   5460
```

```
gaatagatta aatttgctc gtctcttcca caagccctaa ccatgggtct taaaaacagc    5520
agattctggg agccttccat gctctctctc tctcctcttt tatctacttc cctcccaaat    5580
gagagagtga cagagaattg ttttttttata aatcgaagtt tcttaatagt atcaggtttt    5640
gatacgtcag tggtctaaaa tgctatagtg caattactag cagttactgc acggagtgcc    5700
accgtgccaa tagaggactg ttgttttaac aagggaactc ttagcccatt tcctccctcc    5760
cgccatctct accctgctc aatgaaatat cattttaatt tcttttaaaa aaaatcagtt    5820
taattcttac tgtgtgccca acacgaaggc ctttttgaa agaaaaatag aatgttttgc    5880
ctcaaagtag tccatataaa atgtcttgaa tagaagaaaa aactaccaaa ccaaaggtta    5940
ctatttttga aacatcgtgt gttcattcca gcaaggcaga agactgcacc ttctttccag    6000
tgacatgctg tgtcattttt tttaagtcct cttaatttt agacacattt ttggtttatg    6060
ttttaacaat gtatgcctaa ccagtcatct tgtctgcacc aatgcaaagg tttctgagag    6120
gagtattctc tatccctgtg gatatgaaga cactggcatt tcatctattt ttcccttttcc    6180
ttttttaaagg atttaacttt ggaatcttcc aaaggaagtt tggccaatgc cagatcccca    6240
ggaatttggg gggttttctt tcttttcaac tgaaattgta tctgattcct actgttcatg    6300
ttagtgatca tctaatcaca gagccaaaca ctttctccc ctgtgtggaa aagtaggtat    6360
gctttacaat aaaatctgtc ttttctggta gaaacctgag ccactgaaaa taaaagagac    6420
aactagaagc acagtagagt cccagactga gatctacctt tgagaggctt tgaaagtaat    6480
ccctggggtt tggattattt tcacaagggt tatgccgttt tattcaagtt tgttgctccg    6540
ttttgcacct ctgcaataaa agcaaaatga caaccagtac ataagggggtt agcttgacaa    6600
agtagacttc cttgtgttaa ttttttaagtt ttttttttcct taactatatc tgtctacagg    6660
cagatacaga tagttgtatg aaatctgct tgcctgtaaa atttgcattt ataaatgtgt    6720
tgccgatgga tcacttgggc ctgtacacat accaattagc gtgaccactt ccatcttaaa    6780
aacaaaccta aaaaacaaaa tttattatat atatatat atatatataa aggactgtgg    6840
gttgtataca aactattgca aacacttgtg caaatctgtc ttgatataaa ggaaaagcaa    6900
aatctgtata acattattac tacttgaatg ccctctgtgac tgatttttt ttcattttaa    6960
atataaactt ttttgtgaaa agtatgctca atgtttttt tcccttttccc cattcccttg    7020
taaatacatt ttgttctatg tgacttggtt tggaaatagt taactggtac tgtaatttgc    7080
attaaataaa aagtaggtta gcctggaaat gaaattaaaa aaaaaaaaaa aaaa         7134
```

<210> SEQ ID NO 20
<211> LENGTH: 403
<212> TYPE: PRT
<213> ORGANISM: Homo sapiens

<400> SEQUENCE: 20

```
Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
        35                  40                  45

Asn Ile Asp Asp Val Val Arg Phe Leu Asp Ser Lys His Lys Asn His
    50                  55                  60

Tyr Lys Ile Tyr Asn Leu Cys Ala Glu Arg His Tyr Asp Thr Ala Lys
65                  70                  75                  80
```

```
                Phe Asn Cys Arg Val Ala Gln Tyr Pro Phe Glu Asp His Asn Pro Pro
                                85                  90                  95

Gln Leu Glu Leu Ile Lys Pro Phe Cys Glu Asp Leu Asp Gln Trp Leu
                            100                 105                 110

Ser Glu Asp Asp Asn His Val Ala Ala Ile His Cys Lys Ala Gly Lys
                        115                 120                 125

Gly Arg Thr Gly Val Met Ile Cys Ala Tyr Leu Leu His Arg Gly Lys
                    130                 135                 140

Phe Leu Lys Ala Gln Glu Ala Leu Asp Phe Tyr Gly Glu Val Arg Thr
                145                 150                 155                 160

Arg Asp Lys Lys Gly Val Thr Ile Pro Ser Gln Arg Arg Tyr Val Tyr
                                165                 170                 175

Tyr Tyr Ser Tyr Leu Leu Lys Asn His Leu Asp Tyr Arg Pro Val Ala
                            180                 185                 190

Leu Leu Phe His Lys Met Met Phe Glu Thr Ile Pro Met Phe Ser Gly
                        195                 200                 205

Gly Thr Cys Asn Pro Gln Phe Val Val Cys Gln Leu Lys Val Lys Ile
                    210                 215                 220

Tyr Ser Ser Asn Ser Gly Pro Thr Arg Arg Glu Asp Lys Phe Met Tyr
                225                 230                 235                 240

Phe Glu Phe Pro Gln Pro Leu Pro Val Cys Gly Asp Ile Lys Val Glu
                                245                 250                 255

Phe Phe His Lys Gln Asn Lys Met Leu Lys Lys Asp Lys Met Phe His
                            260                 265                 270

Phe Trp Val Asn Thr Phe Phe Ile Pro Gly Pro Glu Glu Thr Ser Glu
                        275                 280                 285

Lys Val Glu Asn Gly Ser Leu Cys Asp Gln Glu Ile Asp Ser Ile Cys
                    290                 295                 300

Ser Ile Glu Arg Ala Asp Asn Asp Lys Glu Tyr Leu Val Leu Thr Leu
                305                 310                 315                 320

Thr Lys Asn Asp Leu Asp Lys Ala Asn Lys Asp Lys Ala Asn Arg Tyr
                                325                 330                 335

Phe Ser Pro Asn Phe Lys Val Lys Leu Tyr Phe Thr Lys Thr Val Glu
                            340                 345                 350

Glu Pro Ser Asn Pro Glu Ala Ser Ser Ser Thr Ser Val Thr Pro Asp
                        355                 360                 365

Val Ser Asp Asn Glu Pro Asp His Tyr Arg Tyr Ser Asp Thr Thr Asp
                    370                 375                 380

Ser Asp Pro Glu Asn Glu Pro Phe Asp Glu Asp Gln His Thr Gln Ile
                385                 390                 395                 400

Thr Lys Val

<210> SEQ ID NO 21
<211> LENGTH: 5572
<212> TYPE: DNA
<213> ORGANISM: Homo sapiens

<400> SEQUENCE: 21
cctcccctcg cccggcgcgg tcccgtccgc ctctcgctcg cctcccgcct ccccctcggtc    60 ttccgaggcg cccgggctcc cggcgcggcg gcggagggggg cgggcaggcc ggcgggcggt   120
gatgtggcgg gactctttat gcgctgcggc aggatacgcg ctcggcgctg gacgcgact    180 gcgctcagtt ctctcctctc ggaagctgca gccatgatgg aagtttgaga gttgagccgc   240
tgtgaggcga ggccgggctc aggcgaggga gatgagagac ggcggcggcc gcggcccgga   300
```

```
gccccctctca gcgcctgtga gcagccgcgg gggcagcgcc ctcggggagc cggccggcct    360
gcggcggcgg cagcggcggc gtttctcgcc tcctcttcgt cttttctaac cgtgcagcct    420
cttcctcggc ttctcctgaa agggaaggtg gaagccgtgg gctcgggcgg gagccggctg    480
aggcgcggcg gcggcggcgg cacctcccgc tcctggagcg gggggggagaa gcggcggcgg    540 cggcggccgc ggcggctgca gctccaggga ggggtctga gtcgcctgtc accatttcca    600
gggctgggaa cgccggagag ttggtctctc cccttctact gcctccaaca cggcggcggc    660
ggcggcggca catccaggga cccgggccgg ttttaaacct cccgtccgcc gccgccgcac    720
cccccgtggc ccgggctccg gaggccgccg gcggaggcag ccgttcggag gattattcgt    780
cttctcccca ttccgctgcc gccgctgcca ggcctctggc tgctgaggag aagcaggccc    840
agtcgctgca accatccagc agccgccgca gcagccatta cccggctgcg gtccagagcc    900
aagcggcggc agagcgaggg gcatcagcta ccgccaagtc cagagccatt ccatcctgc    960 agaagaagcc ccgccaccag cagcttctgc catctctctc ctccttttc ttcagccaca    1020 ggctcccaga catgacagcc atcatcaaag agatcgttag cagaaacaaa aggagatatc    1080
aagaggatgg attcgactta gacttgacct atatttatcc aaacattatt gctatgggat    1140 tcctgcaga aagacttgaa ggcgtataca ggaacaatat tgatgatgta gtaaggtttt    1200
tggattcaaa gcataaaaac cattacaaga tatacaatct tgtgctgaa agacattatg    1260 acaccgccaa atttaattgc agagttgcac aatatccttt tgaagaccat aacccaccac    1320
agctagaact tatcaaaccc ttttgtgaag atcttgacca atggctaagt gaagatgaca    1380
atcatgttgc agcaattcac tgtaaagctg gaaagggacg aactggtgta atgatatgtg    1440
catatttatt acatcggggc aaattttta aggcacaaga ggccctagat ttctatgggg    1500
aagtaaggac cagagacaaa aagggagtaa ctattcccag tcagaggcgc tatgtgtatt    1560
attatagcta cctgttaaag aatcatctgg attatagacc agtggcactg ttgtttcaca    1620
agatgatgtt tgaaactatt ccaatgttca gtggcggaac ttgcaatcct cagtttgtgg    1680
tctgccagct aaaggtgaag atatattcct ccaattcagg acccacacga cgggaagaca    1740
agttcatgta ctttgagttc cctcagccgt tacctgtgtg tggtgatatc aaagtagagt    1800
tcttccacaa acagaacaag atgctaaaaa aggacaaaat gttctcacttt tgggtaaata    1860 cattcttcat accaggacca gaggaaaacct cagaaaaagt agaaaatgga agtctatgtg    1920
atcaagaaat cgatagcatt tgcagtatag agcgtgcaga taatgacaag gaatatctag    1980
tacttacttt aacaaaaat gatcttgaca aagcaaataa agcaaagcc aaccgatact    2040 tttctccaaa ttttaaggtg aagctgtact tcacaaaaac agtagaggag ccgtcaaatc    2100
cagaggctag cagttcaact tctgtaacac cagatgttag tgacaatgaa cctgatcatt    2160
atagatattc tgacaccact gactctgatc cagagaatga acctttttgat gaagatcagc    2220 atacacaaat tacaaaagtc tgaattttt tttatcaaga gggataaaac accatgaaaa    2280
taaacttgaa taaactgaaa atggaccttt ttttttttaa tggcaatagg acattgtgtc    2340
agattaccag ttataggaac aattctcttt tcctgaccaa tcttgttttta ccctatacat    2400 ccacagggtt ttgacacttg ttgtccagtt gaaaaaggt tgtgtagctg tgtcatgtat    2460 atacctttt gtgtcaaaag gacatttaaa attcaattag gattaataaa gatggcactt    2520
tcccgtttta ttccagtttt ataaaaagtg gagacagact gatgtgtata cgtaggaatt    2580
ttttcctttt gtgttctgtc accaactgaa gtggctaaag agctttgtga tatactggtt    2640
```

```
cacatcctac cccttttgcac ttgtggcaac agataagttt gcagttggct aagagaggtt    2700
tccgaagggt tttgctacat tctaatgcat gtattcgggt taggggaatg gagggaatgc    2760
tcagaaagga aataatttta tgctggactc tggaccatat accatctcca gctatttaca    2820
cacacctttc tttagcatgc tacagttatt aatctggaca ttcgaggaat tggccgctgt    2880
cactgcttgt tgtttgcgca ttttttttta aagcatattg gtgctagaaa aggcagctaa    2940
aggaagtgaa tctgtattgg ggtacaggaa tgaaccttct gcaacatctt aagatccaca    3000
aatgaaggga tataaaaata atgtcatagg taagaaacac agcaacaatg acttaaccat    3060
ataaatgtgg aggctatcaa caaagaatgg gcttgaaaca ttataaaaat tgacaatgat    3120
ttattaaata tgttttctca attgtaacga cttctccatc tcctgtgtaa tcaaggccag    3180
tgctaaaatt cagatgctgt tagtacctac atcagtcaac aacttacact tatttttacta   3240 gttttcaatc ataatacctg ctgtggatgc ttcatgtgct gcctgcaagc ttcttttttc    3300
tcattaaata taaatatttt tgtaatgctg cacagaaatt ttcaatttga gattctacag    3360
taagcgtttt ttttctttga agatttatga tgcacttatt caatagctgt cagccgttcc    3420
acccttttga ccttacacat tctattacaa tgaattttgc agtttttgcac attttttaaaa   3480 tgtcattaac tgttagggaa ttttacttga atactgaata catataatgt ttatattaaa    3540
aaggacattt gtgttaaaaa ggaaattaga gttgcagtaa actttcaatg ctgcacacaa    3600
aaaaaagaca tttgattttt cagtagaaat tgtcctacat gtgctttatt gatttgctat    3660
tgaaagaata gggttttttt tttttttttt tttttttttt ttaaatgtgc agtgttgaat    3720
catttcttca tagtgctccc ccgagttggg actagggctt caatttcact tcttaaaaaa   3780
aatcatcata tatttgatat gcccagactg catacgattt taagcggagt acaactacta    3840
ttgtaaagct aatgtgaaga tattattaaa aaggtttttt tttccagaaa tttggtgtct    3900
tcaaattata ccttcacctt gacatttgaa tatccagcca ttttgtttct taatggtata    3960
aaattccatt ttcaataact tattggtgct gaaattgttc actagctgtg gtctgaccta    4020
gttaatttac aaatacagat tgaataggac ctactagagc agcatttata gagtttgatg    4080
gcaaatagat taggcagaac ttcatctaaa atattcttag taaataatgt tgacacgttt    4140 tccataccttt gtcagtttca ttcaacaatt tttaaatttt taacaaagct cttaggattt    4200
acacatttat atttaaacat tgatatatag agtattgatt gattgctcat aagttaaatt    4260
ggtaaagtta gagacaacta ttctaacacc tcaccattga aatttatatg ccaccttgtc    4320
tttcataaaa gctgaaaatt gttacctaaa atgaaaatca acttcatgtt ttgaagatag    4380
ttataaatat tgttctttgt tacaatttcg ggcaccgcat attaaaacgt aactttattg    4440
ttccaatatg taacatggag ggccaggtca taaataatga cattataatg ggcttttgca    4500
ctgttattat ttttcctttg gaatgtgaag gtctgaatga gggttttgat tttgaatgtt    4560
tcaatgtttt tgagaagcct tgcttacatt ttatggtgta gtcattggaa atggaaaaat    4620
ggcattatat atattatata tataaatata tattatacat actctcctta ctttatttca    4680
gttaccatcc ccatagaatt tgacaagaat tgctatgact gaaaggtttt cgagtcctaa    4740
ttaaaacttt atttatggca gtattcataa ttagcctgaa atgcattctg taggtaatct    4800
ctgagtttct ggaatatttt cttagacttt ttggatgtgc agcagcttac atgtctgaag    4860
ttacttgaag gcatcacttt taagaaagct tacagtttggg ccctgtacca tcccaagtcc   4920
tttgtagctc ctcttgaaca tgtttgccat acttttaaaa gggtagttga ataaatagca    4980
tcaccattct ttgctgtggc acaggttata aacttaagtg gagtttaccg gcagcatcaa    5040
```

```
atgtttcagc tttaaaaaat aaaagtaggg tacaagttta atgtttagtt ctagaaattt      5100
tgtgcaatat gttcataacg atggctgtgg ttgccacaaa gtgcctcgtt taccttaaa       5160 tactgttaat gtgtcatgca tgcagatgga aggggtggaa ctgtgcacta agtgggggc       5220 tttaactgta gtatttggca gagttgcctt ctacctgcca gttcaaaagt tcaacctgtt      5280
ttcatataga atatatatac taaaaaattt cagtctgtta aacagcctta ctctgattca      5340
gcctcttcag atactcttgt gctgtgcagc agtggctctg tgtgtaaatg ctatgcactg      5400
aggatacaca aaataccaa tatgatgtgt acaggataat gcctcatccc aatcagatgt       5460
ccatttgtta ttgtgtttgt taacaaccct ttatctctta gtgttataaa ctccacttaa      5520
aactgattaa agtctcattc ttgtcaaaaa aaaaaaaaaa aaaaaaaaa aa               5572

<210> SEQ ID NO 22
<211> LENGTH: 152
<212> TYPE: PRT
<213> ORGANISM: Homo sapiens

<400> SEQUENCE: 22

Met Ala Gly Leu Pro Arg Arg Ile Ile Lys Glu Thr Gln Arg Leu Leu
1               5                   10                  15

Ala Glu Pro Val Pro Gly Ile Lys Ala Glu Pro Asp Glu Ser Asn Ala
            20                  25                  30

Arg Tyr Phe His Val Val Ile Ala Gly Pro Gln Asp Ser Pro Phe Glu
        35                  40                  45

Gly Gly Thr Phe Lys Leu Glu Leu Phe Leu Pro Glu Glu Tyr Pro Met
    50                  55                  60

Ala Ala Pro Lys Val Arg Phe Met Thr Lys Ile Tyr His Pro Asn Val
65                  70                  75                  80

Asp Lys Leu Gly Arg Ile Cys Leu Asp Ile Leu Lys Asp Lys Trp Ser
                85                  90                  95

Pro Ala Leu Gln Ile Arg Thr Val Leu Leu Ser Ile Gln Ala Leu Leu
            100                 105                 110

Ser Ala Pro Asn Pro Asp Asp Pro Leu Ala Asn Asp Val Ala Glu Gln
        115                 120                 125

Trp Lys Thr Asn Glu Ala Gln Ala Ile Glu Thr Ala Arg Ala Trp Thr
    130                 135                 140

Arg Leu Tyr Ala Met Asn Asn Ile
145                 150

<210> SEQ ID NO 23
<211> LENGTH: 1250
<212> TYPE: DNA
<213> ORGANISM: Homo sapiens

<400> SEQUENCE: 23
gtcccccgga agtggagccc gggacttcca ctcgtgcgtg aggcgagagg agccggagac      60
gagaccagag gccgaactcg ggttctgaca agatggccgg gctgccccgc aggatcatca      120
aggaaaccca gcgtttgctg gcagaaccag ttcctggcat caaagccgaa ccagatgaga      180
gcaacgcccg ttattttcat gtggtcattg ctggccctca ggattccccc tttgagggag      240
ggacttttaa acttgaacta ttccttccag aagaataccc aatggcagcc cctaaagtac      300
gtttcatgac caaatttat catcctaatg tagacaagtt gggaagaata tgtttagata      360
ttttgaaaga taagtggtcc ccagcactgc agatccgcac agttctgcta tcgatccagg      420
```

```
ccttgttaag tgctcccaat ccagatgatc cattagcaaa tgatgtagcg gagcagtgga        480
agaccaacga agcccaagcc atagaaacag ctagagcatg gactaggcta tatgccatga        540
ataatattta aattgatacg atcatcaagt gtgcatcact tctcctgttc tgccaagact        600
tcctcctctt tgtttgcatt taatggacac agtcttagaa acattacaga ataaaaaagc        660
ccagacatct tcagtccttt ggtgattaaa tgcacattag caaatctatg tcttgtcctg        720
attcactgtc ataaagcatg agcagaggct agaagtatca tctggattgt tgtgaaacgt        780
ttaaaagcag tggcccctcc ctgcttttat tcatttcccc catcctggtt taagtataaa        840
gcactgtgaa tgaaggtagt tgtcaggtta gctgcagggg tgtgggtgtt tttatttat         900 tttatttat  tttatttttg aggggggagg tagtttaatt ttatgggctc ctttcccccct      960 tttttggtga tctaattgca ttggttaaaa gcagctaacc aggtctttag aatatgctct      1020
agccaagtct aactttattt agacgctgta gatggacaag cttgattgtt ggaaccaaaa      1080
tgggaacatt aaacaaacat cacagccctc actaataaca ttgctgtcaa gtgtagattc      1140 ccccttcaa aaaaagcttg tgaccatttt gtatggcttg tctggaaact tctgtaaatc       1200
ttatgtttta gtaaaatatt ttttgttatt ctaaaaaaaa aaaaaaaaa                  1250
```

METHOD TO ASSESS PATTERNS OF MOLECULAR EXPRESSION

SEQUENCE LISTING

The instant application contains a Sequence Listing which has been submitted in ASCII format via EFS-Web and is hereby incorporated by reference in its entirety. Said ASCII copy, created on Jun. 12, 2013, is named PATH-4US_SL.txt and is 110,165 bytes in size.

FIELD OF THE INVENTION

The invention is directed to a method to establish a biologically significant association of gene expression levels among two or more genes, the method comprising assaying a sample for expression levels of two or more genes and identifying statistically-significant associations using a correlation coefficient in the range of about 0.6 to about 1.0, wherein a correlation coefficient in that range signifies a biologically significant correlation.

SUMMARY OF THE INVENTION

The inventor has discovered that through the application of specific techniques it was possible to correlate levels of molecular expression of two or more genes with correlation coefficients (r values) greater than 0.6. These r values indicate correlations in gene expression that are, with very high probability, biologically significant.

Previously, in the industry, r values in that range have not been observed for molecular expression levels. Using a technology that allowed for greater sensitivity facilitated the inventor's ability to increase the dynamic range to such a scale. Techniques that produce precise quantitative data and have a significant dynamic range allows for the generation of these high r values. Although technology to produce such data existed prior to the invention, the utility of the technology was not actually realized until one used it to analyze highly correlated molecular associations. These correlations were entirely unexpected.

Accordingly, the invention is directed to a method to establish a biologically significant association of gene expression levels among two or more genes, the method comprising assaying a sample for expression levels of two or more genes and identifying statistically-significant associations using a correlation coefficient in the range of about 0.6 to about 1.0, wherein a correlation coefficient in that range signifies a biologically significant correlation.

In one embodiment protein expression is assayed. Protein expression that is assayed can be intracellular, extracellular (i.e. surface), or both.

In another embodiment gene expression is assayed via expression of RNA. RNA can be any RNA, including, messenger RNA and smaller RNA molecules, such as microRNAs.

In a further embodiment, post-translational modifications may be assayed, including phosphorylation, acetylation, nitrosylation, ubiquitination, sulfation, glycosylation, myristoylation, palmistoylation, isoprenylation, farnesylation, geranylgeranylation, alkylation, amidation, acylation, oxidation, SUMOylation, Pupylation, Neddylation, biotinylation, pegylation, succinylation, selenoylation, citrullination, deamidation, ADP-ribosylation, iodination, hydroxylation, gamma-carboxylation, carbamylation, S-nitrosylation, S-glutathionylation, and malonylation, as well as any other post-translational modification.

In one embodiment gene expression is assessed by flow cytometry. Another embodiment involves the detection of molecular expression levels in enriched cells by western blotting. Another embodiment involves the detection of molecular expression levels via reverse phase protein arrays involving purified cells. Kornblau S et al. *Blood* 2009: 113:154-164. Immunoassays on lysates of purified or enriched cells is another embodiment. Gene expression can also be assessed by measuring mRNA with enough precision to obtain correlations with r>0.6. mRNA determinations can be obtained with real-time PCR.

In another embodiment gene expression is assessed in single cells.

In another embodiment gene expression assessment is assessed by EAS.

In another embodiment gene expression is assessed in at least 50 cells.

In a specific embodiment the correlation coefficient is in the range of about 0.6-0.7.

In a specific embodiment the correlation coefficient is in the range of about 0.7-0.8.

In a specific embodiment the correlation coefficient is in the range of about 0.8-0.9.

In a specific embodiment the correlation coefficient is in the range of about 0.9-1.0.

BRIEF DESCRIPTION OF THE DRAWINGS

FIG. 8 shows the amino acid sequence of Human Atg7 (SEQ ID NO: 1) from the site disclosed in the Definitions.

FIG. 9 shows the nucleotide sequence of Human ATG7 (SEQ ID NO: 2) from the site disclosed in the Definitions. FIG. 9A discloses nucleotides 1-3,780 of SEQ. ID NO: 2. FIG. 9B discloses nucleotides 3,781-5,059 of SEQ ID NO: 2.

FIG. 10 shows the amino acid sequence of Human Bmi-1 (SEQ ID NO: 3) from the site disclosed in the Definitions.

FIG. 11 shows the amino acid and nucleotide sequence of Human C-Myc (SEQ ID NOS: 4 and 5, respectively, in order of appearance) from the site disclosed in the Definitions.

FIG. 12 shows the amino acid sequence of Human E47 (SEQ ID NO: 6) from the site disclosed in the Definitions.

FIG. 13 shows the nucleotide sequence of Human E47 (SEQ ID NO: 7) from the site disclosed in the Definitions. FIG. 13A discloses nucleotides 1-2,700 of SEQ ID NO. 7. FIG. 13B discloses nucleotides 2,701-4,078 of SEQ ID NO: 7.

FIG. 14 shows the amino acid sequence of Human GATA-2 (SEQ ID NO: 8) from the site disclosed in the Definitions.

FIG. 15 shows the amino acid sequence of Human Hox B4 (SEQ ID NO: 9) from the site disclosed in the Definitions.

FIG. 16 shows the amino acid and nucleotide sequence of Human Mcl-1 (SEQ ID NO: 10 and SEQ ID NO: 11, respectively) from the site disclosed in the Definitions. FIG. 16A discloses the amino acid sequence (SEQ ID NO: 10) and nucleotides 1-1,020 of SEQ ID NO: 11, FIG. 16B discloses nucleotides 1,021-3,540 of SEQ ID NO: 11. FIG. 16C discloses nucleotides 3,541-5,880 of SEQ ID NO: 11. FIG. 16D discloses nucleotides 5,881-8,400 of SEQ ID NO: 11. FIG. 16E discloses nucleotides 8,401-10,740 of SEQ ID NO: 11. FIG. 16F discloses nucleotides 10,741-12,192 of SEQ ID NO: 11.

FIG. 17 shows the amino acid and nucleotide sequence of Human Musashi 2 (SEQ ID NOS: 12 and 13, respectively, in order of appearance) from the site disclosed in the Definitions.

FIG. 18 shows the amino acid sequence of Human AKT1 (SEQ ID NO: 14) from the site disclosed in the Definitions.

FIG. 19 shows the nucleotide sequence of Human AKT1 (SEQ ID NO: 151 from the site disclosed in the Definitions.

FIG. 20 shows the amino acid sequence of Human AKT2 (SEQ ID NO: 16) from the site disclosed in the Definitions.

FIG. 21 shows the nucleotide sequence of Human AKT2 (SEQ ID NO: In from the site disclosed in the Definitions. FIG. 21A discloses nucleotides 1-2,880 of SEQ ID NO: 17. FIG. 21B discloses nucleotides 2,881-5,280 of SEQ ID NO: 17.

FIG. 22 shows the amino acid sequence of Human GSK-36 (SEQ ID NO: 18) from the site disclosed in the Definitions.

FIG. 23 shows the nucleotide sequence of Human GSK-3β (SEQ ID NO from the site disclosed in the Definitions. FIG. 23A discloses nucleotides 1-3,060 of SEQ ID NO: 19. FIG. 23B discloses nucleotides 3,061-5,400 of SEQ ID NO: 19. FIG. 23C discloses nucleotides 5,401-7,134.

FIG. 24 shows the amino acid sequence of Human PTEN (SEQ ID NO: 20) from the site disclosed in the Definitions.

FIG. 25 shows the nucleotide sequence of Human PTEN (SEQ ID NO: 21) from the site disclosed in the Definitions. FIG. 25A discloses nucleotides 1-720 of SEQ ID NO: 21. FIG. 25B discloses nucleotides 721-2,760 of SEQ ID NO: 21. FIG. 25C discloses nucleotides 2,761-5,572 of SEQ ID NO: 21.

FIG. 26 shows the amino acid and nucleotide sequence of Human UBC 13 (SEQ ID NOS:22 and 23, respectively, in order of appearance) from the site disclosed in the Definitions.

DETAILED DESCRIPTION OF THE INVENTION

Definitions

Figure 1:
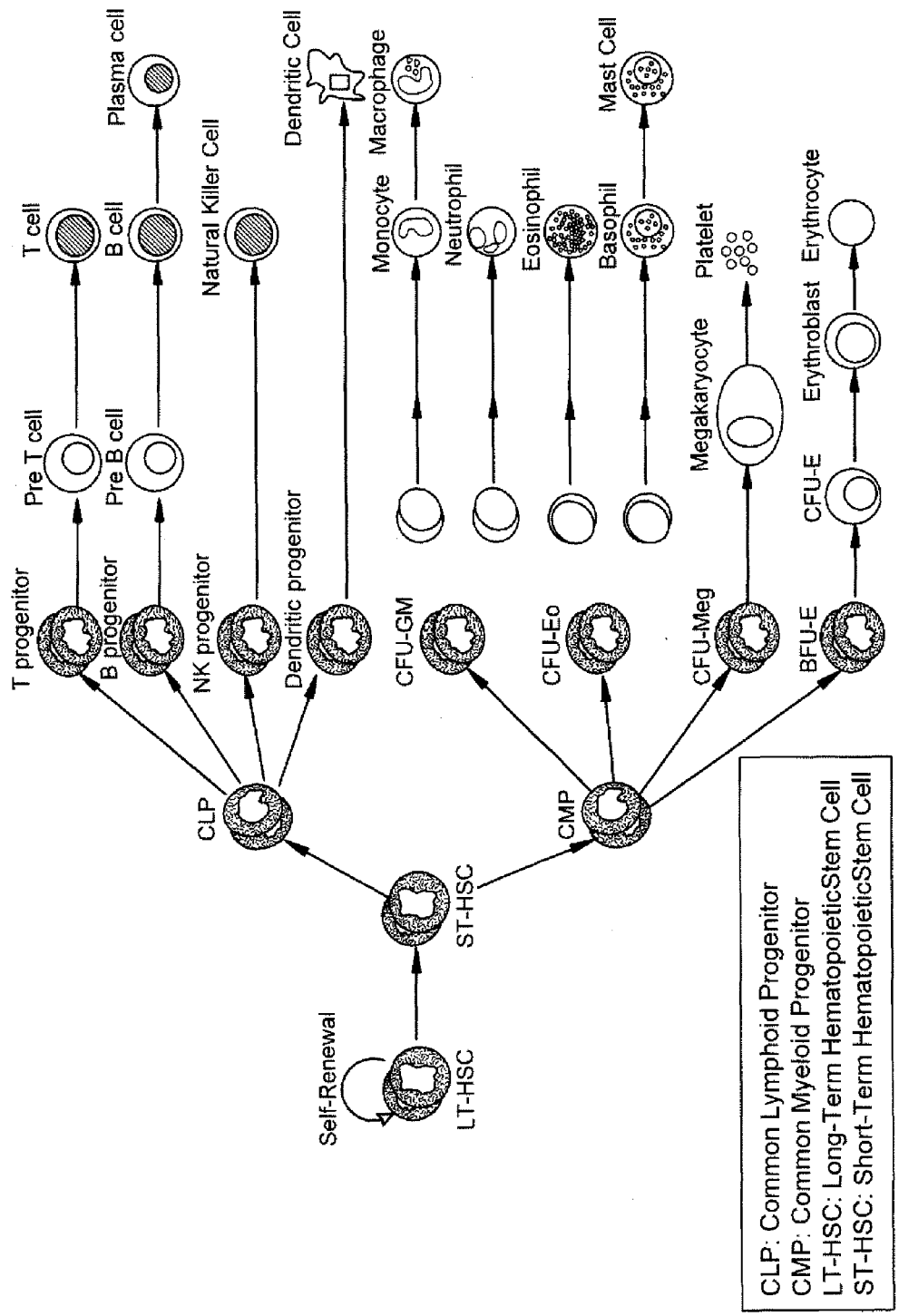
FIG. 1 is a schematic of hematopoietic differentiation.

"A" or "an" means herein one or more than one; at least one. Where the plural form is used herein, it generally includes the singular.

The term "Atg7" is understood to refer to Autophagy-related protein 7, a protein essential in the cellular function of autophagy, encoded by a gene having, in humans, the sequence shown in NCBI Reference Sequence: NM 006395.2. The sequence can be found at the following site: http://www.ncbi.nlm.nih.gov/nuccore/NM_006395.2, incorporated by reference for the sequence. There are two other variants of the gene. The one referenced is the longest variant. This gene is also known, like most other genes, to contain polymorphisms that still allow the gene to maintain the function. The gene also includes, for non-human uses, such as veterinary uses, orthologs from other mammals. These include companion animals, farm animals and sport animals, for example, felines, canines, bovines, equines, porcines, ovines, etc.

The term "Bmi-1" refers to "a component of the Polycomb group multiprotein PRC-1 like complex, a complex class required to maintain the transcriptionally repressive state of many genes throughout development". Bmi-1 is required for the maintenance of adult self-renewing hematopoietic stem cells. Nature 2003 May 15 423:302-305 Park et al. The sequence can be found at the following site: http://www.uniprot.org/uniprot/P35226, incorporated by reference.

The term "bootstrapping" in statistics refers to the method of generating new samples of the same size from an original sample by selecting results with replacement of each result selected. This procedure is repeated many times to generate a histogram of means for each bootstrapped sample, and this histogram provides an estimate of the distribution appearance. Bootstrapping is useful in situations with small sample size or unusual distribution shapes.

A "cell bank" is industry nomenclature for cells that have been grown and stored for future use. Cells may be stored in aliquots. They can be used directly out of storage or may be expanded after storage. This is a convenience so that there are "off the shelf" cells available for administration. The cells may already be stored in a pharmaceutically-acceptable excipient so they may be directly administered or they may be mixed with an appropriate excipient when they are released from storage. Cells may be frozen or otherwise stored in a form to preserve viability. In one embodiment of the invention, cell banks are created in which the cells have been selected for enhanced potency to achieve the effects described in this application. Following release from storage, and prior to administration to the subject, it may be preferable to again assay the cells for potency. This can be done using any of the assays, direct or indirect, described in this application or otherwise known in the art. Then cells having the desired potency can then be administered to the subject for treatment. Banks can be made using cells derived from the individual to be treated (from their pre-natal tissues such as placenta, umbilical cord blood, or umbilical cord matrix or expanded from the individual at any time after birth). Or banks can contain cells for allogeneic uses.

The term "cluster analysis," as used herein, refers to the process of grouping results into clusters with the members a cluster have greater similarity to each other than to members of other clusters.

The term "cMyc" is understood to refer to a mammalian homolog of a viral oncogene, v-Myc. It is a basic helix-loop-helix transcription factor that functions to activate a large number of genes. It is encoded by a gene having, in humans, the sequence shown in NCBI Reference Sequence: NM_002467.4, incorporated by reference for the sequence. However, this gene is also known, like most other genes, to contain polymorphisms that still allow the gene to maintain the function. The gene also includes, for non-human uses, such as veterinary uses, orthologs from other mammals. These include companion animals, farm animals and sport animals, for example, felines, canines, bovines, equines, porcines, ovines, etc.

"Co-administer" means to administer in conjunction with one another, together, coordinately, including simultaneous or sequential administration of two or more agents.

"Comprised of" is a synonym of "comprising".

"Comprising" means, without other limitation, including the referent, necessarily, without any qualification or exclusion on what else may be included. For example, "a composition comprising x and y" encompasses any composition that contains x and y, no matter what other components may be present in the composition. Likewise, "a method comprising the step of x" encompasses any method in which x is carried out, whether x is the only step in the method or it is only one of the steps, no matter how many other steps there may be and no matter how simple or complex x is in comparison to them. "Comprised of" and similar phrases using words of the root "comprise" are used herein as synonyms of "comprising" and have the same meaning.

"Correlation" means the Pearson product-moment correlation coefficient or Pearson's r is a measure of the linear interdependence of two variables. This statistical parameter is used to assess whether the expression levels of two molecules are related. "Correlation matrix" is the matrix of correlations of all variables with all other variables. The diagonal of this matrix will be 1.0 at every point since each parameter is totally correlated with itself.

"Correlations" examines the pairwise relationships for variables in the dataset. For 2 variables or, in the present case, expression levels, there is a single correlation. For three variables there are three correlations. For four variables there are six correlations. For five variables there are ten correlations. The inventor used the Pearson correlation coefficient which is calculated either with SPSS or by Excel which also includes statistical analysis.

"Decrease" or "reduce" means to prevent entirely as well as to lower.

The term "E47" is understood to refer to a basic helix-loop-helix transcription factor that has been shown to regulate hematopoietic-reconstituting cell maintenance and proliferation. It is encoded by a gene having, in humans, the sequence shown in NCBI Reference Sequence: NM_001136139.2, incorporated by reference for the sequence. However, this gene is also known, like most other genes, to contain polymorphisms that still allow the gene to maintain the function. The gene also includes, for non-human uses, such as veterinary uses, orthologs from other mammals. These include companion animals, farm animals and sport animals, for example, felines, canines, bovines, equines, porcines, ovines, etc.

"EAS" is trademarked by the inventor. The generic description is enzymatic amplification staining. It is a procedure to amplify the signal in flow cytometric analysis. Patents describing the procedure are listed below.

"Effective amount" generally means an amount which provides the desired effect. For example, an effective amount is an amount sufficient to effectuate a beneficial or desired clinical result. The effective amounts can be provided all at once in a single administration or in fractional amounts that provide the effective amount in several administrations. The precise determination of what would be considered an effective amount may be based on factors individual to each subject, including their size, age, injury, and/or disease or injury being treated, and amount of time since the injury occurred or the disease began. One skilled in the art will be able to determine the effective amount for a given subject based on these considerations which are routine in the art. As used herein, "effective dose" means the same as "effective amount."

"Effective route" generally means a route which provides for delivery of an agent to a desired compartment, system, or location. For example, an effective route is one through which an agent can be administered to provide at the desired site of action an amount of the agent sufficient to effectuate a beneficial or desired clinical result.

The term "factor analysis" and "principal component analysis" means a type of assessment used to find higher levels of structure in a data set beyond just the relationships between pairs of variables. The technique uses linear algebraic methods to detect sets of variables that are related to each other. This analysis is performed by a computer program.

The term "GATA2" refers to a member of the Zinc finger transcription factor family; it plays an essential role in regulating transcription of genes involved in the development and proliferation of hematopoietic cell lineages. The sequence can be found at the following site: http://www.ncbi.nlm.nih.gov/gene/2624, incorporated by reference. The site for a reference is: http://www.ncbi.nlm.nih.gov/nuccore/NG_029334.1?report=genbank&from=5001&to=18766, incorporated by reference.

The term "HoxB4" is understood to refer to a transcription factor encoded by a gene having, in humans, the sequence shown in, for example, Acampora et al., *Nucl. Acids. Res.* 17: 10385-10402 (1989). Also see NCBI Reference, Sequence: NM_204015.4, incorporated by reference for the sequence. This gene is also known, like most other genes, to contain polymorphisms that still allow the gene to maintain the capacity for HoxB4 function. The gene also includes, for non-human uses, such as veterinary uses, HoxB4 orthologs from other mammals. These include companion animals, farm animals and sport animals, for example, felines, canines, bovines, equines, porcines, ovines, etc. See also http://www.uniprot.org/uniprot/P17483, incorporated by reference.

Use of the term "includes" is not intended to be limiting.

"Increase" or "increasing" means to induce entirely, where there was no pre-existing effect, as well as to increase the degree.

The term "isolated" refers to a cell or cells which are not associated with one or more cells or one or more cellular components that are associated with the cell or cells in vivo. An "enriched population" means a relative increase in numbers of a desired cell relative to one or more other cell types in vivo or in primary culture.

The term "isolated" refers to a cell or cells which are not associated with one or more cells or one or more cellular components that are associated with the cell or cells in vivo. An "enriched population" means a relative increase in numbers of a desired cell relative to one or more other cell types in vivo or in primary culture. "Substantially homogeneous" (see below) refers to cell preparations where the cell type is of significant purity of at least 50%. The range of homogeneity may, however, be up to and including 100%. Accordingly, the range includes about 50% to 60%, about 60% to 70%, about 70% to 80%, about 80% to 90% and about 90% to 100%. This is distinguished from the term "isolated", which can refer to levels that are substantially less. However, as used herein, the term "isolated" refers to preparations in which the cells are found in numbers sufficient to exert a clinically-relevant biological effect.

However, as used herein, the term "isolated" does not indicate the presence of only hematopoietic-reconstituting cells. Rather, the term "isolated" indicates that the cells are removed from their natural tissue environment and are present at a higher concentration as compared to the normal tissue environment. Accordingly, an "isolated" cell population may further include cell types in addition to the cells at issue and may include additional tissue components. This also can be expressed in terms of cell doublings, for example. A cell may have undergone 10, 20, 30, 40 or more doublings in vitro or ex vivo so that it is enriched compared to its original numbers in vivo or in its original tissue environment (for example bone marrow, peripheral blood, umbilical cord blood, etc.).

The term "isolated" refers to a cell or cells which are not associated with one or more cells or one or more cellular components that are associated with the cell or cells in vivo. An "enriched population" means a relative increase in numbers of a desired cell relative to one or more other cell types in vivo or in primary culture.

The term "Mcl-1" is understood to refer to an apoptotic pathway molecule that protects cells from cell death. Mcl-1 has also been found to be a functional regulator of HRC self-renewing proliferation (32), encoded by a gene having, in humans, the sequence shown in NCBI Reference Sequence: NG_029146.1, incorporated by reference for the sequence. This gene is also known, like most other genes, to contain polymorphisms that still allow the gene to maintain the function. The gene also includes, for non-human uses, such as veterinary uses, orthologs from other mammals. These include companion animals, farm animals and sport animals, for example, felines, canines, bovines, equines, porcines, ovines, etc.

The term "multiple linear regression analysis" as used herein means to model the relationship between two or more explanatory variables and a dependent variable by fitting a linear equation to the data observed.

The term "Musashi2" is understood to refer to an RNA binding protein and translational inhibitor that has been shown to regulate hematopoiesis (30, 31), encoded by a gene having, in humans, the sequence shown in NCBI Reference Sequence: NM_138962.2, incorporated by reference for the sequence. This gene is also known, like most other genes, to contain polymorphisms that still allow the gene to maintain the function. The gene also includes, for non-human uses, such as veterinary uses, orthologs from other mammals. These include companion animals, farm animals and sport animals, for example, felines, canines, bovines, equines, porcines, ovines, etc.

"Pharmaceutically-acceptable carrier" is any pharmaceutically-acceptable medium for the cells used in the present invention. Such a medium may retain isotonicity, cell metabolism, pH, and the like. It is compatible with administration to a subject in vivo, and can be used, therefore, for cell delivery and treatment.

The term "phospho-Akt (ser473)" is understood to refer to a serine/threonine-specific protein kinase, also known as protein kinase B, that is phosphorylated on the amino acid serine at position 473, encoded by a gene having, in humans, the sequence shown in NCBI Reference Sequence: NCBI Reference sequence: NM 005163.2. The url follows: http://www/ncbi.nlm.nih.gov/nuccore/NM_005163.2, incorporated by reference for the sequence. There is also an Akt2 which is closely related to Akt1. It has NCBI Reference Sequence: NM 001243027.1. The url follows: http://www/ncbi.nlm/nih.gov/nuccore/NM_001243027.1, incorporated by reference for the sequence. The antibodies used in the Examples detect both Akt1 and Akt2 phosphorylations. There are variants of both Akt1 and Akt2. This gene is also known, like most other genes, to contain polymorphisms that still allow the gene to maintain the function. The gene also includes, for non-human uses, such as veterinary uses, orthologs from other mammals. These include companion animals, farm animals and sport animals, for example, felines, canines, bovines, equines, porcines, ovines, etc.

The term "phospho-Akt (thr308)" is understood to refer to a serine/threonine-specific protein kinase, also known as protein kinase B, that is phosphorylated on the amino acid threonine at position 308, encoded by a gene having, in humans, the sequence shown in NCBI Reference Sequence: NM 005163.2. The url follows: http://www.ncbi.nlm.nih.gov/nuccore/NM_005163.2, incorporated by reference for the sequence. There is also an Akt2 which is closely related to Akt1. It has NCBI Reference Sequence: NM 001243027.1. The url follows: http://www.ncbi.nlm.nih.gov/nuccore/NM_001243027.1, incorporated by reference for the sequence. The antibodies used in the Examples detect both Akt1 and Akt2 phosphorylations. There are variants of both Akt1 and Akt2. This gene is also known, like most other genes, to contain polymorphisms that still allow the gene to maintain the function. The gene also includes, for non-human uses, such as veterinary uses, orthologs from other mammals. These include companion animals, farm animals and sport animals, for example, felines, canines, bovines, equines, porcines, ovines, etc.

The term "phospho-GSK-3β," is understood to refer to glycogen synthase kinase-3beta, which is a serine/threonine protein kinase that is phosphorylated on the amino acid serine at position 9, encoded by a gene having, in humans, the sequence shown in NCBI Reference Sequence: NM 002093.3. The url follows: http://www.ncbi.nlm.nih.gov/nuccore/NM_002093.3, incorporated by reference for the sequence. Variants exist. This gene is also known, like most other genes, to contain polymorphisms that still allow the gene to maintain the function. The gene also includes, for non-human uses, such as veterinary uses, orthologs from other mammals. These include companion animals, farm animals and sport animals, for example, felines, canines, bovines, equines, porcines, ovines, etc.

The term "potency" refers to the ability of a cell population to provide a specific biological effect. In one embodiment of the invention, the high r value, when used to assess associative expression of two or more genes, enables one to select/identify cells that have clinically-relevant potency for hematopoietic reconstitution. In that sense, the term "potency" refers to the ability of a cell population to provide hematopoietic-reconstituting cell effects, e.g., self-renewal and/or differentiation sufficient to achieve a clinically-detectable result The term "principal component analysis," as used herein, means a specific mathematical procedure used to reduce the number of variables in a dataset by eliminating redundant (correlated) variables so that a set of new uncorrelated variables remain. This procedure also is used to reveal underlying structure by demonstrating relationships among the variables that cannot readily be observed without this type of mathematical analysis.

Principal component analysis is a specific mathematical procedure to accomplish the task of variable reduction and structure detection. Other unique procedures to extract the important factors among many variables include least squares, principal axis factoring, maximum likelihood, and others.

The inventor performed principal component analysis via a statistics program, SPSS, which is distributed by IBM.

The term "PTEN," is understood to refer to a phosphatase and tensin homolog, encoded by a gene having, in humans, the sequence shown in NCBI Reference Sequence: NM 000314.4. The url follows: http://www.ncbi.nlm.nih.gov/nuccor/NM_000314.4, incorporated by reference for the sequence. This gene is also known, like most other genes, to contain polymorphisms that still allow the gene to maintain the function. The gene also includes, for non-human uses, such as veterinary uses, orthologs from other mammals. These include companion animals, farm animals and sport animals, for example, felines, canines, bovines, equines, porcines, ovines, etc.

The term "reduce" as used herein means to prevent as well as decrease. In the context of treatment, to "reduce" is to both prevent or ameliorate one or more clinical symptoms. A clinical symptom is one (or more) that has or will have, if left untreated, a negative impact on the quality of life (health) of the subject.

"Selecting" a cell with a desired level of potency can mean identifying (as by assay), isolating, and expanding a cell. This could create a population that has a higher potency than the parent cell population from which the cell was isolated.

To select a cell would include both an assay to determine if there is the desired effect and would also include obtaining that cell. The cell may naturally have the effect in that the cell was not incubated with or exposed to an agent that induces the effect. The cell may not be known to have the effect prior to conducting the assay. As the effects could depend on gene expression and/or secretion, one could also select on the basis of one or more of the genes that cause the effects.

Selection could be from cells in a tissue. For example, in this case, cells would be isolated from a desired tissue, expanded in culture, selected for a desired effect, and the selected cells further expanded.

Selection could also be from cells ex vivo, such as cells in culture. In this case, one or more of the cells in culture would be assayed for the effect and the cells obtained that have the effect could be further expanded.

Cells could also be selected for enhanced effect. In this case, the cell population from which the enhanced cell is obtained already has the effect. Enhanced effectiveness means a higher average amount of the effect per cell than in the parent population.

The parent population from which the enhanced cell is selected may be substantially homogeneous (the same cell type). One way to obtain such an enhanced cell from this population is to create single cells or cell pools and assay those cells or cell pools for the effect to obtain clones that naturally have the effect (as opposed to treating the cells with a modulator of the effect) and then expanding those cells that are naturally enhanced.

However, cells may be treated with one or more agents that will enhance the effect of endogenous cellular pathways. Thus, substantially homogeneous populations may be treated to enhance modulation.

If the population is not substantially homogeneous, then, it is preferable that the parental cell population to be treated contains at least 100 of the effective cell type in which enhanced effect is sought, more preferably at least 1,000 of the cells, and still more preferably, at least 10,000 of the cells. Following treatment, this sub-population can be recovered from the heterogeneous population by known cell selection techniques and further expanded if desired.

Thus, desired levels of the effect may be those that are higher than the levels in a given preceding population. For example, cells that are put into primary culture from a tissue and expanded and isolated by culture conditions that are not specifically designed to have the effect, may provide a parent population. Such a parent population can be treated to enhance the average effect per cell or screened for a cell or cells within the population that express higher effect. Such cells can be expanded then to provide a population with a higher (desired) effect.

"Self-renewal" refers to the ability to produce replicate daughter stem cells having differentiation potential that is identical to those from which they arose. Self-renewal refers to a type of cellular proliferation.

"Stem cell" means a cell that can undergo self-renewal (i.e., progeny with the same differentiation potential) and also produce progeny cells that are more restricted in differentiation potential.

"Subject" means a vertebrate, such as a mammal, such as a human. Mammals include, but are not limited to, humans, dogs, cats, horses, cows, and pigs.

"Substantially homogeneous" refers to cell preparations where the cell type is of significant purity of at least 50%. The range of homogeneity may, however, be up to and including 100%. Accordingly, the range includes about 50% to 60%, about 60% to 70%, about 70% to 80%, about 80% to 90% and about 90% to 100%. This is distinguished from the term "isolated", which can refer to levels that are substantially less. However, as used herein, the term "isolated" refers to preparations in which the cells are found in numbers sufficient to exert a clinically-relevant biological effect.

The term "therapeutically effective amount" refers to the amount of an agent determined to produce any therapeutic response in a mammal. For example, effective amounts may prolong the survivability of the patient, and/or inhibit overt clinical symptoms. Treatments that are therapeutically effective within the meaning of the term as used herein, include treatments that improve a subject's quality of life even if they do not improve the disease outcome per se. Such therapeutically effective amounts are readily ascertained by one of ordinary skill in the art. Thus, to "treat" means to deliver such an amount. Thus, treating can prevent or ameliorate any pathological symptoms.

"Treat," "treating," or "treatment" are used broadly in relation to the invention and each such term encompasses, among others, preventing, ameliorating, inhibiting, or curing a deficiency, dysfunction, disease, or other deleterious process, including those that interfere with and/or result from a therapy.

The term "UBC-13" is understood to refer to a ubiquitin-conjugating enzyme that mediates lysine-63-specific protein ubiquitination involved in signal transduction, encoded by a gene having, in humans, the sequence shown in NCBI Reference Sequence: GenBank: BC000396.2 with the following url: http://www.ncbi.nlm.nih.gov/nuccore/BC000396.2, incorporated by reference for the sequence. This gene is also known, like most other genes, to contain polymorphisms that still allow the gene to maintain the function. The gene also includes, for non-human uses, such as veterinary uses, orthologs from other mammals. These include companion animals, farm animals and sport animals, for example, felines, canines, bovines, equines, porcines, ovines, etc.

"Validate" means to confirm. In the context of the invention, one confirms that a cell is an expressor with a desired potency. This is so that one can then use that cell (in treatment, banking, drug screening, etc.) with a reasonable expectation of efficacy. Accordingly, to validate means to confirm that the cells, having been originally found to have/established as having the desired activity, in fact, retain that activity. Thus, validation is a verification event in a two-event process involving the original determination and the follow-up determination. The second event is referred to herein as "validation."

Powerful methods to ascertain relationships among molecules in cells are available in experimental systems including cell lines and animal models that can be readily manipulated. A technology is needed that can discern meaningful patterns of molecular expression in clinical samples without the benefit of experimental maneuvers such as genetic knockout protocols, gene transfer procedures, activation in culture, or treatments with specific antagonists, including RNA-based inhibitors.

The inventor has developed a technology that can illuminate meaningful patterns of molecular expression in clinical specimens. Flow cytometry, a recognized diagnostic platform, was used to obtain molecular expression data with high precision which allows for powerful statistical analysis. This procedure can uncover meaningful patterns of molecular associations in cells from clinical samples, and these patterns have provided valuable insights that may be useful in evaluating and treating patients. Because flow cytometry is used, the cells do not have to be purified or even enriched. Cellular subsets can be assessed by multi-color staining approaches.

Although flow cytometry has been used for many years, this technology has not been focused on molecular expression levels. Instead it has mostly been used to assess cellular subpopulations. Even when subpopulations cannot be detected based on a peak-trough-peak configuration of intensity distribution results are routinely expressed as percentages of the total beyond a threshold value. Expression levels using flow cytometry have been reported in the research literature and have been used in clinical practice; however, these expression levels have not previously been used to assess relationships among molecules in the way that the inventor has now developed.

The attributes of an analytical paradigm that allows for the mapping of molecular expression levels and close molecular associations in clinical specimens are 1) a technology that can assign molecular expression to meaningful subsets of cells; 2) the capacity to measure the levels of molecules with significant precision, reproducibility, and sensitivity; 3) selection of a meaningful palette of molecules to analyze; 4) natural variability in expression levels distributed among the subject population; 5) a large enough sample size to be able to clearly discern the natural variability in expression levels; and 6) rigorous statistical evaluation that eliminates marginal associations and expression differences.

The Example shows how the inventor has reduced the invention to practice. For #1 flow cytometry was used. For #2 EAS was used. For #3 meaningful molecules were selected for assessment. For #4 the natural variability of molecular expression levels was observed. For #5 20 samples/groups were included to obtain high quality results; however, 15 samples and even 10 samples can give good data. 30 samples are likely to provide even better results. For #6 the following have been used: correlation matrices, principle component analysis, factor analysis, cluster analysis, bootstrapping, and multiple linear regression analysis. The quality of the results was indicated by eliminating all correlations with r values less than 0.6. In that way the inventor was able to map the relationships of molecules in cells from clinical specimens without the need for any experimental manipulations.

The application of this technology to clinical specimens would be advantageous in assessing the effects of therapies on relevant cellular populations, in developing new therapeutic options for treating a variety of clinical entities, in following the pathogenesis of diseases by assessing specific cells, in qualifying cells that are used for transplantation, and in evaluating the potency of cells used for therapeutic purposes. This technology is pertinent to any clinical entity including but not limited to cardiological disorders, cancer, stroke, autoimmune diseases, allergic diseases, organ transplantation, cellular transplantation, drug therapy, psychiatric disease, neurological disorders, renal disease, liver disease, obesity, and diabetes.

But it can also be applied in non-clinical contexts, such as determining molecular signatures of gene expression in development or in understanding the mechanism of cell division at a molecular level or learning about the pathways activated by cellular stress.

This invention could be useful in developing pharmaceuticals. For example, there may be a cell that is acting in a way that results in pathology in a particular patient. This cell would be studied in a set of patients demonstrating disease and in a control set of samples from persons that do not demonstrate the disease. By comparing the associations from each group one could ascertain what pathways are associated in the cells from patients with the disease and not correlated in the cells from the control group. Those pathways that have been identified in this way could be targeted for disruption by potential pharmaceutical agents that are known to interrupt those pathways. It is reasonable to assume that some agents would interrupt the pathways and thereby alter the activity of the pathogenic cell and thereby result in a therapeutic effect. The aberrant cell may be a neoplastic cell (cancer) or it could be an immunoregulatory cell (regulatory T lymphocytes) or it could be an infected cell (monocyte/macrophage infected with *M. tuberculosis*).

This scheme can also be applied in reverse. There may be an agent that interrupts a specific pathway. One may want to find a disease with pathogenic cells that are dependent on this pathway. The methods of the invention could be used to find the cell(s) responsible for pathology and that rely on that pathway.

Finally, one could simultaneously analyze multiple cellular subpopulations using a multiplexed configuration. Flow cytometry allows one to do this by staining for multiple types of cells simultaneously.

Various techniques for assessing the levels of expression of the one or more genes that may be used include, but are not limited to, flow cytometry, flow cytometry with tyramide deposition technology (EAS), single cell mass cytometry, immunohistochemistry, western analysis after CD34$^+$ cell isolation, enzyme-linked immunosorbent assays (ELISA), and nucleic acid analysis including single cell polymerase chain reaction (PCR).

In one embodiment, the levels of gene expression are assessed by EAS, disclosed, for example, in U.S. Pat. Nos. 6,280,961, 6,335,173, and 6,828,109, incorporated by reference for the amplification methods disclosed.

Gene expression can be assessed by directly assaying protein or RNA (or modifications). This can be done through any of the well-known techniques available in the art, such as by flow cytometry and other antibody-based detection methods, and PCR and other hybridization-based methods.

In order to obtain results with enough precision and reproducibility to uncover the close associations among molecules in cells, the inventor used widely-accepted laboratory methods, such as the use of a dedicated flow cytometer, the use of antibody probes from a single commercial lot, the use of fluorescence-minus-one controls instead of isotype/subtype matched immunoglobulin controls, and the coordination of the procedure among all technologists performing the assay.

Statistical tools beyond the Pearson product moment correlation can be used with the dataset generated as disclosed. Other statistical measures include, but are not limited to, factor analysis, principal component analysis, multiple linear regression, logistic regression modeling, Bayesian linear regression, and other tools known to those skilled in the art.

EXAMPLES

Model System Demonstrating an Application of the Invention

Example 1

Experimental methods can be used to reveal the relationships among various molecules in cells. For instance, genetic manipulations of research animals and cells in culture have provided a wealth of information for these experimental systems. Similarly, treatment with specific agonists and antagonists facilitates elucidation of functional relationships among cellular gene products.

A similarly powerful capability does not exist to interrogate cells from clinical specimens at a molecular level. Array technology allows for the assessment of transcripts of a large number of genes. However, interpretation of the results can be confounded by the analysis of heterogeneous mixtures of cells. This issue is particularly important because clinical specimens usually comprise multiple cell types. In the same vein, a recent discussion of global gene expression analysis cogently repudiates this technology on the basis of variability in transcription among cells (1).

We have developed a high-resolution immunophenotyping technology on a flow cytometric platform (2-9) and here show that it can reveal meaningful intermolecular associations without experimental manipulation in specific subsets of relevant cells. For this analysis, we chose to focus on hematopoietic reconstituting cells (HRC) since they are clinically important for transplantation and since they occur as a minor subpopulation of mononuclear cells.

HRC reside naturally in the bone marrow and can be identified by the expression of CD34 on the cell surface. These cells may leave the marrow to circulate in the peripheral blood in small numbers and are known to retain the capability to reconstitute hematopoiesis upon transplantation (10-12).

In the bone marrow HRC are affected by constitutive signals received via osteoblasts, endothelial cells, and extracellular matrix (13-15). These signals tether the HRC in the bone marrow niche through adhesion molecule interactions. Disruption of these interactions can result in the mobilization of HRC from the bone marrow to the peripheral circulation. The precise molecular mechanisms involved in the movement of CD34+ HRC into the circulation are not well understood. However, it is known that CXCR4 expressed on CD34+ HRC and its ligand stromal-derived factor-1 constitutively expressed by bone marrow stromal cells regulate bone marrow residency versus mobilization (15). Other important signals may be involved such as the interaction of the β1 integrin CD49d, which is expressed by HRC, and VCAM-1, which is expressed on endothelial and stromal cells (16,17). Additionally, parathyroid hormone has been shown to be active in maintaining the HRC niche in the bone marrow (14,15). Treatment with the chemokine GROβ, a ligand for CXCR2, also affects mobilization of HRC (18,19). Such mobilization could be achieved by disrupting or activating a variety of different signals. Once HRC leave the bone marrow, they encounter and respond to a different set of signals that reflect the composition of the serum and that originate in distinct cells such as other blood cells and endothelial cells.

Expression levels of 16 molecules known for their importance in HRC function were assessed in 20 samples of CD34$^+$ cells from the bone marrow and peripheral blood of healthy adults. The analytes included pathway molecules (phospho-Akt(ser308), phospho-Akt(thr473), β-catenin, GAB2, PTEN, and phospho-GSK-3β) (20-28), transcription factors (HoxB4, GATA2, cMyc, Runx1, and E47) (29-40), a transcriptional repressor (Bmi-1) (41,42), a translational regulator (Musashi-2) (43,44), an anti-apoptotic molecule (Mcl-1) (45), a K63-specific ubiquitin-conjugating enzyme (UBC13) (46), and an autophagy protein (Atg7) (47). All of these molecules have been previously associated with HRC function based on the results of experimental manipulations (20-47).

HRC were identified in the various sources by staining for CD34 expression, and the expression levels of the various molecules associated with HRC function were assessed with enzymatic amplification staining (EAS™) (2-9). Amplification of the fluorescent signals was important in order to expand the dynamic range of detection which thereby allowed us to make reliable and precise quantitative comparisons. Flow cytometric analysis included gating for mononuclear cells, gating for CD34+ cells, and determination of the median fluorescence intensity of the amplified peak for the 16 molecules associated with HRC function.

Figure 2:
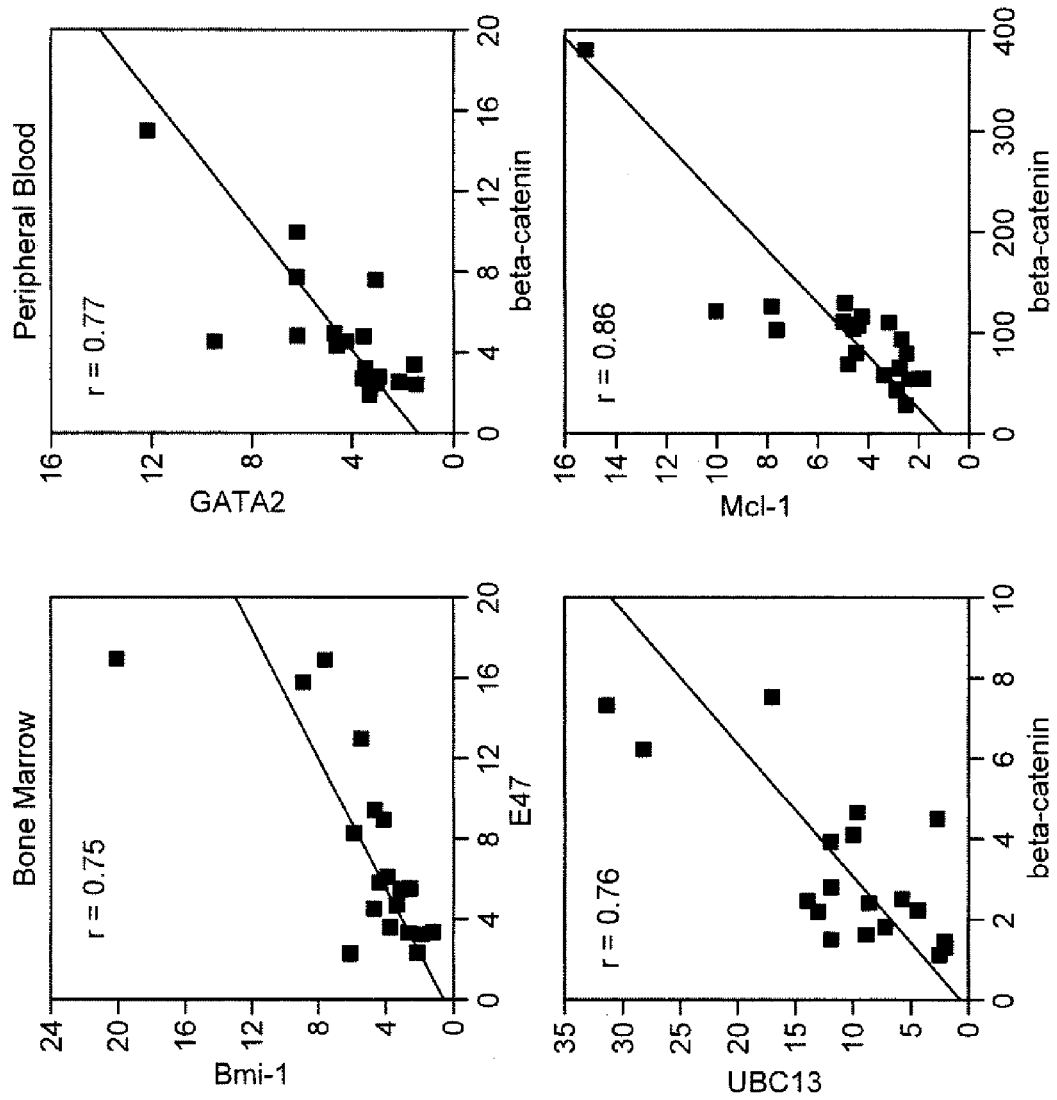
FIG. 2. Representative results of bivariate correlations with r≥0.6 in CD34$^+$ HRC. Expression levels of E47 and Bmi-1 in CD34$^+$ HRC from the bone marrow of 20 healthy volunteers are shown in the upper left panel. Expression levels of β-catenin and UBC13 in CD34$^+$ HRC from the bone marrow of 20 healthy volunteers are shown in the lower left panel. Expression levels of β-catenin and GATA2 in CD34$^+$ HRC from the peripheral of 20 healthy volunteers are shown in the upper right panel. Expression levels of β-catenin and Mcl-1 in CD34$^+$ HRC from the peripheral blood of 20 healthy volunteers are shown in the lower right panel. The Pearson correlation coefficient r is shown in each panel. The linear regression is shown (line) for each plot.

For each source 120 molecular pairs were assessed for association by evaluating the Pearson product-moment correlation coefficient. We set a stringent standard in evaluating the bivariate correlations (r≥0.6; p≤0.005). Using this criterion we found that the CD34+ HRC from the bone marrow demonstrated 10 significant correlations and the CD34+ HRC from the peripheral blood bad 29 correlated molecular pairs. Representative bivariate plots are shown (FIG. 2).

Figure 3:
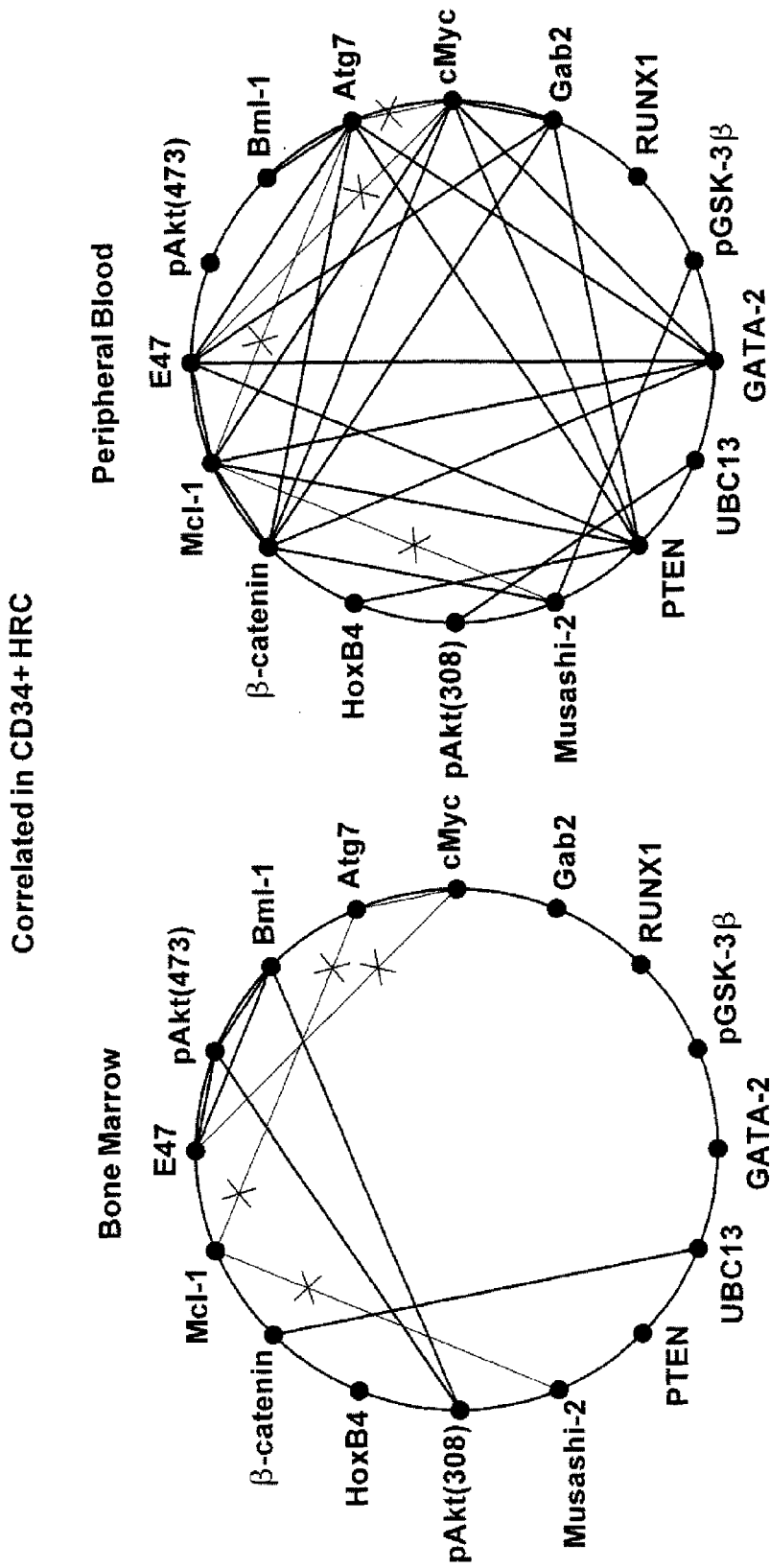
FIG. 3. Correlations among 16 molecules in CD34$^+$ HRC. Expression levels of 16 molecules shown on the perimeter of the wheels were assessed for bivariate correlations, and all correlations with r≥0.6 are shown by connectors between pairs of molecules. The results of CD34$^+$ HRC from the bone marrow (left) and peripheral blood (right) of healthy volunteers are shown. The connectors (x) represent molecular expression levels that correlate in HRC from both sources. The other connectors represent significant correlations that are unique to the specific source.
Figure 4A:
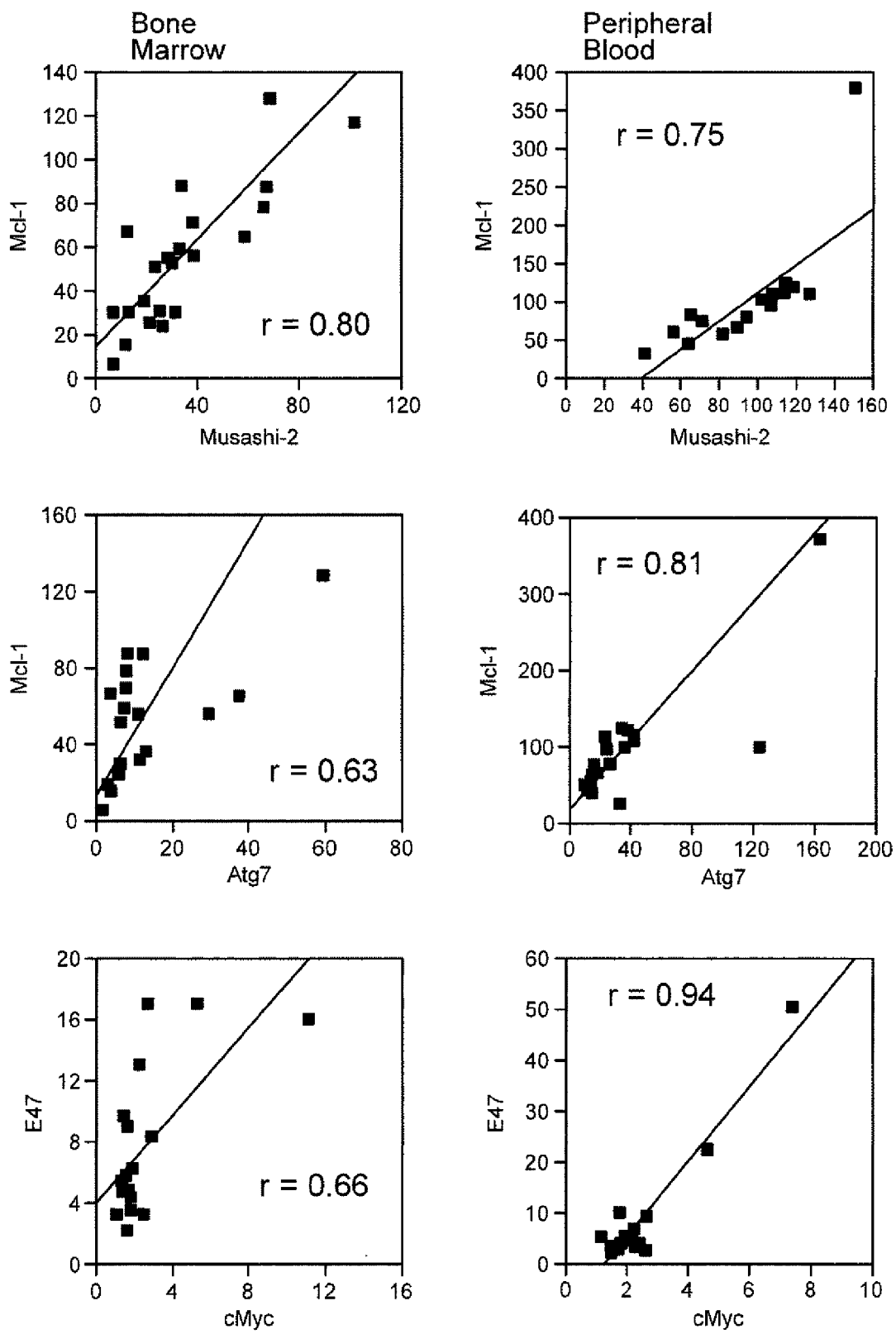
FIG. 4. Bivariate correlations of expression levels for 3 sets of molecules in HRC, from 6 sources. Expression levels of Musashi-2 and Mcl-1 (top row), Atg7 and Mcl-1 (middle row), and cMyc and E47 (bottom row) in CD34$^+$ HRC from 20 samples derived from 6 different sources are shown. The Pearson correlation coefficient r is shown in each panel. Linear regression is shown (line) for all plots with r≥0.6. The sources of the cells include bone marrow from healthy persons, peripheral blood from healthy persons, peripheral blood from healthy persons treated with G-CSF, peripheral blood from patients with plasma cell myeloma treated with cyclophosphamide and G-CSF, peripheral blood from patients with non-Hodgkin lymphoma treated with cyclophosphamide and G-CSF, and umbilical cord blood. The right-most column shows the expression levels of the samples aggregated from all sources that showed significant correlations.
Figure 4B:
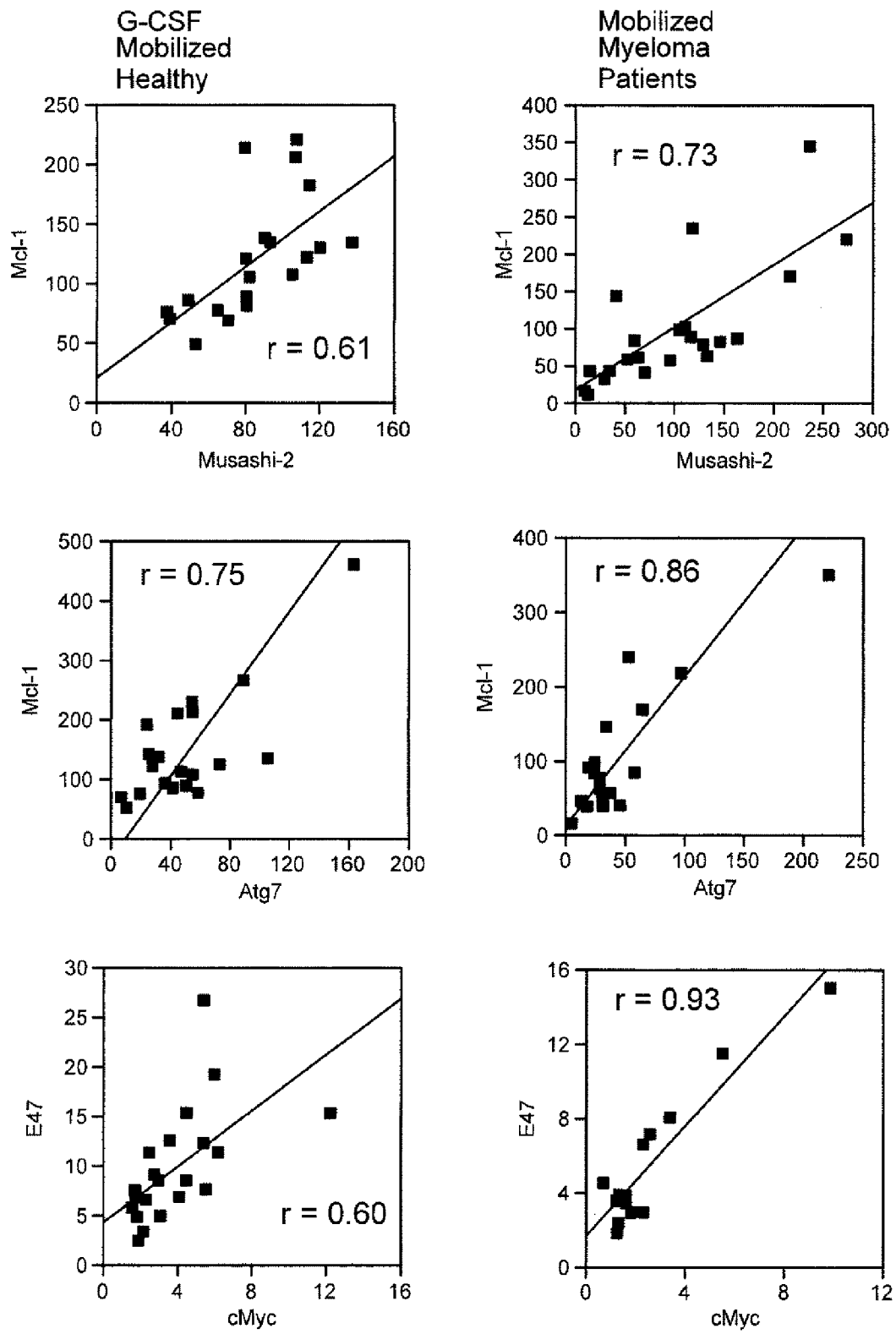
Figure 4C:
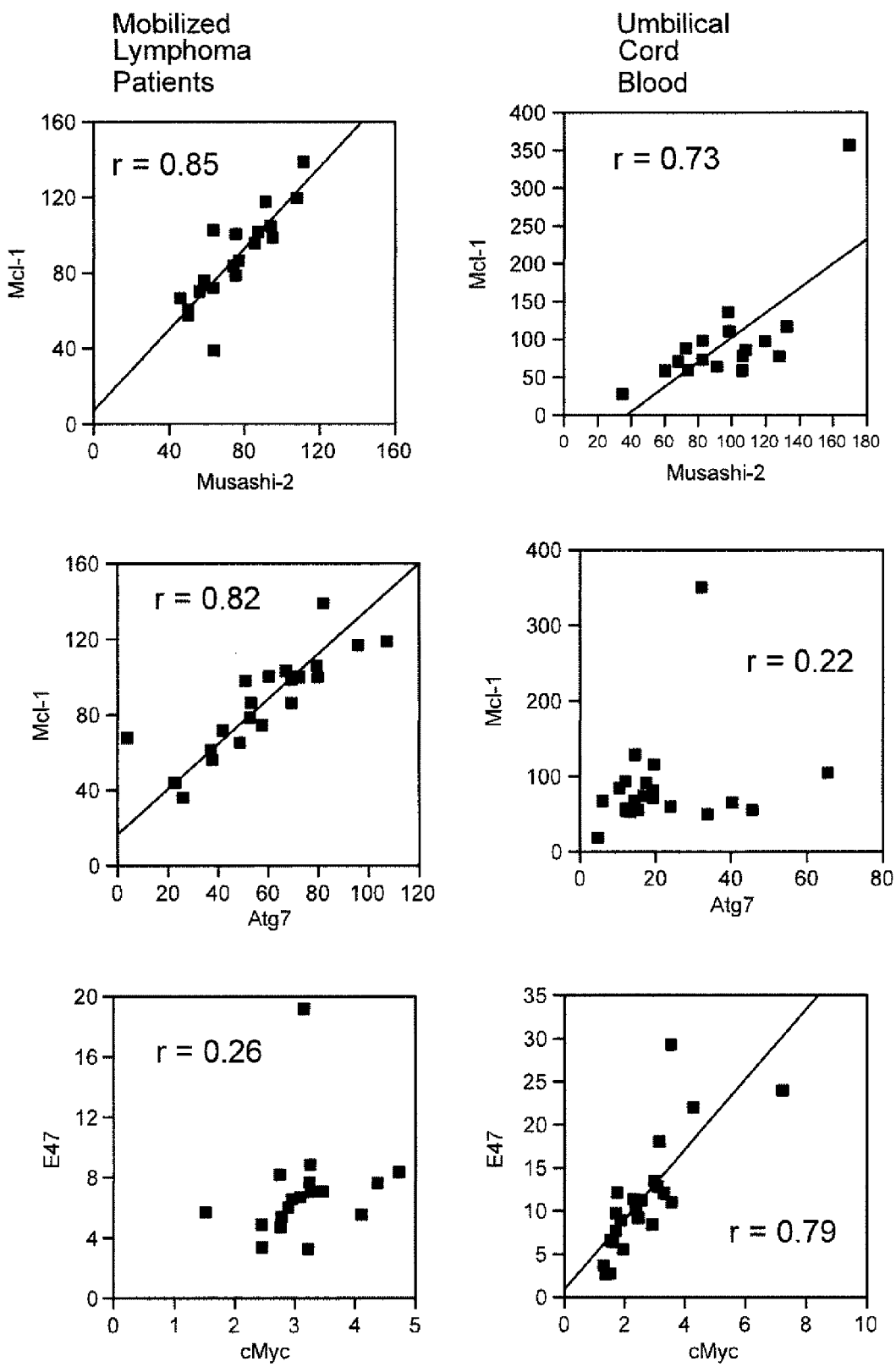
Figure 4D:
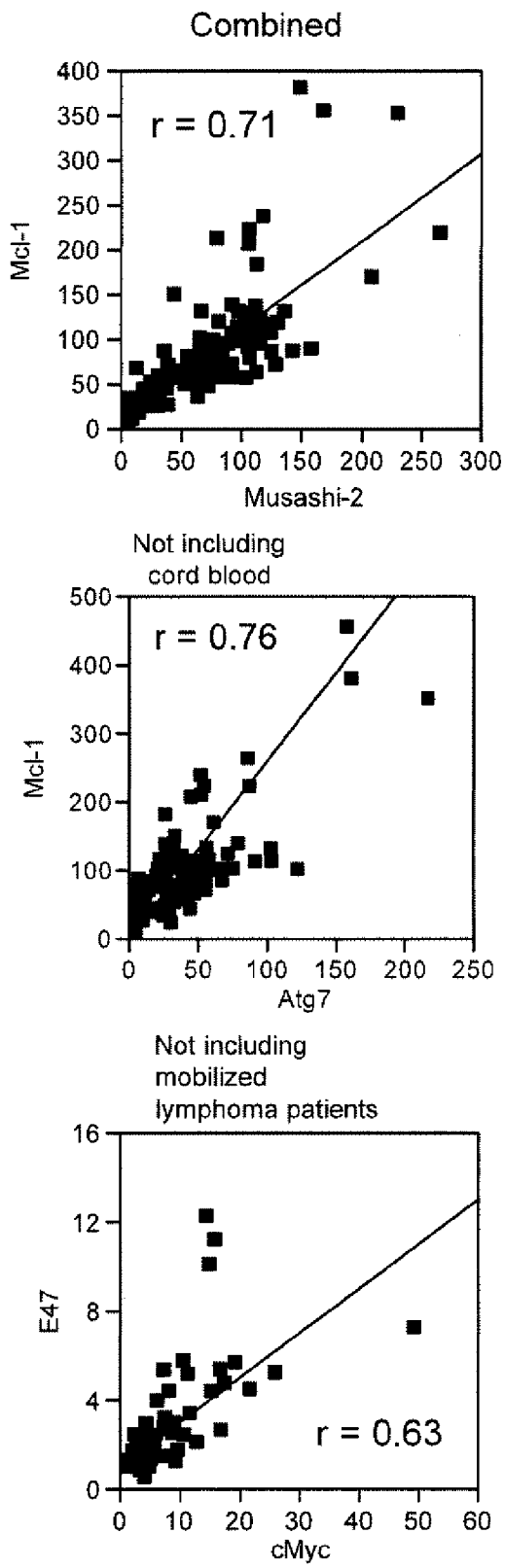

In FIG. 3 all the correlations with r≥0.6 are shown for HRC from both sources. The unmarked connectors represent the bivariate correlations that are unique to each source and the connectors with an x signify the shared correlations. The correlations common to both bone marrow and peripheral blood are Musashi-2:Mcl-1, Mcl-1:Atg7, Atg7:cMyc, and cMyc:E47. This configuration of intermolecular associations represents a shared linear sequence of strong bivariate correlations.

Several sets of molecules were significantly correlated in bone marrow resident HRC but not correlated in the peripheral blood HRC (FIG. 3). Phospho-Akt(thr308):phospho-Akt (ser473), phospho-Akt(thr308):Bmi-1, and phospho-Akt (ser473):Bmi-1 forms a loop of tightly correlated molecular expression levels, and E47:Bmi-1, E47:phospho-Akt (ser473), and phospho-Akt(473):Bmi-1 forms a second contiguous set. These 2 loops are contiguous with a single shared correlation, phospho-Akt(473):Bmi-1.

Most of the correlations found in the peripheral blood HRC were unique (FIG. 3). The correlations found only in these HRC demonstrated several nodes of associations, specific molecules that are strongly correlated with several other molecules. There are major nodes involving E47, cMyc, Atg7, Mcl-1, and β-catenin each with 7 associations, PTEN with 6 associations, and GATA2 with 5 associations.

To evaluate whether the shared linear sequence of correlated expression levels (FIG. 3) can be found in HRC from other sources, we analyzed 20 samples each from umbilical cord blood and healthy donors, patients with myeloma, and patients with non-Hodgkin lymphoma who had been pharmacologically treated to mobilize bone marrow HRC into the peripheral blood (FIG. 4). The correlation between Musashi-2 and Mcl-1 was found in CD34+ HRC from all 6 sources (r≥0.6, p≤0.005); moreover, the strong correlations were maintained upon aggregating the data. These results indicate that this association is invariant in HRC, and it may represent an essential intermolecular relationship for these cells. Also, finding the Musashi-2:Mcl-1 association in CD34+ cells from 6 independently derived sources illustrates how the analyses are reliable and accurate.

The Atg7:Mcl-1 correlation was found in all HRC except cord blood, the only source whose HRC did not derive from the adult bone marrow (FIG. 4). The cMyc:E47 correlation was found in all HRC except those that were pharmacologically mobilized from lymphoma patients (FIG. 4). Thus, though these correlations are found in most HRC sources, they are not found in all sources and may reflect specific differences unique to these HRC.

The analytical paradigm developed in our investigation revealed a molecular expression signature that is shared between HRC from the bone marrow and the peripheral blood of healthy adults. A constant set of bivariate correlations was found: Musashi-2:Mcl-1, Mcl-1:Atg7, Atg7:cMyc, and cMyc:E47. Phospho-GSK-3β was correlated with Musashi-2 in HRC from the peripheral blood (FIG. 3) and the correlation coefficient for these 2 molecules in HRC from the bone marrow was 0.59 (p=0.006). The constant relationships from Musashi-2 to E47 represent a linear sequence of strong intermolecular associations, and it seems likely that phospho-GSK-3β extends this sequence.

We found a significant correlation in the expression of β-catenin and Mcl-1 in CD34+ HRC from the peripheral blood (r=0.86). This relationship had not been previously described in these cells; however, this same correlation was previously observed in melanoma cell lines treated in culture with a specific β-catenin inhibitor (49). Similarly, we found significant correlations in the expression of the polycomb group molecule Bmi-1 and both phospho-Akt(thr308) (r=0.91) and phospho-Akt(ser473) (r=0.91) which is consistent with previous findings in tumor cell lines that used overexpression and RNAi to show a causal relationship for Bmi-1 in the activation of the Akt pathway (50,51).

It should be noted that the correlations were discovered at physiological concentrations of the various molecules without the potentially confounding influence of cell culture. This situation is in contradistinction to the use of genetic knockout or overexpression experiments that rely on effects at levels of analytes that are not physiological.

We have described several highly significant correlations among the expression levels of a variety of molecules known to be important in HRC function. Thus, we are describing a web of interactions that define a signature of HRC specific for each source. The capacity to define molecular pathways in cells from clinical specimens without undue experimental manipulations represents a new powerful analytical capability.

There are 2 ways to further enhance the analytical capabilities of the paradigm. Assessing expression levels of more molecules would provide a more detailed picture of the expression levels, tight associations, nodes of associations, and multi-molecular factors that exist in cells. Also, the inclusion of more samples in each group would enhance the statistical power of the analysis.

Example 2

Expression levels of 16 molecules known for their importance in HRC function were assessed in 20 samples of CD34+ cells from the bone marrow, the peripheral blood of healthy adults who had been treated with G-CSF to mobilize the HRC, and umbilical cord blood. The analytes included pathway molecules (phospho-Akt(ser308), phospho-Akt (thr473), β-catenin, GAB2, PTEN, and phospho-GSK-3β) (20-28), transcription factors (HoxB4, GATA2, cMyc, Runx1, and E47) (29-40), a transcriptional repressor (Bmi-1) (41,42), a translational regulator (Musashi-2) (43,44), an anti-apoptotic molecule (Mcl-1) (45), a K63-specific ubiquitin-conjugating enzyme (UBC13) (46), and an autophagy protein (Atg7) (47). All of these molecules have been previously associated with HRC function based on the results of experimental manipulations (20-47).

HRC were identified in the various sources by staining for CD34 expression, and the expression levels of the various molecules associated with HRC function were assessed with enzymatic amplification staining (EAS™) (2-9). Amplification of the fluorescent signals was important in order to expand the dynamic range of detection which thereby allowed us to make reliable and precise quantitative comparisons. Flow cytometric analysis included gating for mononuclear cells, gating for CD34+ cells, and determination of the median fluorescence intensity of the amplified peak for the 16 molecules associated with HRC function.

Figure 5A:
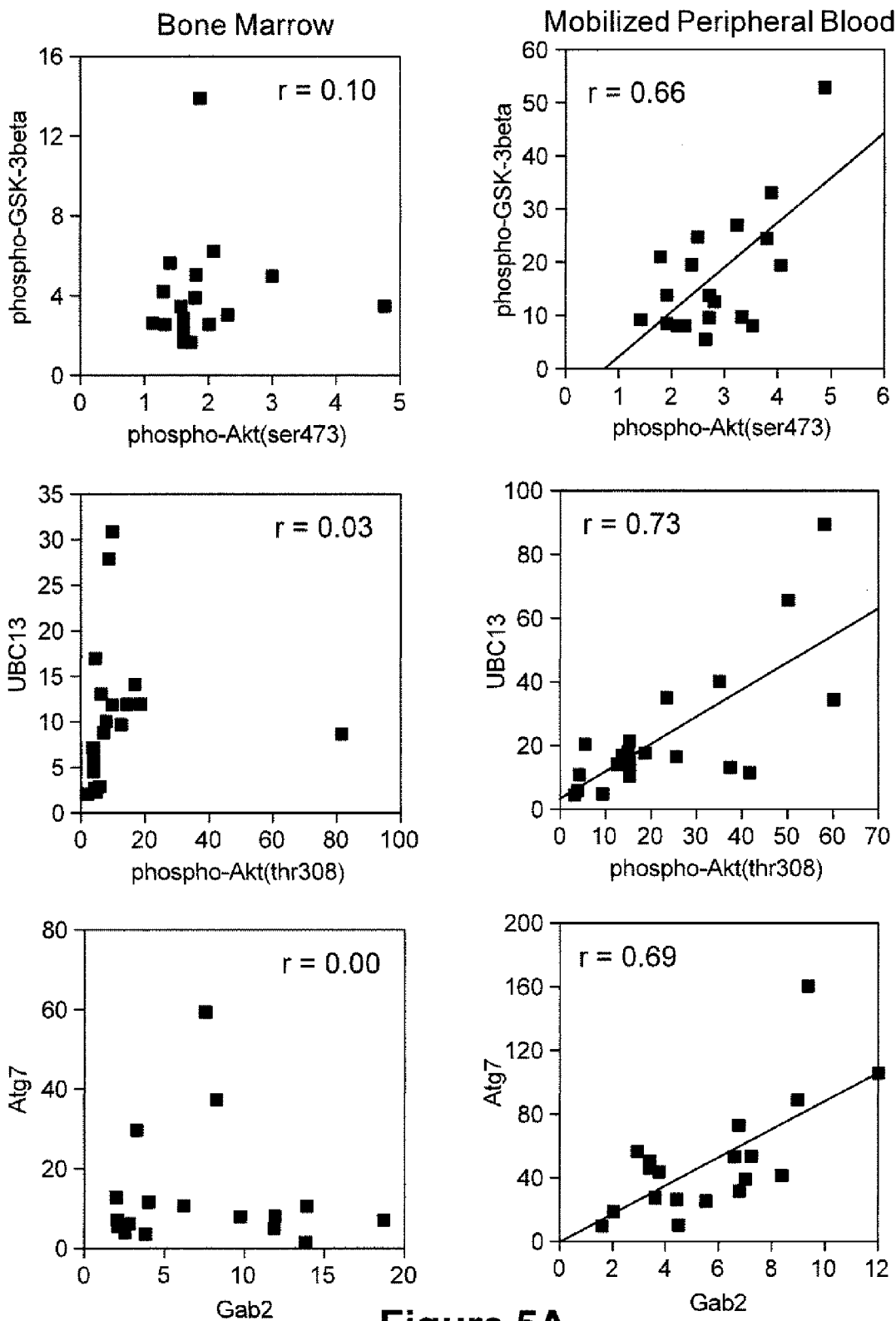
FIG. 5. Representative results of bivariate correlations with r≥0.6 in CD34+ HRC. Expression levels of phospho-Akt (ser473) and phospho-GSK-3β in CD34+ HRC are shown in the top row. Expression levels of phospho-Akt(thr308) and USC13 in CD34+ HRC are shown in the middle row. Expression levels of Gab2 and Atg7 in CD34+ HRC are shown in the bottom row. Results from the bone marrow of 20 healthy volunteers are shown in the left column of panels. Results from the peripheral blood of 20 healthy volunteers treated with G-CSF are shown in the middle, left column of panels. Results from 20 umbilical cord blood samples are shown in the middle, right column of panels. The combined results of the 40 mobilized peripheral blood and umbilical cord blood samples are shown in the right column of panels. The Pearson correlation coefficient r is shown in each panel. The linear regression is shown (line) for each plot with r>0.55.
Figure 5B:
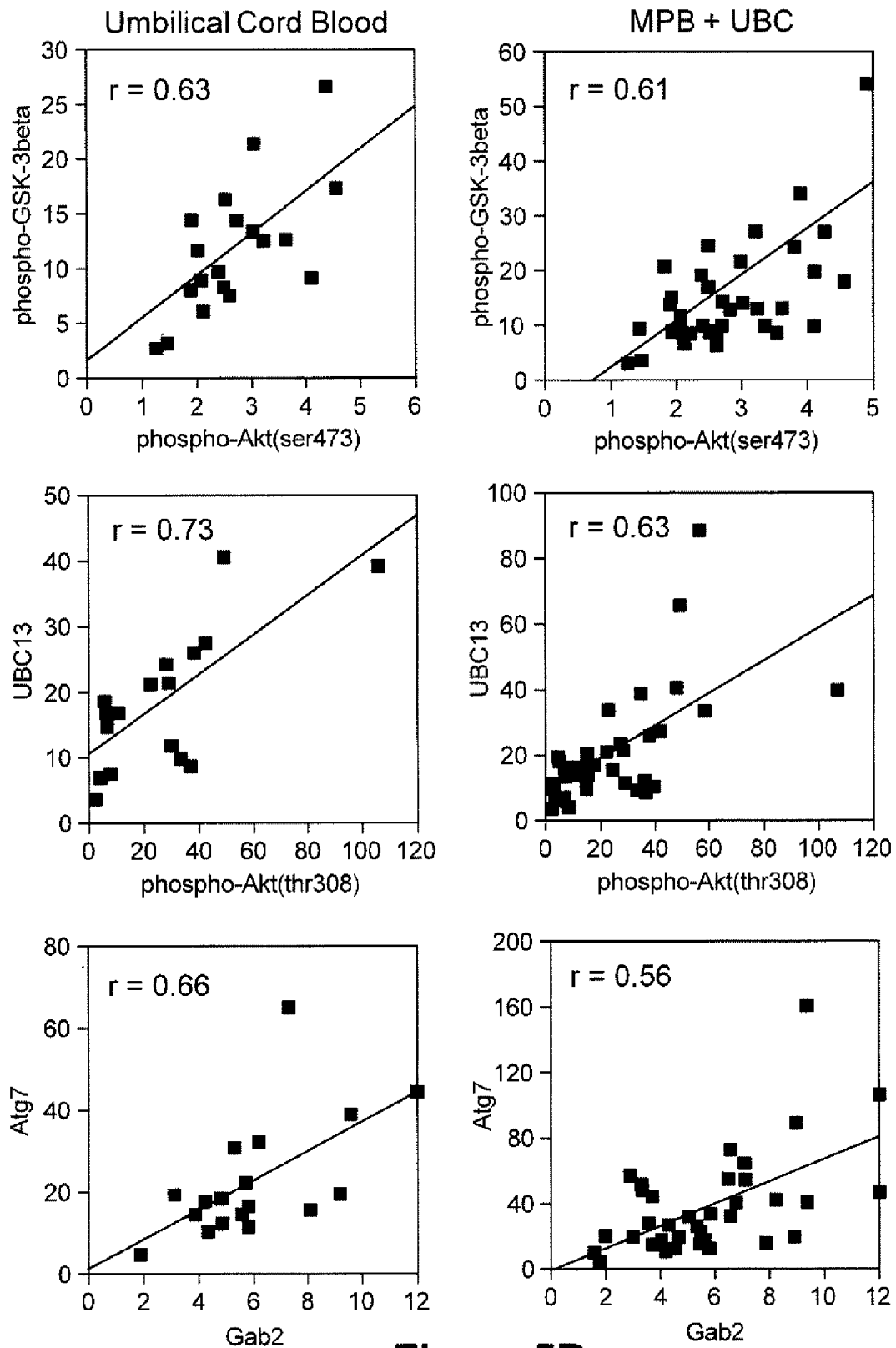

For each source 120 molecular pairs were assessed for association by evaluating the Pearson product-moment correlation coefficient. We set a stringent standard in evaluating the bivariate correlations (r≥0.6; p≤0.005). Using this criterion we found that the CD34+ HRC from the bone marrow demonstrated 10 significant correlations. For HRC from G-CSF mobilized peripheral blood cells there were 19 significant correlations and for HRC from UBC there were also 19. Only a few of these bivariate correlations from the G-CSF mobilized peripheral blood or from the umbilical cord blood are shared with HRC from the bone marrow. Representative bivariate plots are shown (FIG. 5).

Figure 6:
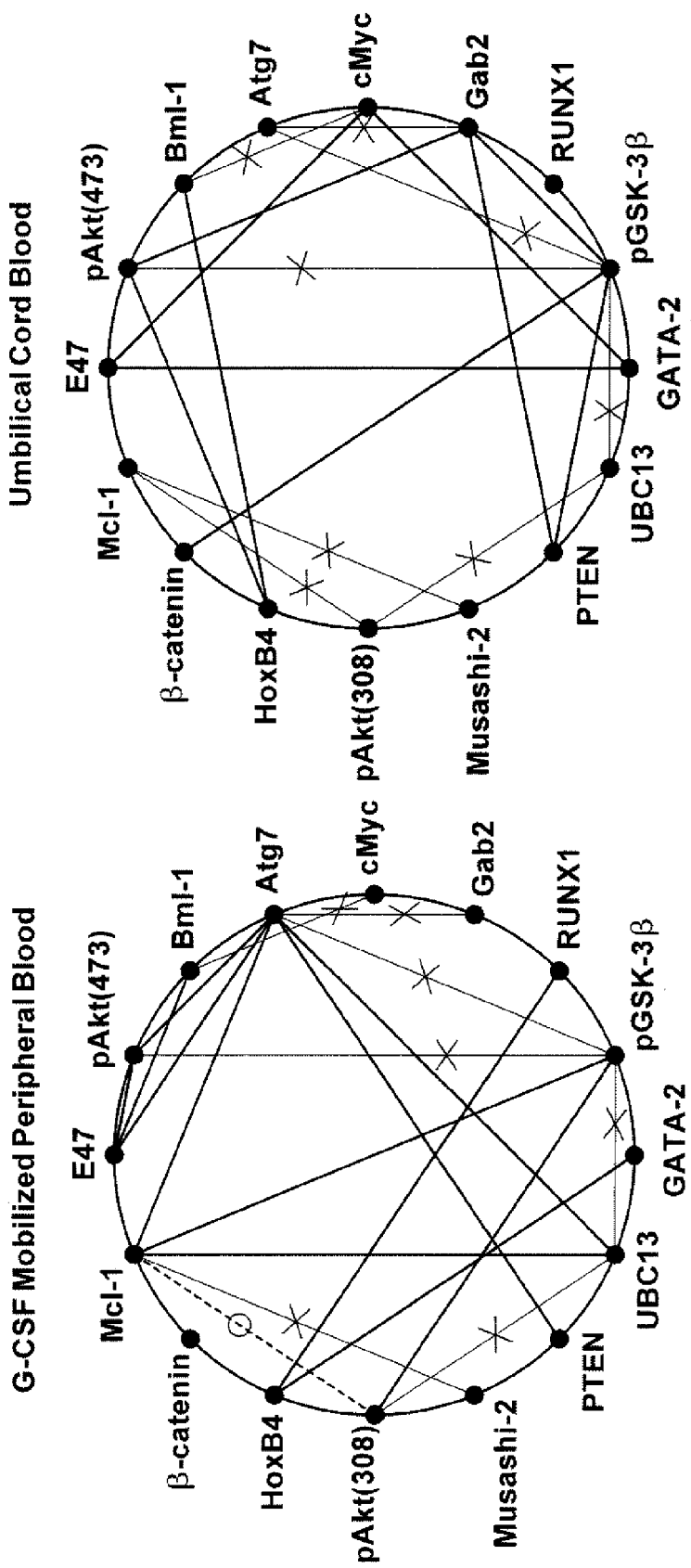
FIG. 6. Correlations among 16 molecules in CD34+ HRC. Expression levels of 16 molecules shown on the perimeter of the wheels were assessed for bivariate correlations, and all correlations with r≥0.6 are shown by connectors between pairs of molecules. The results of CD34+ HRC from the G-CSF mobilized peripheral blood of healthy adult volunteers (left) and umbilical cord blood (right) are shown. Connectors (x) represent molecular expression levels that correlate in HRC from both sources. The other connectors represent significant correlations that are unique to the specific source. The single connector (o) in the G-CSF mobilized peripheral blood wheel represents a bivariate correlation of 0.58.

In FIG. 6 all the correlations with r≥0.6 are shown for HRC from G-CSF-mobilized PB and UBC. The unmarked connectors represent the bivariate correlations that are unique to each source and connectors with an x signify the shared correlations. The correlations common to both sources are Musashi-2:Mcl-1, Mcl-1:phospho-Akt(thr308), phospho-Akt(thr308):UBC13, UBC 13:phospho-GSK-3β, phospho-GSK-3β:phospho-Akt(473), phospho-GSK-3β:Atg7, Atg7:Gab2, and eMyc:Bmi-1. It should be noted that in G-CSF-mobilized HRC, the Mcl-1:phospho-Akt(thr308) correlation demonstrated r=0.58 (connector with o.). This configuration of intermolecular associations represents a shared linear sequence of strong bivariate correlations with a bifurcation near one end. Also, the cMyc:Bmi-1 association is the only relationship not connected to the other correlated molecules. It should be noted that the only strong correlation observed in both G-CSF mobilized HRC and umbilical cord blood HRC and in bone marrow-resident HRC was Musashi-2:Mcl-1 (FIGS. 3 and 6). Finally, in FIG. 5 the data from G-CSF-mobilized HRC and UBC HRC were combined (far-right column). For all 3 molecular pairs the correlation was maintained upon combination indicating that the data are robust and that relationships are similar in each of these independently derived groups.

We found a sequence of highly associated bi-molecular correlations that were related to cells with greater potency. This sequence begins with Musashi-2 and proceeds to Mcl-1, phospho-Akt(thr308), UBC13, and phospho-GSK-3β in order. At phospho-GSK-3β the sequence bifurcates with 1 branch proceeding to phospho-Akt(ser473) and the other to Atg7 and then to Gab2. CD34+ cells from both G-CSF mobilized peripheral blood and UBC demonstrated this series of highly correlated molecules. This sequence of correlated molecules related to HRC potency has implications beyond simply identifying cells that work more effectively. It appears to represent a pathway that mediates potency. Thus, activating HRC so that these molecules are aligned with correlated expression levels may be a mechanism to enhance the potency of the cells.

Example 3

Figure 7:
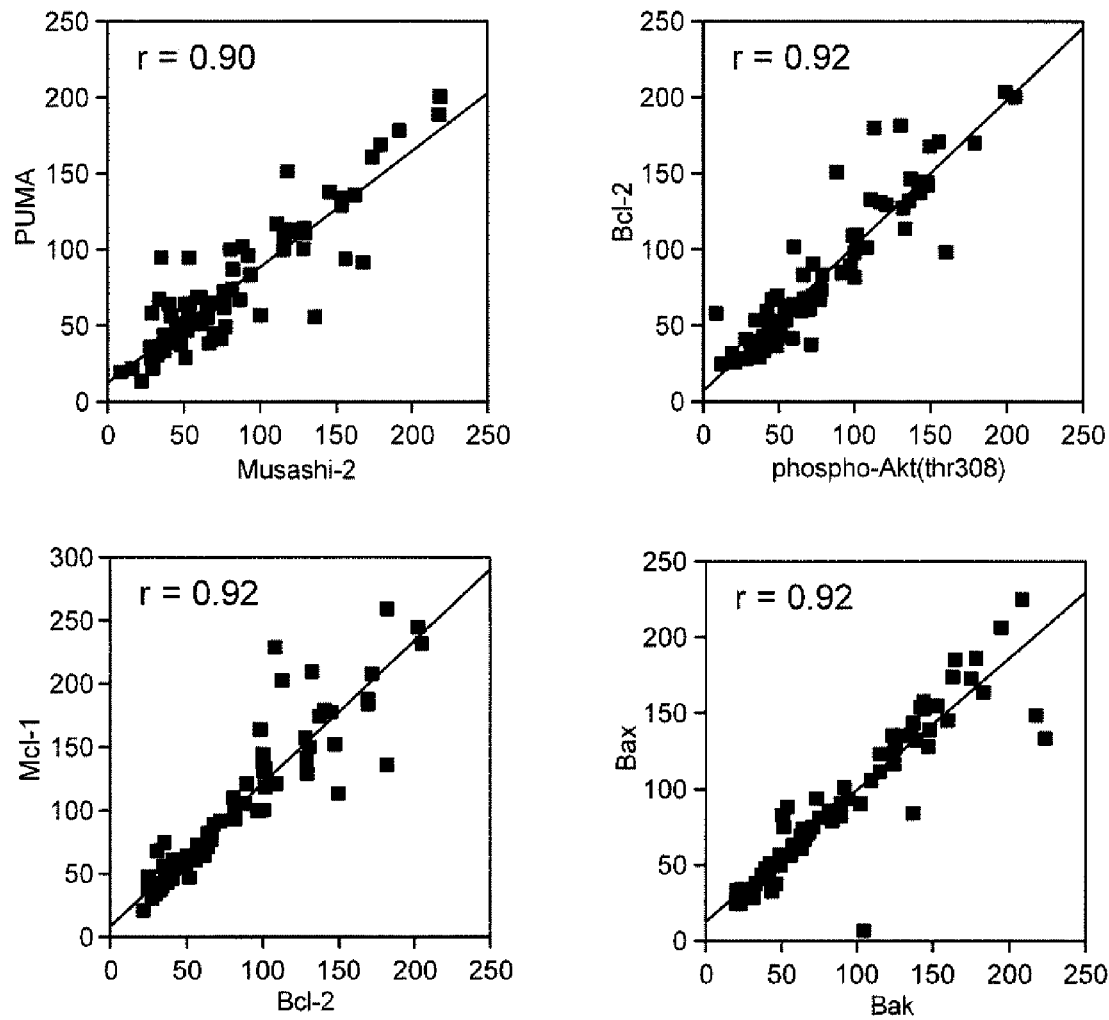
FIG. 7. Samples of peripheral blood from 79 patients diagnosed with chronic lymphocytic leukemia were assessed for the expression of 27 molecules.

Samples of peripheral blood from 79 patients diagnosed with chronic lymphocytic leukemia were assessed for the expression of 27 molecules. These molecules derived from the apoptotic pathway and various signaling pathways such as the PI3K/Akt pathway. The correlate matrix of our results demonstrated 32 bivariate correlations with r values greater than or equal to 0.85 and 100 bivariate correlations with r values greater than or equal to 0.55. With 27 molecules there are 351 bivariate relationships to assess. Examples of highly correlated molecules are in FIG. 7:

These data demonstrate the capacity to find highly correlated sets of molecules with a different set of cells and with a different set of analytes than was used in the previous studies of HRC.

REFERENCES FOR EXAMPLES

References

1. Loven, J. et al. Revisiting global gene expression analysis. *Cell* (2012) 151, 476-482.
2. Meyerson, H. J., et al. D cyclins in CD5+ B-cell lymphocproliferative disorders. Cyclin D1 and cyclin D2 identify diagnostic groups and cyclin D1 correlates with ZAP-70 expression in chronic lymphocytic leukemia. *Am J Clin Pathol.* (2006) 125, 241-250.
3. Kaplan, D. Enzymatic amplification staining for cell surface antigens. In *Current protocols in cytometry.* J. P. Robinson, editor. New York, N.Y.: Wiley (2003) 6.14.1-6.14.11.
4. Kaplan, D., et al. D cyclins in lymphocytes. *Cytometry* (2005) 63A, 1-9.
5. Kaplan, D., et al. CD5 expression by B lymphocytes and its regulation upon Epstein-Barr Virus transformation. *Proc. Natl. Acad. Sci. USA* (2001) 98, 13850-13853.
6. Kaplan, D., et al. Correlation between ZAP-70, phospho-ZAP-70, and phospho-Syk expression in leukemic cells from patients with CLL. *Cytometry B* (2010) 78, 115-122.
7. Kaplan, D. and Smith, D. Enzymatic amplification staining for flow cytometric analysis of cell surface molecules. *Cytometry* (2000) 40, 81-85.
8. Lazarus, H. M., et al. Spontaneous autologous graft-versus-host disease in plasma cell myeloma autograft recipients: Flow cytometric analysis of hematopoietic progenitor cell grafts. *Biol. Blood Marrow Transplant.* (2011) 17, 970-978.
9. Kaplan, D., et al. The functional duality of HoxB4 in hematopoietic reconstituting cells. *Cytometry A* (2013) 83A, 127-133.
10. Barr, R. D., et al. Hematopoietic stem cells in human peripheral blood. *Science* (1975) 190, 284-285.
11. Kessinger, A., et al. Reconstitution of human hematopoietic function with autologous cryopreserved circulating stem cells. *Exp. Hematol.* (1986) 14, 192-196.
12. Abrams, R. A., et al. Result of attempted hematopoietic reconstitution using isologous peripheral blood mononuclear cells: a case report. *Blood* (1980) 56, 516-520.
13. Mercier, F. E., et al. The bone marrow at the crossroads of blood and immunity. *Nature Rev. Immunol.* (2012) 12, 49-60.
14. Calvi, L. M., et al. Osteoblastic cells regulate the haematopoietic stem cell niche. Nature (2003) 425, 841-846.
15. Cashen, A. F., et al. Mobilizing stem cells from normal donors: is it possible to improve upon G-CSF? *Bone Marrow Transplant.* (2007) 39, 577-588.
16. Rettig, M. P., et al. Mobilization of hematopoietic stem and progenitor cells using inhibitors of CXCR4 and VLA-4. *Leukemia* (2012) 26, 35-53.
17. To, L. B., et al. How I treat patients who mobilize hematopoietic stem cell poorly. *Blood* (2011) 118, 4530-4540.
18. King, A. G., et al. Rapid mobilization of murine hematopoietic stem cells with enhanced engraftment properties and evaluation of hematopoietic progenitor cell mobilization in rhesus monkeys by a single injection of SB-251353, a specific truncated form of the human CXC chemokine GROβ. *Blood* (2011) 97, 1534-1542.
19. Fukuda, S. et al. The chemokine GROβ mobilizes early hematopoietic stem cells characterized by enhanced homing and engraftment. *Blood* (2007) 110, 860-869.
20. Zhang, J., et al. PTEN maintains haematopoietic stem cells and acts in lineage choice and leukaemia prevention. *Nature* (2006) 441, 518-522.
21. Juntilla, M. M., et al. AKT1 and AKT2 maintain hematopoietic stem cell function by regulating reactive oxygen species. *Blood* (2010) 115, 4030-4038.
22. Manning, B. D. and Cantley, L. C. Akt/PKB signaling: navigating downstream. *Cell* (2007) 129, 1261-1274.

23. Polak, R. and Buitenhuis, M. The PI3K/PKB signaling module as key regulator of hematopoiesis: implications for therapeutic strategies in leukemia. *Blood* (2012) 119, 911-923.
24. Reya, T., et al. A role for Wnt signaling in self-renewal of haematopoietic stem cells. *Nature* (2003) 423, 409-414.
25. Kim, J. et al. Identification of a stroma-mediated Wnt/β-catenin signal promoting self-renewal of hematopoietic stem cells in the stem cell niche. *Stem Cells* (2009) 27, 1318-1329.
26. Li, G., et al. Gab2 promotes hematopoietic stem cell maintenance and self-renewal synergistically with STAT5. *PLoS One* 5(2): e9152. Doi:10.1271/journal.pone.0009152.
27. Gu, H., et al. Cloning of p97/Gab2, the major SHP2-binding protein in hematopoietic cells, reveals a novel pathway for cytokine-induced gene activation. *Mol. Cell.* (1998) 2, 729-740.
28. Nishida, K., et al. Gab-family adapter proteins act downstream of cytokine and growth factor receptors and T- and B-cell antigen receptors. *Blood* (1999) 93, 1809-1816.
29. Sauvageau, G., et al. Overexpression of HOXB4 in hematopoietic cells causes the selective expansion of more primitive populations in vitro and in vivo. *Genes & Dev.* (1995) 9, 1753-1765.
30. Unger, C., et al. Lentiviral-mediated HoxB4 in human embryonic stem cells initiates early hematopoiesis in a dose-dependent manner but does not promote myeloid differentiation. *Stem Cells* (2008) 26, 2455-2466.
31. Wilson, A., et al. c-Myc controls the balance between hematopoietic stem cell self-renewal and differentiation. *Genes & Dev.* (2004) 18, 2747-2763.
32. Baena, E., et al. c-Myc is essential for hematopoietic stem cell differentiation and regulates Lin-Sca-1+c-Kit-cell generation through p21. *Exp. Hematol.* (2007) 35, 1333-1343.
33. Laurenti, E., et al. Hematopoietic stem cell function and survival depend on c-Myc and N-Myc activity. *Cell Stem Cell* (2008) 3, 611-624.
34. Satoh, Y., et al. Roles for c-Myc in self-renewal of hematopoietic stem cells. *J. Biol. Chem.* (2004) 279, 24986-24993.
35. Tsai, F-Y., et al. An early haematopoietic defect in mice lacking the transcription factor GATA-2. *Nature* (1994) 371, 221-226.
36. Heyworth, C., et al. A GATA-2/estrogen receptor chimera functions as a ligand-dependent negative regulator of self-renewal. *Genes & Dev.* (1999) 13, 1847-1860.
37. Ezoe, S., et al. GATA-2/estrogen receptor chimera regulates cytokine-dependent growth of hematopoietic cells through accumulation of p21waf1 and p27kip1 proteins. *Blood* (2002) 100, 3512-3520.
38. Tipping, A. J., et al. High GATA-2 expression inhibits human hematopoietic stem and progenitor cell function by effects on cell cycle. *Blood* (2009) 113, 2661-2672.
39. Liakhovitskaia, A., et al. Restoration of Runx1 expression in the Tie2 cell compartment rescues definitive haematopoietic stem cells and extends life of Runx1 knockout animals until birth. *Stem Cells* (2009) 27, 1616-1624.
40. Semerad, C. J., et al. E2A proteins maintain the hematopoietic stem cell pool and promote the maturation of myelolymphoid and myeloerythroid progenitors. *Proc. Natl. Acad. Sci. USA* (2009) 106, 1930-1935.
41. Park, I., et al. Bmi-1 is required for maintenance of adult self-renewing haematopietic stem cells. *Nature* (2003) 423, 302-305.
42. Rizo, A. et al. Repression of BMI1 in normal and lekemic human CD34+ cells impairs self-renewal and induces apoptosis. *Blood* (2009) 114, 1498-1505.
43. Kharas, M. G., et al. Musashi-2 regulates normal hematopoiesis and promotes aggressive myeloid leukemia. *Nature Medicine* (2010) 16, 903-908.
44. Andres-Aguayo, L., et al. Musashi 2 is a regulator of the HSC compartment identified by a retroviral insertion screen and knockout mice. *Blood* (2011) 118, 554-564.
45. Campbell, C. J. V., et al. The human stem cell hierarchy is defined by a functional dependence on Mcl-1 for self-renewal capacity. *Blood* (2010) 116, 1433-1442.
46. Wu, X., et al. Regulation of hematopoiesis by the k63-specific ubiquitin-conjugating enzyme Ubc13. *Proc. Natl. Acad. Sci. USA* (2009) 106, 20836-20841.
47. Mortensen, M., et al. The autophagy protein Atg7 is essential for hematopoietic stem cell maintenance. *J. Exp. Med.* (2011) 208, 455-467.
48. Sarbassov, D. D., et al. Phosphorylation and regulation Of Akt/PDB by the rictor-mROR complex. *Science* (2005) 307, 1098-1101.
49. Sinnberg, T., et al. β-catenin signaling increases during melanoma progression and promotes tumor cell survivbal and chemoresistance. *PLoS ONE* 6:e23429 (2011).
50. Guo, W., et al. Mcl-18 acts as a tumor suppressor by repressing Bmi-1 expression and down regulating Akt activity in breast cancer cells. *Cancer Res.* (2007) 67, 5083-5089.
51. Guo, B., et al. Bmi-1 promotes invasion and metastasis, and its elevated expression is correlated with an advanced stage of breast cancer. *Mol. Cancer* (2011) 10, 10-18.

What is claimed:

1. A method to establish a biologically significant association of protein expression levels among two or more proteins in a sample of cells, said method comprising assaying one sample of cells for expression levels of two or more proteins and identifying statistically-significant associations by calculating a correlation coefficient for the expression of those genes in the range of about 0.6 to about 1.0, wherein a correlation coefficient in that range signifies a biologically significant correlation.

2. The method of claim 1 wherein protein expression is assessed by flow cytometry.

3. The method of claim 1 wherein protein expression is assessed in single cells.

4. The method of claim 1 wherein protein expression assessment is assessed by enzymatic amplification staining (EAS).

5. The method of claim 1 wherein protein expression is assessed in at least 50 cells.

6. The method of claim 1 wherein the correlation coefficient is in the range of about 0.6-0.7.

7. The method of claim 1 wherein the correlation coefficient is in the range of about 0.7-0.8.

8. The method of claim 1 wherein the correlation coefficient is in the range of about 0.8-0.9.

9. The method of claim 1 wherein the correlation coefficient is in the range of about 0.9-1.0.

10. The method of claim 1 wherein the protein expression involves a modification of the protein structure such as by phosphorylation, acetylation, nitrosylation, ubiquitinalytion, or other post-translational modifications.

11. The method of claim 1 wherein the protein expression involves molecules expressed intracellularly.

12. The method of claim 1 wherein the protein expression involves molecules expressed on the surface of the cell (molecules associated with the surface membrane).

13. The method of claim 1 wherein the protein expression involves molecules expressed both intracellularly and on the cell surface.

* * * * *